United States Patent
Panowski et al.

(10) Patent No.: US 11,377,500 B2
(45) Date of Patent: *Jul. 5, 2022

(54) ANTIBODIES SPECIFIC FOR CD70 AND THEIR USES

(71) Applicant: Pfizer Inc., New York, NY (US)

(72) Inventors: Siler Panowski, Berkeley, CA (US); Tao Sai, Foster City, CA (US); Barbra Johnson Sasu, San Francisco, CA (US); Surabhi Srivatsa Srinivasan, San Francisco, CA (US); Thomas John Van Blarcom, Oakland, CA (US)

(73) Assignee: Pfizer Inc., New York, NY (US)

( * ) Notice: Subject to any disclaimer, the term of this patent is extended or adjusted under 35 U.S.C. 154(b) by 303 days.

This patent is subject to a terminal disclaimer.

(21) Appl. No.: 16/264,485

(22) Filed: Jan. 31, 2019

(65) Prior Publication Data

US 2019/0233529 A1    Aug. 1, 2019

Related U.S. Application Data

(60) Provisional application No. 62/641,873, filed on Mar. 12, 2018, provisional application No. 62/625,019, filed on Feb. 1, 2018.

(51) Int. Cl.
*C07K 16/28* (2006.01)
*A61P 35/00* (2006.01)
*A61K 39/00* (2006.01)

(52) U.S. Cl.
CPC .......... *C07K 16/2875* (2013.01); *A61P 35/00* (2018.01); *C07K 16/2809* (2013.01); *A61K 2039/505* (2013.01); *C07K 2317/31* (2013.01); *C07K 2317/526* (2013.01); *C07K 2317/53* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ............ C07K 16/2875; C07K 16/2809; C07K 2317/565; C07K 2317/31; C07K 2317/76; C07K 2317/53; C07K 2317/92; C07K 2317/732; C07K 2317/734; C07K 2317/526; A61P 35/00; A61K 2039/505
See application file for complete search history.

(56) References Cited

U.S. PATENT DOCUMENTS

| | | |
|---|---|---|
| 4,676,980 A | 6/1987 | Segal et al. |
| 4,683,195 A | 7/1987 | Mullis et al. |
| 4,683,202 A | 7/1987 | Mullis |
| 4,754,065 A | 6/1988 | Levenson et al. |
| 4,777,127 A | 10/1988 | Suni et al. |
| 4,800,159 A | 1/1989 | Mullis et al. |
| 4,816,567 A | 3/1989 | Cabilly et al. |
| 4,975,278 A | 12/1990 | Senter et al. |
| 5,037,743 A | 8/1991 | Welch et al. |
| 5,047,335 A | 9/1991 | Paulson et al. |
| 5,143,830 A | 9/1992 | Holland et al. |
| 5,219,740 A | 6/1993 | Miller et al. |
| 5,278,299 A | 1/1994 | Wong et al. |
| 5,422,120 A | 6/1995 | Kim |
| 5,500,362 A | 3/1996 | Robinson et al. |
| 5,510,261 A | 4/1996 | Goochee et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,733,743 A | 3/1998 | Johnson et al. |
| 5,750,373 A | 5/1998 | Garrard et al. |
| 5,807,715 A | 9/1998 | Morrison et al. |
| 5,814,482 A | 9/1998 | Dubensky, Jr. et al. |
| 5,821,337 A | 10/1998 | Carter et al. |
| 5,858,358 A | 1/1999 | June et al. |

(Continued)

FOREIGN PATENT DOCUMENTS

| | | |
|---|---|---|
| EP | 0 345 242 A1 | 12/1989 |
| EP | 0 519 596 A1 | 12/1992 |

(Continued)

OTHER PUBLICATIONS

U.S. Appl. No. 16/264,371, filed Feb. 2018, Chimeric Antigen Receptors Targeting CD70.*
Rudikoff S, Giusti AM, Cook WD, Scharff MD. Single amino acid substitution altering antigen-binding specificity. Proc Natl Acad Sci U S A. Mar. 1982; 79(6):1979-83. (Year: 1982).*
Paul, Fundamental Immunology, 3rd Edition, 1993, pp. 292-295 (Year: 1993).*
Bendig M. M., Methods: A Companion to Methods in Enzymology, 1995; 8:83-93 (Year: 1995).*
Padlan, Advances in Protein Chemistry, 1996, 49:57-133 (Year: 1996).*
Berglund et al, 2008, Protein Science, 17:606-613 (Year: 2008).*

(Continued)

*Primary Examiner* — Julie Wu
*Assistant Examiner* — Sung Min Yoon

(57) ABSTRACT

The present invention provides antibodies that specifically bind to CD70 (Cluster of Differentiation 70). The invention further provides bispecific antibodies that bind to CD70 and another antigen (e.g., CD3). The invention further relates to antibody encoding nucleic acids, and methods of obtaining such antibodies (monospecific and bispecific). The invention further relates to therapeutic methods for use of these antibodies for the treatment of CD70-mediated pathologies, including cancer.

36 Claims, No Drawings

Specification includes a Sequence Listing.

(56) References Cited

U.S. PATENT DOCUMENTS

| | | | |
|---|---|---|---|
| 5,866,692 A | 2/1999 | Shitara et al. | |
| 5,883,223 A | 3/1999 | Gray | |
| 5,997,867 A | 12/1999 | Waldmann et al. | |
| 6,054,297 A | 4/2000 | Carter et al. | |
| 6,180,370 B1 | 1/2001 | Queen et al. | |
| 6,180,377 B1 | 1/2001 | Morgan et al. | |
| 6,210,671 B1 | 4/2001 | Co | |
| 6,265,150 B1 | 7/2001 | Terstappen et al. | |
| 6,331,415 B1 | 12/2001 | Cabilly et al. | |
| 6,350,861 B1 | 2/2002 | Co et al. | |
| 6,352,694 B1 | 3/2002 | June et al. | |
| 6,376,471 B1 | 4/2002 | Lawrence, III et al. | |
| 6,413,942 B1 | 7/2002 | Felgner et al. | |
| 6,436,908 B1 | 8/2002 | Koch et al. | |
| 6,534,055 B1 | 3/2003 | June et al. | |
| 6,692,964 B1 | 2/2004 | June et al. | |
| 6,737,056 B1 | 5/2004 | Presta | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,314,622 B2 | 1/2008 | Arlen et al. | |
| 2006/0121005 A1 | 6/2006 | Berenson et al. | |
| 2009/0028872 A1 | 1/2009 | Terret et al. | |
| 2016/0297884 A1 | 10/2016 | Kuo et al. | |
| 2016/0297885 A1 | 10/2016 | Kuo et al. | |
| 2017/0129961 A1 | 5/2017 | Raum et al. | |
| 2017/0349668 A1* | 12/2017 | Rattel et al. | C07K 16/468 |
| 2019/0233528 A1 | 8/2019 | Srinivasan et al. | |

FOREIGN PATENT DOCUMENTS

| | | |
|---|---|---|
| EP | 0 524 968 B1 | 6/1995 |
| EP | 2 335 744 A1 | 6/2011 |
| GB | 2200651 B | 6/1991 |
| WO | WO-87/04462 A1 | 7/1987 |
| WO | WO-90/07936 A1 | 7/1990 |
| WO | WO-90/11092 A1 | 10/1990 |
| WO | WO-91/00360 A1 | 1/1991 |
| WO | WO-91/02805 A2 | 3/1991 |
| WO | WO-91/02805 A3 | 3/1991 |
| WO | WO-91/14445 A1 | 10/1991 |
| WO | WO-92/20373 A1 | 11/1992 |
| WO | WO-93/03769 A1 | 3/1993 |
| WO | WO-93/06213 A1 | 4/1993 |
| WO | WO-93/10218 A1 | 5/1993 |
| WO | WO-93/11230 A1 | 6/1993 |
| WO | WO-93/19191 A1 | 9/1993 |
| WO | WO-93/25234 A1 | 12/1993 |
| WO | WO-93/25698 A1 | 12/1993 |
| WO | WO-94/03622 A1 | 2/1994 |
| WO | WO-94/04690 A1 | 3/1994 |
| WO | WO-94/12649 A2 | 6/1994 |
| WO | WO-94/12649 A3 | 6/1994 |
| WO | WO-94/23697 A1 | 10/1994 |
| WO | WO-94/28938 A1 | 12/1994 |
| WO | WO-95/00655 A1 | 1/1995 |
| WO | WO-95/07994 A2 | 3/1995 |
| WO | WO-95/07994 A3 | 3/1995 |
| WO | WO-95/11984 A2 | 5/1995 |
| WO | WO-95/11984 A3 | 5/1995 |
| WO | WO-95/13796 A1 | 5/1995 |
| WO | WO-95/30763 A2 | 11/1995 |
| WO | WO-95/30763 A3 | 11/1995 |
| WO | WO-96/17072 A2 | 6/1996 |
| WO | WO-96/17072 A3 | 6/1996 |
| WO | WO-97/42338 A1 | 11/1997 |
| WO | WO-99/58572 A1 | 11/1999 |
| WO | WO-01/27160 A1 | 4/2001 |
| WO | WO-2004/058184 A2 | 7/2004 |
| WO | WO-2004/058184 A3 | 7/2004 |
| WO | WO-2006/044643 A2 | 4/2006 |
| WO | WO-2006/044643 A3 | 4/2006 |
| WO | WO-2006/113909 A2 | 10/2006 |
| WO | WO-2006/113909 A3 | 10/2006 |
| WO | WO-2011/143545 A1 | 11/2011 |
| WO | WO-2012/058458 A2 | 5/2012 |
| WO | WO-2012/058458 A3 | 5/2012 |
| WO | WO-2012/058460 A2 | 5/2012 |
| WO | WO-2012/058460 A3 | 5/2012 |
| WO | WO-2012/059882 A2 | 5/2012 |
| WO | WO-2012/059882 A3 | 5/2012 |
| WO | WO-2012/123586 A1 | 9/2012 |
| WO | WO-2013153391 A1 | 10/2013 |
| WO | WO-2014/039523 A1 | 3/2014 |
| WO | WO-2014/184143 A1 | 11/2014 |
| WO | WO-2014/184741 A1 | 11/2014 |
| WO | WO-2014/184744 A1 | 11/2014 |
| WO | WO-2014/191128 A1 | 11/2014 |
| WO | WO-2015/015448 A2 | 2/2015 |
| WO | WO-2015/015448 A3 | 2/2015 |
| WO | WO-2015/121454 A1 | 8/2015 |
| WO | WO-2016/120126 A1 | 8/2016 |
| WO | WO-2016/120216 A1 | 8/2016 |
| WO | WO-2017/125831 A1 | 7/2017 |
| WO | WO-2017/134140 A1 | 8/2017 |
| WO | WO-2018/152181 A1 | 8/2018 |

OTHER PUBLICATIONS

Colman P. M., Research in Immunology, 145:33-36, 1994 (Year: 2015).*

Khantasup et al., Monoclonal Antibodies in Immunodiagnosis and Immunotherapy, 2015, 34(6): 404-417 (Year: 2015).*

Murphy C, Stack E, Krivelo S, Breheny M, Ma H, O'Kennedy R. Enhancing recombinant antibody performance by optimally engineering its format. J Immunol Methods. Dec. 2018;463:127-133. (Year: 2018).*

Chen, Sci Adv. Apr. 1, 2020;6(14):eaaz7825 (Year: 2020).*

Aalberse, R.C. et al. (2002). "IgG4 breaking the rules," Immunology 105:9-19.

Aftimos, P. et al. (2017). "Dose-Escalation Study of the Anti-CD70 Antibody ARGX-110 in Advanced Malignancies," Clinical Cancer Research 23:6411-6420.

Al-Lazikani, B. et al. (1997). "Standard conformations for the Canonical structures of immunoglobulins," J. Molec. Biol. 273:927-948.

Armour, K.L. et al. (2003). "Differential binding to human FcγRIIa and FcγRIIb receptors by human IgG wildtype and mutant antibodies," Molecular Immunology 40:585-593.

Armour, K.L. et al. (1999). "Recombinant human IgG molecules lacking Fcγ receptor I binding and monocyte triggering activities," Eur. J. Immunol. 29:2613-2624.

Atkins, J.F. et al. (2007). "A case for "StopGo": Reprogramming translation to augment codon meaning of GGN by promoting unconventional termination (Stop) after addition of glycine and then allowing continued translation (Go)," RNA 13:803-810.

Balint, R.F. et al. (1993). "Antibody engineering by parsimonious mutagenesis," Gene 137:109-118.

Barbas, C.F. et al. (1994). "In vitro evolution of a neutralizing human antibody to human immunodeficiency virus type 1 to enhance affinity and broaden strain cross-reactivity," PNAS 91:3809-3813.

Berger, C. et al. (2015). "Safety of targeting ROR1 in primates with chimeric antigen receptor-modified T cells," Cancer Immunol. Res. 3:206-216.

Bierer, B.E. et al. (1993). "Cyclosporin A and FK506: molecular mechanisms of immunosuppression and probes for transplantation biology," Current Opin. Immunol. 5:763-773.

Bird, R.E. et al. (1988). "Single-chain antigen-binding proteins," Science 242:423-426.

Bloom, J.W. et al. (1997). "Intrachain disulfide bond in the core hinge region of human IgG4," Protein Science 6:407-415.

(56) References Cited

OTHER PUBLICATIONS

Boerner, P. et al. (1991). "Production of antigen-specific human monoclonal antibodies from in vitro-primed human splenocytes," J. Immunol. 147:86-95.
Boursalian, T.E. et al. (2009). "Chapter 7: Targeting CD70 for human therapeutic use," Adv. Exp. Med. Biol. 647:108-119.
Boyd, P.N. et al. (1996). "The Effect of the Removal of Sialic Acid, Galactose and Total Carbohydrate on the Functional Activity of Campath-1H," Mol. Immunol. 32:1311-1318.
Brenner, M.K. et al. (2010). "Adoptive T cell therapy of cancer," Curr. Opin. Immunol. 22:251-257.
Brown, B.A. et al. (1987). "Tumor-specific genetically engineered murine/human chimeric monoclonal antibody," Cancer Res. 47:3577-3583.
Buck, D.W. et al. (1982). "Monoclonal Antibodies Specific for Cell Culture Mycoplasmas," In Vitro 18:377-381.
Campana, D. et al. (2014). "4-1BB chimeric antigen receptors," Cancer J. 20:134-140.
Capel, P.J.A. et al. (1994). "Heterogeneity of human IgG Fc receptors," Immunomethods 4:25-34.
Chothia, C. et al. (1989). "Conformations of immunoglobulin hypervariable regions," Nature 342:877-883.
Clackson, T. et al. (1991). "Making antibody fragments using phage display libraries," Nature 352:624-628.
Clynes, R. et al. (1998). "Fc receptors are required in passive and active immunity to melanoma," PNAS 95:652-656.
Cole, S.P.C. et al. (1985). "The EBV-hybridoma technique and its application to human lung cancer," in Monoclonal Antibodies and Cancer Therapy, Proceedings of the Roche-UCLA Symposium Held in Park City, Utah, pp. 77-96.
Connelly, S. et al. (1995). "In vivo gene delivery and expression of physiological levels of functional human factor VIII in mice," Human Gene Therapy 1:185-193.
Courtois, A. et al. (2012). "Complement dependent cytotoxicity activity of therapeutic antibody fragments is acquired by immunogenic glycan coupling," Electronic Journal of Biotechnology, pp. 1-11.
Curiel, D.T. et al. (1992). "High-efficiency gene transfer mediated by adenovirus coupled to DNA-polylysine complexes," Hum. Gene Ther. 3:147-154.
Daugherty, B.L. et al. (1991). "Polymerase chain reaction facilitates the cloning, CDR-grafting, and rapid expression of a murine monoclonal antibody directed against the CD18 component of leukocyte integrins," Nucl. Acids Res. 19:2471-2476.
Dayhoff, M.O. et al. (1978). "Chapter 22: A model of evolutionary change in proteins," in Atlas of Protein Sequence and Structure, National Biomedical Research Foundation, A model of evolutionary change in proteins—Matrices for detecting distant relationships, Washington DC vol. 5, Suppl. 3, pp. 345-358.
De Haas, M. et al. (1995). "Fcγ receptors of phagocytes," J. Lab. Clin. Med. 126:330-341.
Donnelly, M. et al. (2001). "Fluorescent Tagging of Herpes Simplex Virus Tegument Protein VP13/14 in Virus Infection," J. Virology 75:2575-2583.
Donnelly, M. et al. (2001). "Nuclear Localization and Shuttling of Herpes Simplex Virus Tegument Protein VP13/14," J. Virology 75:2566-2574.
Doronina, V.A. et al. (2008). "Site-Specific Release of Nascent Chains from Ribosomes at a Sense Codon," Mol. Cell. Biol. 28:4227-4239.
Eshhar, Z. et al. (1993). "Immunology Specific activation and targeting of cytotoxic lymphocytes through chimeric single chains consisting of antibody-binding domains and the γ or ζ subunits of the immunoglobulin and T-cell receptors," PNAS 90:720-724.
Fellouse, F.A. et al. (2007). "High-throughput Generation of Synthetic Antibodies from Highly Functional Minimalist Phage-displayed Libraries," J. Mol. Biol. 373:924-940.
Findeis, M.A. et al. (1993). "Targeted delivery of DNA for gene therapy via receptor," Trends Biotechnol. 11:202-205.

Gazzano-Santoro, H. et al. (1997). "A non-radioactive complement-dependent cytotoxicity assay for anti-CD20 monoclonal antibody," J. Immunol. Methods 202:163-171.
Ge, H. et al. (2017). "Tumor associated CD70 expression is involved in promoting tumor migration and macrophage infiltration in GBM," International Journal of Cancer 141:1434-1444.
GenBank accession No. P32970-1, CD70 antigen, 11 total pages.
GenBank accession No. AAA53133, 4-1BB (*Homo sapiens*), 2 total pages.
GenBank accession No. NP_006130.1, T-cell specific surface glycoprotein CD28 isoform 1 precursor (*Homo sapiens*), 4 total pages.
GenBank accession No. NP_001139345.1, T-cell surface glycoprotein CD8 alpha chain isoform 1 precursor (*Homo sapiens*), 3 total pages.
GenBank accession No. NM-005018.3, *Homo sapiens* programmed cell death 1 (PDCD1), mRNA, 5 total pages.
GenBank accession No. AF414120.1, *Homo sapiens* CTLA4 (CTLA4) mRNA, complete cds, 2 total pages.
GenBank accession No. NM-002286.5, *Homo sapiens* lymphocyte activating 3 (LAG3), mRNA, 4 total pages.
GenBank accession No. JX049979.1, *Homo sapiens* T-cell immunoglobulin and mucin domain-containing protein 3 mRNA, complete cds, 2 total pages.
GenBank accession No. NM-181780.3, *Homo sapiens* B and T lymphocyte associated (BTLA), transcript variant 1, mRNA, 5 total pages.
GenBank accession No. CR541888.1, *Homo sapiens* full open reading frame cDNA clone RZPDo834D0633D for gene CD160, CD160 antigen; complete cds, without stopcodon, 2 total pages.
GenBank accession No. NM-173799.4, *Homo sapiens* T cell immunoreceptor with Ig and ITIM domains (TIGIT), mRNA, 5 total pages.
GenBank accession No. NM-022153.1, *Homo sapiens* V-set immunoregulatory receptor (VSIR), mRNA, 5 total pages.
GenBank accession No. CR542051.1, *Homo sapiens* full open reading frame cDNA clone RZPDo834C0736D for gene LAIR1, leukocyte-associated Ig-like receptor 1; complete cds, without stopcodon, 2 total pages.
GenBank accession No. AY358337.1, *Homo sapiens* clone DNA54002 SIGLEC10 (UNQ477) mRNA, complete cds, 2 total pages.
GenBank accession No. NM-001166664.1, *Homo sapiens* CD244 molecule (CD244), transcript variant 3, mRNA, 4 total pages.
Grewal, I.S. et al. (2008). "CD70 as a therapeutic target in human malignancies," Expert Opinion on Therapeutic Targets 12:341-351.
Griffith, A.D. et al. (1993). "Human anti-self antibodies with high specificity from phage display libraries," EMBO J. 12:725-734.
Guyer, R.L. et al. (1976). "Immunoglobulin binding by mouse intestinal epithelial cell receptors," J. Immunol. 117:587-593.
Harlow, E. et al. (1999). Chapter 11: Epitope mapping in Using Antibodies, a Laboratory Manual, Cold Spring Harbor Laboratory Press, Cold Spring Harbor, New York, pp. 379-405.
Hawkins, R.E. et al. (1992). "Selection of Phage Antibodies by Binding Affinity Mimicking Affinity Maturation," J. Mal. Biol. 226:889-896.
Hein, J. (1990). "Unified Approach to Alignment and Phylogenes," Methods in Enzymology 183: 626-645.
Henderson, D.J. et al. (1991). "Comparison of the effects of FK-506, cyclosporin A and rapamycin on IL-2 production," Immunol. 73:316-321.
Higgins, D.G. et al. (1989). "Fast and sensitive multiple sequence alignments on a microcomputer," CABIOS 5:151-153.
Hoogenboom, H.R. et al. (1991). "By-passing Immunisation Human Antibodies from Synthetic Repertoires of Germline $V_H$ Gene Segments Rearranged in Vitro," J. Mol. Biol. 227:381-388.
Hsu, T-A. et al. (1997). "Differential N-Glycan Patterns of Secreted and Intracellular IgG Produced in Trichoplusia ni Cells," J. Biol. Chem. 272:9062-9070.
Humphreys, D.P. et al. (1997). "Formation of dimeric Fabs in *Escherichia coli*: effect of hinge size and isotype, presence of interchain disulphide bond, Fab' expression levels, tail piece sequences and growth conditions," J. Immunol. Methods 209:193-202.
International Search Report dated May 28, 2019, for PCT Application No. PCT/US2019/016189, filed on Jan. 31, 2019, 9 pages.

(56) References Cited

OTHER PUBLICATIONS

International Search Report dated May 13, 2019, for PCT Application No. PCT/US2019/016139, filed on Jan. 31, 2019, 14 pages.
Jackson, J.R. et al. (1995). "In vitro antibody maturation—Improvement of a high affinity, neutralizing antibody against IL-1β," J. Immunol. 154:3310-3319.
Jayasena, S.D. (1999). "Aptamers: An Emerging Class of Molecules That Rival Antibodies in Diagnostics," Clin. Chem. 45:1628-1650.
Jefferis, R. et al. (1997). "Glycosylation of antibody molecules: Structural and functional significance," Chem. Immunol. Basel. Karger 65:111-128.
Jin, L. et al. (2017). "CD70, a novel target of CAR T-cell therapy for gliomas," Neuro-Oncology 20:55-65.
Johnson, K.S. et al. (1993). "Human antibody engineering," Current Opinion in Structural Biol. 3:564-571.
Jolly, D. (1994). "Viral vector systems for gene therapy," Cancer Gene Therapy 1:51-64.
Jones, P.T. et al. (1986). "Replacing the complementarity—Determining regions in a human antibody with those from a mouse," Nature 321:522-525.
Kaplitt, M.G. et al. (1994). "Long-term gene expression and phenotypic correction using adeno-associated virus vectors in the mammalian brain," Nature Genetics 6:148-154.
Kim et al. "Localization of the site of the murine IgG1 molecule that is involved in binding to the murine intestinal Fc receptor," J. Immunol. 24:2429-2434.
Kimura, O. et al. (1994). "Retroviral delivery of DNA into the livers of transgenic mice bearing premalignant and malignant hepatocellular carcinomas," Human Gene Therapy 5:845-852.
Kohler, C. et al. (1975). "Continuous cultures of fused cells secreting antibody of predefined specificity," Nature 256:495-497.
Liu, J. et al. (1992). "Inhibition of T Cell Signaling by Immunophilin-Ligand Complexes Correlates with Loss of Calcineurin Phosphatase Activity," Biochem. 31:3896-3901.
LoBuglio, A.F. et al. (1989). "Mouse/human chimeric monoclonal antibody in man: Kinetics and immune response," PNAS 86:4220-4224.
Lonberg, N. et al. (1995). "Human antibodies from transgenic mice," Intern. Rev. Immunol 13:65-93.
Maccallum, R.M. et al. (1996). "Antibody-antigen Interactions: Contact Analysis and Binding Site Topography," J. Mol. Biol. 262:732-745.
Makabe, K. et al. (2008). "Thermodynamic Consequences of Mutations in Vernier Zone Residues of a Humanized Anti-human Epidermal Growth," Journal of Biological Chemistry 283:1156-1166.
Marks, J.D. et al. (1991). "By-passing Immunization Human Antibodies from V-gene Libraries Displayed on Phage," J. Mol. Biol. 222:581-597.
Marks, J.D. et al. (1992). "By-passing immunization: Building high affinity human antibodies by chain shuffling," Bio/Technol. 10:779-783.
Martyniszyn, A. et al. (2017). "CD20-CD19 Bispecific CAR T Cells for the Treatment of B-Cell Malignancies," Human Gene Therapy 28:1147-1157.
McCafferty, J. et al. (1990). "Phage antibodies: filamentous phage displaying antibody variable domains," Nature 348:552-554.
McEarchern J.A. et al. (2007). "Engineered anti-CD70 antibody with multiple effector functions exhibits in vitro and in vivo antitumor activities," Blood 109:1185-1192.
Millstein, C. et al. (1983). "Hybrid hybridomas and their use in immunohistochemistry," Nature 305:537-539.
Morrison, S.L. et al. (1984). "Chimeric human antibody molecules: Mouse antigen-binding domains with human constant region domains," PNAS 81:6851-6855.
Myers, E.W. et al. (1988). "Optimal alignments in linear space," CABIOS 4:11-17.
Myszka, D.G. (1999). "Improving biosensor analysis," J Mol. Recognit. 12:279-284.
Niculescu-Duvaz, I. et al. (1997). "Antibody-directed enzyme prodrug therapy (ADEPT): a review," Adv. Drug Del. Rev. 26:151-172.
Payne, G. (2003). "Progress in immunoconjugate cancer therapeutics," Cancer Cell 3:207-212.
Peeters, K. et al. (2001). "Production of antibodies and antibody fragments in plants," Vaccine 19:2756-2761.
Philip, R. et al. (1994). "Efficient and Sustained Gene Expression in Primary T Lymphocytes and Primary and Cultured Tumor Cells Mediated by Adena-Associated Virus Plasmid DNA Complexed to Cationic Liposomes," Mol. Cell Biol. 14:2411-2418.
Pollock, D.P. et al. (1999). "Transgenic milk as a method for the production of recombinant antibodies," J Immunol Methods 231:147-157.
Ravetch, J.V. et al. (1991). "Fc receptors," Kinet, Ann. Rev. Immunol. 9:457-492.
Riechmann, L. et al. (1988). "Reshaping human antibodies for therapy," Nature 332:323-327.
Robinson, D.F. (1971). "Comparison of Labeled Trees with Valency Three," J. Comb. Theory 11:105-119.
Rosenberg, S.A. et al. (2008). "Adoptive cell transfer: a clinical path to effective cancer Immunotherapy," Nature Reviews Cancer 8:299-308.
Sadelain, M. et al. (2009). "The promise and potential pitfalls of chimeric antigen receptors," Curr. Opin. Immunol, 21:215-223.
Sadelain, M. et al. (2013). "The Basic Principles of Chimeric Antigen Receptor Design," Cancer Discovery 3:388-398.
Saitou, N. et al. (1987). "The neighbor-joining method: A new method for reconstructing phylogenetic trees," Mol. Biol. Evol. 4:406-425.
Schier, R. et al. (1995). "Identification of functional and structural amino-acid residues by parsimonious mutagenesis," Gene 169:147-155.
Shaffer, D.R. et al. (2011). "T cells redirected against CD70 for the immunotherapy of CD70-positive malignancies," Blood 117:4304-4314.
Shaw, D.R. et al. (1987). "Characterization of a mouse/human chimeric monoclonal antibody (17-1A) to a colon cancer tumor-associated antigen," J Immunol. 138:4534-4538.
Sheets, M.D. et al. (1998). "Efficient construction of a large nonimmune phage antibody library: The production of high-affinity human single-chain antibodies to protein antigens," PNAS 95:6157-6162.
Simmons, J.K. et al. (2015). "Animal Models of Bone Metastasis," Veterinary Pathology 52:827-841.
Suresh, M.R. et al. (1986). "Biospecific monoclonal antibodies from hybrid hybridomas," Methods in Enzymology 121:210-228.
Syrigos, K.N. et al. (1999). "Antibody Directed Enzyme Prodrug Therapy (ADEPT): A Review of the Experimental and Clinical Considerations," Anticancer Research 19:605-614.
Tiller, T. et al. (2008). "Efficient generation of monoclonal antibodies from single human B cells by single cell RT-PCR and expression vector cloning," J. Immunol. Methods 329:112-124.
Trail, P.A. et al. (2003). "Monoclonal antibody drug immunoconjugates for targeted treatment of cancer," Cancer Immunol. Immunother. 52:328-337.
Umana, P. et al. (1999). "Engineered glycoforms of an antineuroblastoma IgG1 with optimized antibody-dependent cellular cytotoxic activity," Mature Biotech. 17:176-180.
Vaughan, T.J. et al. (1996). "Human Antibodies with Sub-nanomolar Affinities Isolated from a Large Non-immunized Phage Display Library," Nature Biotechnol. 14:309-314.
Verhoeyen, M. et al. (1988). "Reshaping human antibodies: Grafting an antilysozyme activity," Science 239:1534-1536.
Wang, Q.J. et al. (2017). "Preclinical Evaluation of Chimeric Antigen Receptors Targeting CD70-Expressing Cancers," Clinical Cancer Research 23:2267-2276.
Ward, E.S. et al. (1989). "Binding activities of a repertoire of single immunoglobulin variable domains secreted from *Escherichia coli*," Nature 341:544-546.
Waterhouse, P. et al. (1993). "Combinatorial infection and in vivo recombination: a strategy for making large phage antibody repertoires," Nucl. Acids Res. 21:2265-2266.
Whitlow, M. et al. (1993). "An improved linker for single-chain Fv with reduced aggregation and enhanced proteolytic stability," Protein Eng. 6:989-995.

(56) References Cited

OTHER PUBLICATIONS

Wilbur, W.J. et al. (1983). "Rapid similarity searches of nucleic acid and protein data banks," PNAS 80:726-730.
Winter, G. et al. (1991). "Man-made antibodies," Nature 349:293-299.
Winter, G. et al. (1994). "Making Antibodies by Phage Display Technology," Annu. Rev. Immunol. 12:433-455.
Wittwer, A.J. et al. (1990). "Glycosylation at Asn-184 Inhibits the Conversion of Single-Chain to Two-Chain Tissue-Type Plasminogen Activator by Plasmin," Biochem. 29:4175-4180.
Woffendin, C. et al. (1994). "Nonviral and viral delivery of a human immunodeficiency virus protective gene into primary human T cells," PNAS 91:11581-11585.
Wright, A. et al. (1997). "Effect of glycosylation on antibody function: implications for genetic engineering," Tibtech 15:26-32.
Written Opinion of the International Searching Authority dated May 28, 2019, for PCT Application No. PCT/US2019/016189, filed on Jan. 31, 2019, 11 pages.
Written Opinion of the International Searching Authority dated May 13, 2019, for PCT Application No. PCT/US2019/016139, filed on Jan. 31, 2019, 14 pages.
Wu, G.Y. et al. (1988). "Receptor-mediated Gene Delivery and Expression in Vivo," J. Biol. Chem. 263:14621-14624.
Wu, C.H. et al. (1989). "Targeting Genes: Delivery and Persistent Expression of a Foreign Gene Driven by Mammalian Regulatory Elements in Vivo," J. Biol. Chem. 264:16985-16987.
Wu, G.Y. et al. (1991). "Receptor-mediated gene delivery in Vivo," J. Biol. Chem. 266:14338-14342.
Wu, G.Y. et al. (1994). "Incorporation of Adenovirus into a Ligand-based DNA Carrier System Results in Retention of Original Receptor Specificity and Enhances Targeted Gene Expression," J. Biol. Chem. 269:11542-11546.
Wyss, D.F. et al. (1996). "The structural role of sugars in glycoproteins," Current Opin. Biotech. 7:409-416.
Yelton, D.E. et al. (1995). "Affinity maturation of the BR96 anti-carcinoma antibody by codon-based mutagenesis," J. Immunol. 155:1994-2004.
Zarrabi, K. et al. (2017). "New treatment options for metastatic renal cell carcinoma with prior anti-angiogenesis therapy," Journal of Hematology and Oncology 10:38, 12 total pages.
Zenke, M. et al. (1990). "Receptor-mediated endocytosis of transferrin-polycation conjugates: An efficient way to introduce DNA into hematopoietic cells," PNAS 87:3655-3659.

* cited by examiner

ANTIBODIES SPECIFIC FOR CD70 AND THEIR USES

CROSS-REFERENCE TO RELATED APPLICATIONS

This application claims priority to U.S. Provisional Patent Appl. No. 62/641,873, filed Mar. 12, 2018, and U.S. Provisional Patent Appl. No. 62/625,019, filed Feb. 1, 2018, each of which is incorporated herein by reference in its entirety.

REFERENCE TO SEQUENCE LISTING

This application is being filed electronically via EFS-Web and includes an electronically submitted sequence listing in .txt format. The .txt file contains a sequence listing entitled "ALGN-015_02 US_SL.txt" created on Jan. 30, 2019, and having a size of 223 kilobytes. The sequence listing contained in this .txt file is part of the specification and is incorporated herein by reference in its entirety.

FIELD

The present invention relates to antibodies, e.g., full length antibodies or antigen binding fragments thereof, that specifically bind to Cluster of Differentiation 70 (CD70). The invention further relates to heteromultimeric antibodies (e.g., bispecific antibodies) comprising CD70 antibody on one arm. Compositions comprising the CD70 antibodies, methods for producing and purifying such antibodies, and their use in diagnostics and therapeutics are also provided.

BACKGROUND

Renal Cell Carcinoma (RCC) is a cancer that originates in the renal cortex and accounts for about 90% of cancers in the kidney. Based on histology, RCC can be classified into several sub-types, of which Clear Cell Renal Cell Carcinoma (ccRCC) is the most common and leads to the most deaths. Each year, over 320,000 cases of RCC are reported worldwide leading to roughly 140,000 deaths. The incidence of RCC has risen steadily over the last 10 years and accounts for 2-3% of all adult malignancies. Patients with early stage localized tumors can opt for surgical resection; however, localized disease can undergo early hematogenous dissemination leading to metastasis. Sites of early metastases include lungs, lymph nodes, liver, bone, and brain; less commonly the adrenal glands, and the contralateral kidney. Patients with advanced disease face high morbidity rates with a 5-year median survival rate of 53% for stage III disease and only 8% for metastatic disease. Current first-line treatment options for advanced disease include small molecule Tyrosine Kinase Inhibitors (TKIs) such as sunitinib and pazopanib that target Vascular Endothelial Growth Factor (VEGF) receptor, monoclonal antibody targeting VEGF such as bevacizumab, mammalian target of Rapamycin (mTOR) inhibitor temsirolimus, as well as high dose IL-2. Although these VEGF-targeted therapies have improved over-all survival, long-term drug resistance leads to disease relapse and treatment for advanced disease still remains an unmet need (see, e.g., Zarrabi, K. et al., Journal of Hematology and Oncology, 10:38 (2017)).

Cluster of Differentiation 70 (CD70, CD27LG or TNFSF7) is a member of the tumor necrosis factor (TNF) superfamily and the ligand for CD27, a TNF superfamily receptor. The transient interaction between CD27 and CD70 provides T cell costimulation complementary to that provided by CD28. CD70 is expressed on hematological cancers such as Non-Hodgkin's Lymphoma and Hodgkin's disease as well as on solid tumors such as Glioblastoma and Renal Cell Carcinoma; with its expression on ccRCC being nearly uniform (see e.g., Grewal I., et al., Expert Opinion on Therapeutic Targets, 12(3): 341-351 (2008)).

CD70 bispecific antibody in the form of T-cell engaging bispecific approach has been developed recently. However, a limitation of many bispecific formats is that they are of small molecular weight, and of short half-life, thus requiring continuous infusion. Accordingly, there remains a need for antibodies (e.g., monospecific or bispecific) treating cancer where CD70 is expressed and in particular mRCC with improved efficacy and safety profile, and suitable for use with human patients.

SUMMARY

The invention disclosed herein is directed to antibodies (e.g., monospecific or bispecific antibodies) that specifically bind to Cluster of Differentiation 70 (CD70). In some embodiments, the CD70 antibodies as described herein in the full-length bispecific format have longer half-life, minimized Fc-interaction, and minimized non-specific cytokine release in vivo via interaction with immune cells.

Accordingly, in one aspect, the invention provides an isolated antibody which specifically binds to CD70, wherein the antibody comprises (a) a heavy chain variable (VH) region comprising (i) a VH complementarity determining region one (CDR1) comprising the sequence shown in SEQ ID NO: 49, 50, 51, 55, 56, 57, 61, 62, 63, 67, 68, 69, 73, 74, 75, 79, 80, 81, 85, 86, 87, 91, 92, 93, 97, 98, 99, 103, 104, 105, 109, 110, 111, 115, 116, 117, 121, 122, 123, 127, 128, 129, 133, 134, 135, 139, 140, 141, 145, 146, 147, 151, 152, 153, 157, 158, 159, 163, 164, 165, 169, 170, 171, 175, 176, 177, 181, 182, 183, 187, 188, 189, 332, 333, 334, 338, 339, 340, 344, 345, 346, 350, 351, 352, 356, 357, 358, 362, 363, 364, 368, 369, 370, 374, 375, 376, 380, 381, 382, 386, 387, 388, 392, 393, 394, 398, 399, 400, 404, 405, 406, 410, 411, 412, 416, 437, 418, 422, 423, 424, 428, 429, 430, 434, 435, 436, 440, 441, 442, 446, 447, 448, 452, 453, 454, 458, 459 or 460; (ii) a VH CDR2 comprising the sequence shown in SEQ ID NO: 52, 53, 58, 59, 64, 65, 70, 71, 76, 77, 82, 83, 88, 89, 94, 95, 100, 101, 106, 107, 112, 113, 118, 119, 124, 125, 130, 131, 136, 137, 142, 143, 148, 149, 154, 155, 160, 161, 166, 167, 172, 173, 178, 179, 184, 185, 190, 191, 335, 336, 341, 342, 347, 348, 353, 354, 359, 360, 365, 366, 371, 372, 377, 378, 383, 384, 389, 390, 395, 396, 401, 402, 407, 408, 413, 414, 419, 420, 425, 426, 431, 432, 437, 438, 443, 444, 449, 450, 455, 456, 461 or 462; and iii) a VH CDR3 comprising the sequence shown in SEQ ID NO: 54, 60, 66, 72, 78, 84, 90, 96, 102, 108, 114, 120, 126, 132, 138, 144, 150, 156, 162, 168, 174, 180, 186, 192, 337, 343, 349, 355, 361, 367, 373, 379, 385, 391, 397, 403, 409, 415, 421, 427, 433, 439, 445, 451, 457 or 463; or a light chain variable (VL) region comprising (i) a VL CDR1 comprising the sequence shown in SEQ ID NO: 193, 196, 199, 202, 205, 208, 211, 214, 217, 220, 223, 226, 229, 232, 235, 238, 241, 244, 247, 250, 253, 256, 259, 262, 464, 467, 470, 473, 476, 479, 482, 485, 488, 491, 494, 497, 500, 503, 506, 509, 512, 515, 518, 521, 524 or 527; (ii) a VL CDR2 comprising the sequence shown in SEQ ID NO: 194, 197, 200, 203, 206, 209, 212, 215, 218, 221, 224, 227, 230, 233, 236, 239, 242, 245, 248, 251, 254, 257, 260, 263, 465, 468, 471, 474, 477, 480, 483, 486, 489, 492, 495, 498, 501, 504, 507, 510, 513, 516, 519, 522, 525 or 528; and (iii) a VL CDR3 comprising the sequence shown in SEQ ID NO: 195, 198, 201, 204, 207, 210, 213, 216, 219, 222, 225, 228, 231, 234, 237, 240, 243, 246, 249, 252, 255, 258, 261, 264, 466, 469, 472, 475, 478, 481, 484, 487, 490, 493, 496, 499, 502, 505, 508, 511, 514, 517, 520, 523, 526 or 529.

In another aspect, provided is an isolated antibody which specifically binds to CD70, wherein the antibody comprises: a VH region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 38, 40, 42, 44, 46, 48, 289, 291, 293, 295, 297, 299, 301, 303, 305, 307, 309, 311, 313, 315, 317, 319, 321, 323, 325, 327, 329 or 331; or a VL region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 37, 39, 41, 43, 45, 47, 288, 290, 292, 294, 296, 298, 300, 302, 304, 306, 308, 310, 312, 314, 316, 318, 320, 322, 324, 326, 328 or 330. In some embodiments, the VH region as described herein comprises a variant with one or several conservative amino acid substitutions in residues that are not within a CDR or the VL region as described herein comprises a variant with one or several amino acid substitutions in amino acids that are not within a CDR. For example, in some embodiments, the VH or VL region can comprise an amino acid sequence described above or a variant thereof with no more than 10, 9, 8, 7, 6, 5, 4, 3, 2, or 1 conservative substitutions in residues that are not within a CDR.

In some embodiments, provided is an isolated antibody which specifically binds to CD70, wherein the antibody comprises: a VH region comprising the sequence shown in SEQ ID NO: 18; or a VL region comprising the sequence shown in SEQ ID NO: 17.

In some embodiments, provided is an antibody which specifically binds to CD70 and competes with an isolated antibody provided herein which specifically binds to CD70.

In another aspect, provided is a bispecific antibody wherein the bispecific antibody is a full-length antibody, comprising a first antibody variable domain of the bispecific antibody specifically binding to a target antigen (e.g., CD70), and comprising a second antibody variable domain of the bispecific antibody capable of recruiting the activity of a human immune effector cell by specifically binding to an effector antigen (e.g., Cluster of differentiation 3 (CD3)) located on the human immune effector cell. In some embodiments, the first antibody variable domain comprises a heavy chain variable (VH) region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 38, 40, 42, 44, 46, 48, 289, 291, 293, 295, 297, 299, 301, 303, 305, 307, 309, 311, 313, 315, 317, 319, 321, 323, 325, 327, 329 or 331; or a light chain variable (VL) region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 37, 39, 41, 43, 45, 47, 288, 290, 292, 294, 296, 298, 300, 302, 304, 306, 308, 310, 312, 314, 316, 318, 320, 322, 324, 326, 328 or 330. In some embodiments, the first antibody variable domain comprises (a) a heavy chain variable (VH) region comprising (i) a VH complementarity determining region one (CDR1) comprising the sequence shown in SEQ ID NO: 49, 50, 51, 55, 56, 57, 61, 62, 63, 67, 68, 69, 73, 74, 75, 79, 80, 81, 85, 86, 87, 91, 92, 93, 97, 98, 99, 103, 104, 105, 109, 110, 111, 115, 116, 117, 121, 122, 123, 127, 128, 129, 133, 134, 135, 139, 140, 141, 145, 146, 147, 151, 152, 153, 157, 158, 159, 163, 164, 165, 169, 170, 171, 175, 176, 177, 181, 182, 183, 187, 188, 189, 332, 333, 334, 338, 339, 340, 344, 345, 346, 350, 351, 352, 356, 357, 358, 362, 363, 364, 368, 369, 370, 374, 375, 376, 380, 381, 382, 386, 387, 388, 392, 393, 394, 398, 399, 400, 404, 405, 406, 410, 411, 412, 416, 437, 418, 422, 423, 424, 428, 429, 430, 434, 435, 436, 440, 441, 442, 446, 447, 448, 452, 453, 454, 458, 459 or 460; (ii) a VH CDR2 comprising the sequence shown in SEQ ID NO: 52, 53, 58, 59, 64, 65, 70, 71, 76, 77, 82, 83, 88, 89, 94, 95, 100, 101, 106, 107, 112, 113, 118, 119, 124, 125, 130, 131, 136, 137, 142, 143, 148, 149, 154, 155, 160, 161, 166, 167, 172, 173, 178, 179, 184, 185, 190, 191, 335, 336, 341, 342, 347, 348, 353, 354, 359, 360, 365, 366, 371, 372, 377, 378, 383, 384, 389, 390, 395, 396, 401, 402, 407, 408, 413, 414, 419, 420, 425, 426, 431, 432, 437, 438, 443, 444, 449, 450, 455, 456, 461 or 462; and iii) a VH CDR3 comprising the sequence shown in SEQ ID NO: 54, 60, 66, 72, 78, 84, 90, 96, 102, 108, 114, 120, 126, 132, 138, 144, 150, 156, 162, 168, 174, 180, 186, 192, 337, 343, 349, 355, 361, 367, 373, 379, 385, 391, 397, 403, 409, 415, 421, 427, 433, 439, 445, 451, 457 or 463; or (b) a light chain variable (VL) region comprising (i) a VL CDR1 comprising the sequence shown in SEQ ID NO: 193, 196, 199, 202, 205, 208, 211, 214, 217, 220, 223, 226, 229, 232, 235, 238, 241, 244, 247, 250, 253, 256, 259, 262, 464, 467, 470, 473, 476, 479, 482, 485, 488, 491, 494, 497, 500, 503, 506, 509, 512, 515, 518, 521, 524 or 527; (ii) a VL CDR2 comprising the sequence shown in SEQ ID NO: 194, 197, 200, 203, 206, 209, 212, 215, 218, 221, 224, 227, 230, 233, 236, 239, 242, 245, 248, 251, 254, 257, 260, 263, 465, 468, 471, 474, 477, 480, 483, 486, 489, 492, 495, 498, 501, 504, 507, 510, 513, 516, 519, 522, 525 or 528; and (iii) a VL CDR3 comprising the sequence shown in SEQ ID NO: 195, 198, 201, 204, 207, 210, 213, 216, 219, 222, 225, 228, 231, 234, 237, 240, 243, 246, 249, 252, 255, 258, 261, 264, 466, 469, 472, 475, 478, 481, 484, 487, 490, 493, 496, 499, 502, 505, 508, 511, 514, 517, 520, 523, 526 or 529.

In some embodiments, the second antibody variable domain comprises the VH or VL region specific against CD3. For example, the second antibody variable domain comprises a heavy chain variable (VH) region comprising a VH CDR1, VH CDR2, and VH CDR3 of the VH sequence shown in SEQ ID NO:266; or a light chain variable (VL) region comprising a VL CDR1, VL CDR2, and VL CDR3 of the VL sequence shown in SEQ ID NO: 265. In some embodiments, the second antibody variable domain comprises (a) a VH region comprising (i) a VH CDR1 comprising the sequence shown in SEQ ID NO: 267, 268, or 269; (ii) a VH CDR2 comprising the sequence shown in SEQ ID NO: 270 or 271; and iii) a VH CDR3 comprising the sequence shown in SEQ ID NO: 272; or a VL region comprising (i) a VL CDR1 comprising the sequence shown in SEQ ID NO: 273; (ii) a VL CDR2 comprising the sequence shown in SEQ ID NO: 274; and (iii) a VL CDR3 comprising the sequence shown in SEQ ID NO: 275.

In some embodiments, the antibodies described herein comprise a constant region. In some embodiments, the antibodies described herein are of the human IgG1, IgG2 or IgG2Δa, IgG3, or IgG4 subclass. In some embodiments, the antibodies described herein comprise a glycosylated constant region. In some embodiments, the antibodies described herein comprise a constant region having decreased binding affinity to one or more human Fc gamma receptor(s).

In some embodiments, both the first and the second antibody variable domains of the bispecific antibody comprise amino acid modifications at positions 223, 225, and 228 (e.g., (C223E or C223R), (E225R), and (P228E or P228R)) in the hinge region and at position 409 or 368 (e.g., K409R or L368E (EU numbering scheme)) in the CH3 region of human IgG2 (SEQ ID NO: 279).

In some embodiments, both the first and the second antibody variable domains of the bispecific antibody comprise amino acid modifications at position 265 (e.g., D265A) of the human IgG2.

In some embodiments, both the first and the second antibody variable domains of the bispecific antibody comprise amino acid modifications at one or more of positions 265 (e.g., D265A), 330 (e.g., A330S), and 331 (e.g., P331S) of the human IgG2. In some embodiments, both the first and the second antibody variable domains of the bispecific antibody comprise amino acid modifications at each of positions 265 (e.g., D265A), 330 (e.g., A330S), and 331 (e.g., P331S) of the human IgG2.

In other embodiments, the invention provides pharmaceutical compositions comprising any of the antibodies described herein.

The invention also provides cell lines that recombinantly produce any of the antibodies described herein.

The invention also provides nucleic acids encoding any of the antibodies described herein. The invention also provides nucleic acids encoding a heavy chain variable region or a light chain variable region of any of the antibodies described herein.

The invention also provides a host cell comprising a nucleic acid or vector provided herein. Also provided is a method of producing an antibody (e.g. monospecific or bispecific) provided herein, comprising culturing a host cell provided herein under conditions that result in production of the antibody, and isolating the antibody from the host cell or culture.

The invention also provides kits comprising an effective amount of any of the antibodies or antibody conjugates described herein.

Also provided is an antibody or bispecific antibody provided herein for use as a medicament.

The invention also provides methods of treating subjects in need thereof comprising providing the isolated antibodies or bispecific antibodies described herein, and administering said antibodies to said subject.

Also provided are methods of treating a condition associated with malignant cells expressing CD70 in a subject comprising administering to a subject in need thereof an effective amount of a pharmaceutical composition comprising the antibodies as described herein. In some embodiments, the condition is a cancer. In some embodiments, the cancer is an CD70 related cancer (e.g., any cancer with CD70 expression) selected from the group consisting of Renal Cell Carcinoma, Glioblastoma, glioma such as low grade glioma, Non-Hodgkin's Lymphoma (NHL), Hodgkin's Disease (HD), Waldenstrom's macroglobulinemia, Acute Myeloid Leukemia, Multiple Myeloma, diffuse large-cell lymphoma, follicular lymphoma or Non-Small Cell Lung Cancer.

In another aspect, the invention provides a method of inhibiting tumor growth or progression in a subject who has malignant cells expressing CD70, comprising administering to the subject in need thereof an effective amount of a pharmaceutical composition comprising the isolated antibodies or bispecific antibodies, as described herein.

In another aspect, the invention provides a method of inhibiting metastasis of malignant cells expressing CD70 in a subject, comprising administering to the subject in need thereof an effective amount of the pharmaceutical composition comprising the isolated antibodies or bispecific antibodies, as described herein.

In another aspect, the invention provides a method inducing tumor regression in a subject who has malignant cells expressing CD70, comprising administering to the subject in need thereof an effective amount of the pharmaceutical composition of a pharmaceutical composition comprising the isolated antibodies or bispecific antibodies, as described herein.

DETAILED DESCRIPTION

The invention disclosed herein provides antibodies (e.g., monospecific or bispecific) that specifically bind to CD70 (e.g., human CD70). The invention also provides polynucleotides encoding these antibodies, compositions comprising these antibodies, and methods of making and using these antibodies. The invention also provides methods for treating a condition associated with CD70-mediated pathologies in a subject, such as cancer. In particular, the inventors of the present invention have discovered that the CD70 antibodies as described herein in the full-length bispecific format have longer half-life, minimized Fc-interaction, and minimized non-specific cytokine release in vivo via interaction with the immune cells.

General Techniques

The practice of the present invention will employ, unless otherwise indicated, conventional techniques of molecular biology (including recombinant techniques), microbiology, cell biology, biochemistry, immunology, virology, monoclonal antibody generation and engineering, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen binding fragments thereof (such as Fab, Fab', F(ab')2, Fv), single chain (ScFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., CD70). Antigen binding functions of an antibody can be performed by fragments of an intact antibody. Examples of binding fragments encompassed within the term "antigen binding fragment" of an antibody include Fab; Fab'; F(ab')2; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody or a polypeptide that "preferentially binds" or "specifically binds" (used interchangeably herein) to a target (e.g., CD70 protein) is a term well understood in the art, and methods to determine such specific or preferential binding are also well known in the art. A molecule is said to exhibit "specific binding" or "preferential binding" if it reacts or associates more frequently, more rapidly, with greater duration or with greater affinity with a particular cell or substance than it does with alternative cells or substances. An antibody "specifically binds" or "preferentially binds" to a target if it binds with greater affinity, avidity, more readily, or with greater duration than it binds to other substances. For example, an antibody that specifically or preferentially binds to an CD70 epitope is an antibody that binds this epitope with greater affinity, avidity, more readily, or with greater duration than it binds to other CD70 epitopes or non-CD70 epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen binding subsequences of antibodies) that contain minimal sequence derived from non-human immunoglobulin.

Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length. For example, the chain may be relatively short (e.g., 10-100 amino acids), or longer. The chain may be linear or branched, it may comprise modified amino acids, or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "monospecific antibody" comprises two identical antigen binding sites per molecule (e.g. IgG) such that the two binding sites bind identical epitope on the antigen.

Thus, they compete with each other on binding to one antigen molecule. Most antibodies found in nature are monospecific. In some instances, a monospecific antibody can also be a monovalent antibody (e.g. Fab)

A "bivalent antibody" comprises two antigen binding sites per molecule (e.g., IgG). In some instances, the two binding sites have the same antigen specificities. However, bivalent antibodies may be bispecific.

A "bispecific" or "dual-specific" is a hybrid antibody having two different antigen binding sites. The two antigen binding sites of a bispecific antibody bind to two different epitopes, which may reside on the same or different protein targets.

A "bifunctional" is antibody is an antibody having identical antigen binding sites (i.e., identical amino acid sequences) in the two arms but each binding site can recognize two different antigens.

A "heteromultimer", "heteromultimeric complex", or "heteromultimeric polypeptide" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where polypeptides in addition to the first and second polypeptide are present.

A "heterodimer," "heterodimeric protein," "heterodimeric complex," or "heteromultimeric polypeptide" is a molecule comprising a first polypeptide and a second polypeptide, wherein the second polypeptide differs in amino acid sequence from the first polypeptide by at least one amino acid residue.

The "hinge region," "hinge sequence", and variations thereof, as used herein, includes the meaning known in the art, which is illustrated in, for example, Janeway et al., ImmunoBiology: the immune system in health and disease, (Elsevier Science Ltd., NY) (4th ed., 1999); Bloom et al., Protein Science (1997), 6:407-415; Humphreys et al., J. Immunol. Methods (1997), 209:193-202.

The "immunoglobulin-like hinge region," "immunoglobulin-like hinge sequence," and variations thereof, as used herein, refer to the hinge region and hinge sequence of an immunoglobulin-like or an antibody-like molecule (e.g., immunoadhesins). In some embodiments, the immunoglobulin-like hinge region can be from or derived from any IgG1, IgG2, IgG3, or IgG4 subtype, or from IgA, IgE, IgD or IgM, including chimeric forms thereof, e.g., a chimeric IgG1/2 hinge region.

The term "immune effector cell" or "effector cell as used herein refers to a cell within the natural repertoire of cells in the human immune system which can be activated to affect the viability of a target cell. The viability of a target cell can include cell survival, proliferation, or ability to interact with other cells.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("am idate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art, a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing or cross-competing antibodies are encompassed and can be useful for the methods disclosed herein.

A "functional Fc region" possesses at least one effector function of a native sequence Fc region. Exemplary "effector functions" include C1q binding; complement dependent cytotoxicity; Fc receptor binding; antibody-dependent cell-mediated cytotoxicity; phagocytosis; down-regulation of cell surface receptors (e.g. B cell receptor), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, e.g. from about one to about ten amino acid substitutions, and preferably, from about one to about five amino acid substitutions in a native sequence Fc region or in the Fc region of the parent polypeptide. The variant Fc region herein will preferably possess at least about 80% sequence identity with a native sequence Fc region or with an Fc region of a parent polypeptide, and most preferably, at least about 90% sequence identity therewith, more preferably, at least about 95%, at least about 96%, at least about 97%, at least about 98%, at least about 99% sequence identity therewith.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202: 163 (1996), may be performed.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of CD70 expressing tumor, remission of an CD70 associated disease (e.g., cancer), decreasing symptoms resulting from an CD70 associated disease (e.g., cancer), increasing the quality of life of those suffering from an CD70 associated disease (e.g., cancer), decreasing the dose of other medications required to treat an CD70 associated disease (e.g., cancer), delaying the progression of an CD70 associated disease (e.g., cancer), curing an CD70 associated disease (e.g., cancer), or prolong survival of patients having an CD70 associated disease (e.g., cancer).

"Ameliorating" means a lessening or improvement of one or more symptoms as compared to not administering an CD70 antibody (monospecific or bispecific). "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological or behavioral symptoms of the disease, its complications and intermediate pathological phenotypes presenting during development of the disease. For therapeutic use, beneficial or desired results include clinical results such as reducing incidence or amelioration of one or more symptoms of various CD70 associated diseases or conditions (such as for example multiple myeloma), decreasing the dose of other medications required to treat the disease, enhancing the effect of another medication, or delaying the progression of the CD70 associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 21st Ed. Mack Publishing, 2005).

The term "acyl donor glutamine-containing tag" or "glutamine tag" as used herein refers to a polypeptide or a protein containing one or more Gln residue(s) that acts as a transglutaminase amine acceptor. See, e.g., WO2012059882 and WO2015015448.

The term "$k_{on}$" or "$k_a$", as used herein, refers to the rate constant for association of an antibody to an antigen. Specifically, the rate constants ($k_{on}/k_a$ and $k_{off}/k_d$) and equilibrium dissociation constants are measured using whole antibody (i.e. bivalent) and monomeric CD70 proteins (e.g., Histidine-tagged CD70 fusion protein).

The term "$k_{off}$" or "$k_d$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

It is understood that wherever embodiments are described herein with the language "comprising," otherwise analogous embodiments described in terms of "consisting of" or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the present invention. The materials, methods, and examples are illustrative only and not intended to be limiting.

CD70 Antibodies and Methods of Making Thereof

The present invention provides an antibody that binds to CD70 [e.g., human CD70 (e.g., accession number: NP_004110 or SEQ ID NO: 235)] and characterized by any one or more of the following characteristics: (a) treat, prevent, ameliorate one or more symptoms of a condition associated with malignant cells expressing CD70 in a subject (e.g., cancer such as AML); (b) inhibit tumor growth or progression in a subject (who has a malignant tumor expressing CD70); (c) inhibit metastasis of cancer (malignant) cells expressing CD70 in a subject (who has one or more malignant cells expressing CD70); (d) induce regression (e.g., long-term regression) of a tumor expressing CD70; (e) exert cytotoxic activity in malignant cells expressing CD70; (f) block CD70 interaction with other yet to be identified factors; or (g) induce bystander effect that kill or inhibit growth of non-CD70 expressing malignant cells in the vicinity.

In one aspect, provided is an isolated antibody which specifically binds to CD70, wherein the antibody comprises (a) a heavy chain variable (VH) region comprising (i) a VH complementarity determining region one (CDR1) comprising the sequence shown in 49, 50, 51, 55, 56, 57, 61, 62, 63, 67, 68, 69, 73, 74, 75, 79, 80, 81, 85, 86, 87, 91, 92, 93, 97, 98, 99, 103, 104, 105, 109, 110, 111, 115, 116, 117, 121, 122, 123, 127, 128, 129, 133, 134, 135, 139, 140, 141, 145, 146, 147, 151, 152, 153, 157, 158, 159, 163, 164, 165, 169, 170, 171, 175, 176, 177, 181, 182, 183, 187, 188, 189, 332, 333, 334, 338, 339, 340, 344, 345, 346, 350, 351, 352, 356, 357, 358, 362, 363, 364, 368, 369, 370, 374, 375, 376, 380, 381, 382, 386, 387, 388, 392, 393, 394, 398, 399, 400, 404, 405, 406, 410, 411, 412, 416, 437, 418, 422, 423, 424, 428, 429, 430, 434, 435, 436, 440, 441, 442, 446, 447, 448, 452, 453, 454, 458, 459 or 460; (ii) a VH CDR2 comprising the sequence shown in SEQ ID NO: 52, 53, 58, 59, 64, 65, 70, 71, 76, 77, 82, 83, 88, 89, 94, 95, 100, 101, 106, 107, 112, 113, 118, 119, 124, 125, 130, 131, 136, 137, 142, 143, 148, 149, 154, 155, 160, 161, 166, 167, 172, 173, 178, 179, 184, 185, 190, 191, 335, 336, 341, 342, 347, 348, 353, 354, 359, 360, 365, 366, 371, 372, 377, 378, 383, 384, 389, 390, 395, 396, 401, 402, 407, 408, 413, 414, 419, 420, 425, 426, 431, 432, 437, 438, 443, 444, 449, 450, 455, 456, 461 or 462; and iii) a VH CDR3 comprising the sequence shown in SEQ ID NO: 54, 60, 66, 72, 78, 84, 90, 96, 102, 108, 114, 120, 126, 132, 138, 144, 150, 156, 162, 168, 174, 180, 186, 192, 337, 343, 349, 355, 361, 367, 373, 379, 385, 391, 397, 403, 409, 415, 421, 427, 433, 439, 445, 451, 457 or 463; or a light chain variable (VL) region comprising (i) a VL CDR1 comprising the sequence shown in SEQ ID NO: 193, 196, 199, 202, 205, 208, 211, 214, 217, 220, 223, 226, 229, 232, 235, 238, 241, 244, 247, 250, 253, 256, 259, 262, 464, 467, 470, 473, 476, 479, 482, 485, 488, 491, 494, 497, 500, 503, 506, 509, 512, 515, 518, 521, 524 or 527; (ii) a VL CDR2 comprising the sequence shown in SEQ ID NO: 194, 197, 200, 203, 206, 209, 212, 215, 218, 221, 224, 227, 230, 233, 236, 239, 242, 245, 248, 251, 254, 257, 260, 263, 465, 468, 471, 474, 477, 480, 483, 486, 489, 492, 495, 498, 501, 504, 507, 510, 513, 516, 519, 522, 525 or 528; and (iii) a VL CDR3 comprising the sequence shown in SEQ ID NO: 195, 198, 201, 204, 207, 210, 213, 216, 219, 222, 225, 228, 231, 234, 237, 240, 243, 246, 249, 252, 255, 258, 261, 264, 466, 469, 472, 475, 478, 481, 484, 487, 490, 493, 496, 499, 502, 505, 508, 511, 514, 517, 520, 523, 526 or 529.

In another aspect, provided is an isolated antibody which specifically binds to CD70, wherein the antibody comprises: a VH region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 38, 40, 42, 44, 46, 48, 289, 291, 293, 295, 297, 299, 301, 303, 305, 307, 309, 311, 313, 315, 317, 319, 321, 323, 325, 327, 329 or 331; or a VL region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 37, 39, 41, 43, 45, 47, 288, 290, 292, 294, 296, 298, 300, 302, 304, 306, 308, 310, 312, 314, 316, 318, 320, 322, 324, 326, 328 or 330.

In some embodiments, provided is an antibody having any one of partial light chain sequence as listed in Table 1 or any one of partial heavy chain sequence as listed in Table 1. In Table 1, the underlined sequences are CDR sequences according to Kabat and in bold according to Chothia.

TABLE 1

| mAb | Light Chain | Heavy Chain |
| --- | --- | --- |
| 31H1 | DIVMTQNPLSSPVTLGQPASISCRS SQSLVHSDGNTYLSWLQQRPGQS PRLLIYKISNRFSGVPDRFSGSGAG TDFTLKISRVEAEDVGVYYCMQAT QFPLTIGGGSKVEIK (SEQ ID NO: 1) | QVQLVQSGAEVKKPGSSVKVSCKA SGGTFSSYGFSWVRQAPGQGLEW MGGIIPIFGSANYAQKFQGRVTITAD KSTSTVYMELISLRSEDTAVYYCAR GGSSSPFAYWGQGTLVTVSS (SEQ ID NO: 2) |
| 63B2 | DIVMTQTPLSSPVTLGQPASISCRS SQSLVHSDGNTYLSWLQQRPGQS PRLLIYKISNRFSGVPDRFSGSGAG TDFTLKISRVEAEDVGVYYCMQAT QFPLTIGGGSKVEIK (SEQ ID NO: 3) | QVQLVQSGAEVKKPGSSVKVSCKA SGGTFSSYGFSWVRQAPGQGLEW MGGIIPIFGTANYAQKFQGRVTITAD KSTSTVFMELISLRSEYTAVYYCAR GGSSSPFAYWGQGTLVTVSS (SEQ ID NO: 4) |
| 40E3 | DIQMTQSPSSLSASVGDRVTITCRA SQGISNYLAWFQQKPGKAPKSLIY AASSLQSGVPSKFSGSGSGTDFTL TISSLQPEDFATYYCQQYNSYPLTF GGGTKVEIK (SEQ ID NO: 5) | QVQLQESGPGLVKPSETLSLTCTVS GGSISSYYWNWIRQPPGKGLEWIG YIYYSGSTNYNPSLKSRVTISVDTSK NQFSLKLRSVTAADTAVYYCARDIR TWGQGTLVTVSS (SEQ ID NO: 6) |
| 42C3 | DVVMTQSPLSLPVTLGQPASISCRS SQSLVYSDENTYLNWFQQRPGQS LRRLIYQVSNRDSGVPDRFSGSGS GTDFTLKISRVEAEDVGVYFCMQG TYWPPTFGGGTKVEIK (SEQ ID NO: 7) | EVQLVESGGGLVQPGGSLRLSCAA SGFTFRNSWMSWVRQAPGKGLEW VANIKRDGSEKYYVDSVKGRFTISR DNAKNSLYLQMNSLRAEDTAVYYC ARDQTGSFDYWGQGTLVTVSS (SEQ ID NO: 8) |
| 45F11 | EIVMTQSPATLSMSLGERATLSCRA SQSVSSSLAWYQQKPGQAPRLLIY GASTRATGIPARFGGSGSGTEFTL TISSLQSEDFAVYYCQQYINWPHFG GGTKVEIK (SEQ ID NO: 9) | QVQLRGSGPGLVKPSETLSLTCTVS DDSISVYYWSWIRQPAGKGLEWIGR VYSSGNINYNPSLESRVTMSVDTSK SRFSLNLSSVTAADTAVYYCARGLD AFDIWGQGTMVTVSS (SEQ ID NO: 10) |
| 64F9 | DIQMTQSPSSLSASVGDRVTITCQA SQDISNYLNWYQQKPGKAPKILIYG ASNLETGVPSRFSGSGSGTDFTFAI SSLQPEDVATYYCQQYDNFPITFG QGTRLEIK (SEQ ID NO: 11) | EVQLLESGGGLVQPGESLRLSCEVS GFTFTSYAMSWVRQVPGKGLEWVS IISGVAFTTYYADSVKGRFTISRDHS KNTLYLQMNGLRAEDTAVYYCVKV DGEVYWGQGTLVTVSS (SEQ ID NO: 12) |
| 72C2 | EIVMTQSPDTLSVSPGERAILSCRA SQSVSSNLAWYQQKPGQAPRLLIY SASTRASGIPARFSGSGSGTEFTLS ISSLQSEDFAVYYCQQYDNWPPLT FGGGTKVEIK (SEQ ID NO: 13) | QVQLVQSGAEVKKPGSSVKVSCEA SGGTFITYAISWVRQAPGQGLEWM GGIIPFFGTANYAQKFQGRVTITADK STSTASMELRSLRSEDTAMYYCAQ WELFFFDFWGQGTPVTVSS (SEQ ID NO: 14) |

TABLE 1-continued

| mAb | Light Chain | Heavy Chain |
|---|---|---|
| 2F10 | EIVLTQSPGTLSLSPGERATLSCRA SQSVSSSYLAWYQQPGQAPRLLI YGASSRATGIPDRFSGSGSGTDFT LTISRLEPEDFAIYYCQQYGSSPLTF GGGTKVEIK<br>(SEQ ID NO: 15) | AVQLVESGGGLVQPGGSLRLSCAA SGFTFTYYSMNWVRQAPGKGLEW VSHISIRSSTIYFADSAKGRFTISRDN AKNSLYLQMNSLRDEDTAVYYCAR GSGWYGDYFDYWGQGTLVTVSS<br>(SEQ ID NO: 16) |
| 4F11 | DIQMTQSPSAMSASVGDRVTITCR ASQDISNYLAWFQQKPGKVPKRLI YAAASSLQSGVPSRFSGSGSGTEFT LTISSLLPEDFATYYCLQLNSFPFTF GGGTKVEIN<br>(SEQ ID NO: 17) | QVTLKESGPVLVKPTETLTLTCTVS GFSLSNARMGVTWIRQPPGKALEW LAHIFSNDEKSYSTSLKSRLTISKDT SKTQVVLTMTNMDPVDTATYYCARI RDYYDISSYYDYWGQGTLVSVSS<br>(SEQ ID NO: 18) |
| 10H10 | DIQMTQSPSSVSASVGDRVTITCRA SQGISSWLAWYQQKPGKAPKVLIY AASSLQSGVPSRFSGSGSGTDFTL TISSLQPEDFATYYCQQAFSFPFTF GPGTKVDIK<br>(SEQ ID NO: 19) | EVQLVESGGGLVQPGGSLRLSCAV SGFTFSNHNIHWVRQAPGKGLEWIS YISRSSSTIYYADSVKGRFTISRDNA KNSLYLQMNSLRDEDTAVYYCARD HAQWYGMDVWGQGTTVTVSS<br>(SEQ ID NO: 20) |
| 17G6 | DIVMTQSPDSLAVSLGERATINCKS SQSVLYSYNNKNYVAWYQQKPGQ PPNLLIFWASTRESGVPDRFSGSG SGTDFTLTISSLQAEDVAVYYCQQY YSTLTFGGGTKVEIK<br>(SEQ ID NO: 21) | EVQLVESGGGLVQPGGSLRLSCVA SGFTFSSYWMSWVRQAPGKGLEW VASIKQDGSEKYYVDSVKGRFTISR DNAKNSVYLQMNSLRAEDTGVYYC AREGVNWGWRLYWHFDLWGRGTL VTVSS<br>(SEQ ID NO: 22) |
| 65E11 | EIVLTQSPGTLSLSPGERVTLSCRA SQSVSSSYLAWYQQKPGQAPRLLI YDASSRATGIPDRFSGSGSGTDFT LTISRLEPEDFAVYYCQQYGSSPLT FGGGTKVEIK<br>(SEQ ID NO: 23) | EVQVVESGGGLVQPGGSLRLSCAA SGFTFSSYSMNWVRQAPGKGLEW VSHSSISRGNIYFADSVKGRFTISRD NAKNSLYLQMNSLRDEDTAVYYCA RGSGWYGDYFDYWGQGTLVTVSS<br>(SEQ ID NO: 24) |
| P02B10 | ELQSVLTQPPSASGTPGQRVTISCS GSSSNIGSNYVYWYQQLPGTAPKL LIYRNNQRPSGVPDRFSGSKSGTS ASLAISGLRSEDEADYYCAAWDDS LSGVVFGGGTKLTVL<br>(SEQ ID NO: 25) | EVQLLESGGGLVQPGGSLRLSCAA SGFAFSNYAMSWVRQAPGKGLEW VSAIRGGGGSTYYADSVKGRFTISR DNSKNTLYLQMNSLRAEDTAVYYCA RDFISGTWYPDYWGQGTLVTVSS<br>(SEQ ID NO: 26) |
| P07D03 | ELQSVLTQPPSASGTPGQRVTISCS GSRSNIGSNYVYWYQQLPGTAPKL LIYRNNQRPSGVPDRFSGSKSGTS ASLAISGLRSEDEADYYCASWDGS LSAVVFGTGTKLTVL<br>(SEQ ID NO: 27) | EVQLVQSGAEVKKPGESLKISCKGS GYRFTSYWIGWVRQMPGKGLEWM GSIYPDDSDTRYSPSFQGQVTISAD KSISTAYLQWSSLKASDTAMYYCAS STVDYPGYSYFDYWGQGTLVTVSS<br>(SEQ ID NO: 28) |
| P08A02 | ELQSVLTQPPSASGTPGQRVTISCS GSSSNIGSNYVYWYQQLPGTAPKL LIYRNNQRPSGVPDRFSGSKSGTS ASLAISGLRSEDEADYYCATWDDS LGSPVFGTGTKLTVL<br>(SEQ ID NO: 29) | EVQLVQSGAEVKKPGESLKISCKGS GYTFTNYWIAWVRQMPGKGLEWM GIIYPDGSDTRYSPSFQGQVTISADK SISTAYLQWSSLKASDTAMYYCARD ITSWYYGEPAFDIWGQGTLVTVSS<br>(SEQ ID NO: 30) |
| P08E02 | ELDIQMTQSPSSLSASVGDRVTITC RASQSISRYLNWYQQKPGKAPKLLI YAAASILQTGVPSRFSGSGSGTDFT LTISSLQPEDFATYYCQQSYSTTM WTFGQGTKVEIK<br>(SEQ ID NO: 31) | EVQLVQSGAEVKKPGESLKISCKGS GYSFTSSWIGWVRQMPGKGLEWM GIIYPGDSDTRYSPSFQGQVTISADK SISTAYLQWSSLKASDTAMYYCAKG LSQAMTGFGFDYWGQGTLVTVSS<br>(SEQ ID NO: 32) |
| P08F08 | ELQSVLTQPPSASGTPGQRVTISCS GSSSNIGSNYVNWYQQLPGTAPKL LIYGDYQRPSGVPDRFSGSKSGTS ASLAISGLRSEDEADYYCATRDDSL SGSVVFGTGTKLTVL<br>(SEQ ID NO: 33) | EVQLVQSGAEVKKPGESLKISCKGS GYGFTSYWIGWVRQMPGKGLEWM GIIHPDDSDTKYSPSFQGQVTISADK SISTAYLQWSSLKASDTAMYYCASS YLRGLWGGYFDYWGQGTLVTVSS<br>(SEQ ID NO: 34) |
| P08G02 | ELDIQMTQSPSSLSASVGDRVTITC RASQSIYDYLHWYQQKPGKAPKLLI YDASNLQSGVPSRFSGSGSGTDFT LTISSLQPEDFATYYCQQSYTTPLF TFGQGTKVEIK<br>(SEQ ID NO: 35) | EVQLVQSGAEVKKPGESLKISCKGS GYTFPSSWIGWVRQMPGKGLEWM GIIYPDTSHTRYSPSFQGQVTISADK SISTAYLQWSSLKASDTAMYYCARA SYFDRGTGYSSWWMDVWGQGTLV TVSS<br>(SEQ ID NO: 36) |

TABLE 1-continued

| mAb | Light Chain | Heavy Chain |
|---|---|---|
| P12B09 | ELDIQMTQSPSSLSASVGDRVTITCRASQYIGRYLNWYQQKRGKAPKLLIHGATSLASGVPSRFSGSGSGTDFTLTISSLQPEDFATYYCQQSYSTTSPTFGQGTKVEIK (SEQ ID NO: 37) | EVQLLESGGGLVQPGGSLRLSCAASGFTFSQYSMSWVRQAPGKGLEWVSAISGGGVSTYYADSVKGRFTISRDNSKNTLYLQMNSLRAEDTAVYYCASDISDSGGSHWYFDYWGQGTLVTVSS (SEQ ID NO: 38) |
| P12F02 | ELQSVLTQPPSASGTPGQRVTISCSGSTSNIGRNYVYWYQQLPGTAPKLLIYRTNQRPSGVPDRFSGSKSGTSASLAISGLRSEDEADYYCAAWDDSLSGRVFGTGTKLTVL (SEQ ID NO: 39) | EVQLLESGGGLVQPGGSLRLSCAASGFTFSSYAMSWVRQAPGKGLEWVSTISGTGGTTYYADSVKGRFTISRDNSKNTLYLQMNSLRAEDTAVYYCAKVRAGIDPTASDVWGQGTLVTVSS (SEQ ID NO: 40) |
| P12G07 | ELQSVLTQPPSASGTPGQRVTISCSGSSSNIGSNYVYWYQQLPGTAPKPLIYMMNNQRPSGVPDRFSGSKSGTSASLAISGLRSEDEADYYCAAWDDSLSAVVFGTGTKLTVL (SEQ ID NO: 41) | EVQLLESGGGLVQPGGSLRLSCAASGFTFNNFAMSWVRQAPGKGLEWVSGISGSGDNTYYADSVKGRFTISRDNSKNTLYLQMNSLRAEDTAVYYCAKDRDIGLGWYSYYLDVWGQGTLVTVSS (SEQ ID NO: 42) |
| P13F04 | ELQSVLTQPPSASGTPGQRVTISCSGSNSNIGTNYVSWYQQLPGTAPKLLIYRSSRRPSGVPDRFSGSKSGTSASLAISGLRSEDEADYYCAAWDGSLSGHWVFGTGTKLTVL (SEQ ID NO: 43) | QVQLVQSGAEVKKPGSSVKVSCKASGGTFSSYAISWVRQAPGQGLEWMGEIIPIFGTASYAQKFQGRVTITADESTSTAYMELSSLRSEDTAVYYCARAGWDDSWFDYWGQGTLVTVSS (SEQ ID NO: 44) |
| P15D02 | ELDIQMTQSPSSLSASVGDRVTITCRASQSIDTYLNWYQQKPGKAPKLLIYSASSLHSGVPSRFSGSGSGTDFTLTISSLQPEDFATYYCQQSYSTTAWTFGQGTKVEIK (SEQ ID NO: 45) | EVQLVQSGAEVKKPGESLKISCKGSGYSFASYWIGWVRQMPGKGLEWMGVIYPGTSETRYSPSFQGQVTISADKSISTAYLQWSSLKASDTAMYYCAKGLSASASGYSFQYWGQGTLVTVSS (SEQ ID NO: 46) |
| P16C05 | ELDIQMTQSPSSLSASVGDRVTITCRASQSIGQSLNWYQQKPGKAPKLLIYGASSLQSGVPSRFSGSGSGTDFTLTISSLQPEDFATYYCQQSYSTPITFGQGTKVEIK (SEQ ID NO: 47) | EVQLVQSGAEVKKPGESLKISCKGSGYSFTDYWIGWVRQMPGKGLEWMGMISPGGSTTIYRPSFQGQVTISADKSISTAYLQWSSLKASDTAMYYCAREMYTGGYGGSWYFDYWGQGTLVTVSS (SEQ ID NO: 48) |
| 10A1 | DIQMTQSPSTLSASVGDRVTITCRASQSISTWLAWYQQKPGKAPKVLIYKASSLESGVPSRFSGSGSGTEFILTINSLQPDDFASYYCQQYKSYSHTFGQGTKLEIK (SEQ ID NO: 288) | QVQLQESGPGLVKPSETLSLTCTVSGGSISYYYWTWIRQPPGKGLEWIGHIYYSGSTNYNPSLKSRVTISIDTSKNLFSLKLSSVTAADTAVYYCARAEGSIDAFDFWGQGTMVTVSS (SEQ ID NO: 289) |
| 10E2 | DIQMTQSPSTLSASVGDRVTITCRASQSISSWLAWYQQKPGKAPKVLIYKASSLESGVPSRFSGSGSGTEFTLTINSLQPDDFATYYCQQYKSFSLTFGQGTKLEIK (SEQ ID NO: 290) | EVQLVESGGGLIQPGGSLRLSCAASGFTVSSNYMTWVRQAPGKGLEWVSVIYSGGSTYYADSVKGRFTISRDNSKNTLYLQMNSLRAEDTAVYYCARNWGDYWGQGTLVTVSS (SEQ ID NO: 291) |
| 11A1 | DIQMTQSPSTLSASVGDRVTITCRASQSISSWLAWYQQKPGKAPKVLIYKASTLESGVPSRFSGSGSGTEFTLTISSLQPDDFATYYCQQNSYSYTFGHGTKLEIK (SEQ ID NO: 292) | QVQLQESGPGLVKPSGTLSLTCTVSGGSIDYYFWNWFRQSPVKGLEWIGHVYDIGNTKYNPSLKSRVTISIDTSENQFSLKLNSVTAADTAVYYCARGEGAIDAFDIWGQGTMVTVSS (SEQ ID NO: 293) |
| 11C1 | DIQMTQSPSILSASVGDRVTITCRASQSVSSWLAWYQQKPGKAPKVLIYKASSLESGVPSRFSGTGSGTEFTLTISSLQSDDFATYYCQQYNTYSHTFGQGTKLEIK (SEQ ID NO: 294) | QVQLQESGPGLVKPSETLSLNCTVSGGSISYYYWTWIRQPPGKGLEWIGHVIYSGTTNYNPSLKSRVTISVDTSKNQFSLKLNSVTAADTAVYYCVRAEGSIDAFDLWGQGTMVTVSS (SEQ ID NO: 295) |

TABLE 1-continued

| mAb | Light Chain | Heavy Chain |
|---|---|---|
| 11D1 | AIQMTQSPSSLSASVGDRVTITCRA SQGIRNDLGWYQQKPGKAPKLLIY AASSLQSGVPSRFSGSGSGTDFTL TISSLQPEDFATYYCLQDYNYPFTF GPGTKVDIK (SEQ ID NO: 296) | QVQLVESGGGVVQPGRSLRLSCVA SGFTFSDYGIHWVRQAPGMGQEW VAVIWYDGSiKKYSDSVKGRFIISRD NSENTVYLQMNSLRGEDTAIYYCAR DEVGtfGAFDFWGQGTKVTVSS (SEQ ID NO: 297) |
| 11E1 | DIQMTQSPSSLSASVGDSITITCRA SQDIDNYLAWYQQKTGKVPKVLIY AASALQSGVPSRFSGSGSGTDFTL TISSLQPEDVATYYCQNYNSGPRTF GQGTKVEIK (SEQ ID NO: 298) | QVQLQESGPGLVKPLQTLSLTCTVS GGSISSdgYYWSWIRQNPGKGLEWI GYMYYSGSTYYNPSLKSRVTISVDT SKNQFSLKLRSVTAADTAVYYCTRD FGWYFDLWGRGTLVTVSS (SEQ ID NO: 299) |
| 12A2 | DIQMTQSPSSLSASVGDRVTITCRA SQDISNYLTWYQQKPGRVPEVLIY AASALQSGVPSRFSGSGSGTDFTL TISSLQPEDVATYYCQNYNSAPRTF GQGTKVEIK (SEQ ID NO: 300) | QVQLQESGPGLVKPSQSLSLTCSVS GGSVSSdgYYWSWIRQHPGKGLEW IGYIYYRRITDYNPSLKSRVNISLDTS KNQFSLKLSSVTAADTAVYYCARDF GWYFDLWGRGTLVAVSS (SEQ ID NO: 301) |
| 12C4 | DIVMTQSPLSLPVTPGEPASISCRS SQSLLHSNGYNYLDWYLQKPGQS PQVLILLGSNRASGVPDRVSASGS GTDFTLKISRMQAEDVGIYYCMQTL QTPFTFGQGTKLEIK (SEQ ID NO: 302) | QVQLVQSGAEVKKPGASVKVSCKA SGYTFTGYYLHWVRQAPGQGLEW MGWINpNSGGTNYAQKFQGRVTMT RDTSITTAYMELSRLRIDDTAVYYCA RDRGVtmivDGMDDWGQGTTVTVS S (SEQ ID NO: 303) |
| 12C5 | DIQLTQSPSFLSASVGDRVIITCRAS QGINSHLAWYQQKPGKAPKLLIYY ASTLPSGVPSRFSGSGSGTEFTLT VTSLQPEDFATYYCQQLNHYPITFG QGTRLDIN (SEQ ID NO: 304) | EVELVESGGGMVQPGRSLRLSCAA SGFTFSDYGMHWVRQAPGMGLEW VTVIWYDGSnKYYADSVKGRFTISR DNSKNTVFLQMNSLRAEDTAVYYC ARDEVGfvGAFDIWGQGTMVTVSS (SEQ ID NO: 305) |
| 12D3 | DIQMTQSPSSLSASVGDRVTITCRA SQGISNYLAWYQQKPGKVPKLLIY AASTLHSGVPSRFSGSGSGTDFTL TISSLQPEDVATYYCQKYNSAPRTF GQGTKVEIK (SEQ ID NO: 306) | QVQLQESGPGLVKPSQTLSLTCTVS GGSISSdgYYWSWIRQHPGKGLEWI GYMYYSGITYHNPSLKSRVTISVDTS KNQFSLRLSSVTAADTAVYYCARDF GWYFDLWGRGTLVTVSS (SEQ ID NO: 307) |
| 12D6 | DIQMTQSPSSLSASVGDRVTITCRA SQDISNYLAWYQQKPGKVPKLLIYA ASTLHSGVPSRFSGSGSGTDFTLTI SSLQPDDFAAYYCQKYNSAPRTFG QGTKVEIK (SEQ ID NO: 308) | QVQLQESGPGLVKPSQTLSLTCTVS GGSISSdaYYWSWIRQHPGKGLEWI GYMYYSGITYYNPSLKSRVTISVDTS KNQFSLKLSSVTAADTAVYYCARDF GWYFDLWGRGTLVTVSS (SEQ ID NO: 309) |
| 12D7 | DIQLTQSPSFLSASVGDRVSITCRA SQDISSFLAWYQQKPGKAPVLLIYV ASTLQSGVPSRFSGSGSGTEFTLT VSSLQPEDFATYYCQQLHVYPITFG QGTRLEIR (SEQ ID NO: 310) | QVQLVESGGGVVQPGRSLRLSCVA SGFTFSDYGIHWVRQAPGMGQEW VAVIWYDGSiKKYSDSVKGRFIISRD NSENTVYLQMNSLRGEDTAIYYCAR DEVGtfGAFDFWGQGTKVIVSS (SEQ ID NO: 311) |
| 12F5 | DIVMTQTPLSLPVTPGEPASISCRS SQSLLDSDDGNtYLDWYLQKPGQS PQLLIYTLSYRASGVPDRFSGSGS GTDFTLKISRVEAEDVGVYYCMQRI EFPFTFGPGTKVDIK (SEQ ID NO: 312) | EVQLVESGGGLVKPGGSLRLSCAA SGFTFSNAWMSWVRQAPGKGLEW VGRIKsktGGGTTDYAAPVKGRFTIS RDDSKNTLYLQMNSLKTEDTAVYYC TSLIVGaiSLFDYWGQGTLVTVSS (SEQ ID NO: 313) |
| 12H4 | DIQMTQSPSALSASVGDRVAITCRA SQTISTWLAWYQQKPGKAPKVLIY KASNLESGVPSRFSGSGSGTEFTL TINSLQPDDFATYYCQQYQTFSHTF GQGTKLEIK (SEQ ID NO: 314) | QVQLRESGPGLVKPSETLSLTCTIS GGSISYYFWTWIRQPPGRGLEWIG QIYYSGNTNSNPSLKSRVTISIDTSK NQFSLKLTSVTVADTAVYYCVRAEG SIDAFDIWGQGTMVAVSS (SEQ ID NO: 315) |
| 8C8 | DMQMTQSPSSLSASVGDRVTLTCR ASQGISNYLAWFQLKPGKVPKLLIY AASTLQSGVPSRFSGSGSGTDFAL TISSLQPEDVATYYCQKYNSAPLTF GGGTKVEIK (SEQ ID NO: 316) | EVQLVESGGGLVKPGGSLRLSCVA SGFTFSSYSMNWVRQFPGKGLEW VSSIStSSNYIHYADSLQGRFTISRDN AKNSLYLQMSSLRVEDTAVYYCVRD KGTtltnWYFDLWGRGTLVTVSS (SEQ ID NO: 317) |

TABLE 1-continued

| mAb | Light Chain | Heavy Chain |
|---|---|---|
| 8F7 | DIVMTQSPLSLPVTPGEPASISCRS SQTLVHSNGYNYLNWYLQKPGQS PQLLIYLGSNRASGVPDRFSGSGS GSDFTLKISRMEAEDVGVYYCMQA IQTPYTFGQGTNVEIK (SEQ ID NO: 318) | QVQLVESGGGVVQPGRSLRLSCGA SGFTFSSYGMHWVRQAPGKGLEW VAVIWYDGSnKYYADSLKGRFTISR DNSKNTLYLQMNSLRAEDTAVYYCA RDGYSgssDAFDIWGQGTMVTVSS (SEQ ID NO: 319) |
| 8F8 | DIQMTQSPSTLSASVGDRVTITCRA SQSISSWLAWYQQKPGKAPKVLIY KASNLESGVPSRFSGSGSGTEFTL TISSLQPDDFATYYCQQYNSYSCTF GQGTKLEIK (SEQ ID NO: 320) | QVQLQESGPGLVQPSETLSLTCTVS GGSISYYYWSWIRQPPGKGLEWIG NINYMGNTIYNPSLKSRVTISVDTSK DQFSLKLTSVSAADTAVYYCVRAEG SIDAFDFWGQGTLVAVSL (SEQ ID NO: 321) |
| 9D8 | DIQMTQSPSSLSASVGDRIIFTCQA SQDINNYLHWYQQKPGKAPKLLIY DASDWETGVPSRFSGSGSGTDFT FTISSLQPEDIATYYCQQYDHLPITF GQGTRVEIK (SEQ ID NO: 322) | QVQLVQSGAEVTKPGASVKVSCKA SGYIFTGYYIYWVRQAPGQGLEWM GWINpSSGGTNYAQKFQGRVTMAR DTSISTAYMELSLRSDDTAVYYCA RDRKReyyynFGMDVWGQGTTVTV ST (SEQ ID NO: 323) |
| 9E10 | DIQMTQSPSSLSASVGDRVILTCQA SQDISNYLHWYQQKPGKAPKLLIYD ASDLETGVPSRFSGSGSGADFTFTI SNLQPEDFATYYCQQYDHLPITFG QGTRLEIK (SEQ ID NO: 324) | QVQLVQSGAEVTKPGASVKVSCKA SGYTFTSHYIYWVRQAPGQGLEWM GWINpNSGGTNYAQKFQDRVTMAR DTSISTAYMELSRLRSDDTAVYYCA KDRKReyyynFGMDVWGQGTTVTV SA (SEQ ID NO: 325) |
| 9E5 | DIQMTQSPSSLSASVGDRVILTCQA SQDISNYLHWYQQKPGKAPKLLIYD ASDLETGVPSRFSGSGSGADFTFTI SNLQPEDFATYYCQQYDHLPITFG QGTRLEIK (SEQ ID NO: 326) | QVQLVQFGVEVRKPGASVKVSCKV SGFTFTSHYIYWVRQAPGQGLEWM GWINpNSGGTKYAQKFQDRVTMAR DTSISTAYMELSRLRSDDTSVYYCV KDRKReyyynFGMDVWGQGTTVTV SS (SEQ ID NO: 327) |
| 9F4 | DIQMTQSPSSLSASVGDRVTITCQA SQDISNYLNWYQQKPGKAPKLLIYD ASNLETGVPSRFSGSGSGTDFTFTI SSLQPEDIATYYCQQYDNLPYTFG QGTKLEIK (SEQ ID NO: 328) | EVQMLESGGGLIQPGGSLRLSCKTS GFTLSIYAIHWVRQAPGRGLEWVSS FGgRGSSTYFADSVKGRFTISRDAS ENSLYLHMNSLRAEDTAVYYCAKEK DWgRGFDYWGQGTLVTVSS (SEQ ID NO: 329) |
| 9F8 | DIVMTQSPLSLPVTPGEPASISCRS SQSLLYSNGYNYLDWYLQKPGQS PQLLIFLNSNRASGVPDRFSGSGS GTDFTLKISRVEAEDVGVYFCMQA LQTPLTFGGGTKVEIK (SEQ ID NO: 330) | EVQLVESGGGLVKPGGSLRLSCAA SGFTFSNYSMNWVRQAPGKGLEW VSSISsSTIYIYYADSVKGRFTISRDN AKKSLYLQMNSLRAEDTAVYYCARD IGWevftLGFDYWGQGTQVTVSS (SEQ ID NO: 331) |

Also provided herein are CDR portions of antigen binding domains of antibodies to CD70 (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
|---|---|---|---|
| mAb | CDRH1 | CDRH2 | CDRH3 |
| 31H1 | SYGFS (SEQ ID NO: 49) (Kabat); GGTFSSY (SEQ ID NO: 50) (Chothia); GGTFSSYGFS (SEQ ID NO: 51) (Extended) | GIIPIFGSANYAQK FQG (SEQ ID NO: 52) (Kabat); IPIFGS (SEQ ID NO: 53) (Chothia) | GGSSSPFAY (SEQ ID NO: 54) |

TABLE 2-continued

| | | | |
|---|---|---|---|
| 63B2 | SYGFS (SEQ ID NO: 55) (Kabat); GGTFSSY (SEQ ID NO: 56) (Chothia); GGTFSSYGFS (Extended) (SEQ ID NO: 57) | GIIPIFGTANYAQK FQG (SEQ ID NO: 58) (Kabat); IPIFGT (SEQ ID NO: 59) (Chothia) | GGSSSPFAY (SEQ ID NO: 60) |
| 40E3 | SYYWN (SEQ ID NO: 61) (Kabat); GGSISSY (SEQ ID NO: 62) (Chothia); GGSISSYYWN (SEQ ID NO: 63) (Extended) | YIYYSGSTNYNPS LKS (SEQ ID NO: 64) (Kabat); YYSGS (SEQ ID NO: 65) (Chothia) | DIRTW (SEQ ID NO: 66) |
| 42C3 | NSVVMS (SEQ ID NO: 67) (Kabat); GFTFRNS (SEQ ID NO: 68) (Chothia); GFTFRNSWMS (SEQ ID NO: 69) (Extended) | NIKRDGSEKYYV DSVKG (SEQ ID NO: 70) (Kabat); KRDGSE (SEQ ID NO: 71) (Chothia) | DQTGSFDY (SEQ ID NO: 72) |
| 45F11 | VYYWS (SEQ ID NO: 73) (Kabat); DDSISVY (SEQ ID NO: 74) (Chothia); DDSISVYYWS (SEQ ID NO: 75) (Extended) | VYSSGNINYNPSL ES (SEQ ID NO: 76) (Kabat); YSSGN (SEQ ID NO: 77) (Chothia) | GLDAFDI (SEQ ID NO: 78) |
| 64F9 | SYAMS (SEQ ID NO: 79) (Kabat); GFTFTSY (SEQ ID NO: 80) (Chothia); GFTFTSYAMS (SEQ ID NO: 81) (Extended) | RVYSSGNINYNP SLES (SEQ ID NO: 82) (Kabat); YSSGN (SEQ ID NO: 83) (Chothia) | GLDAFDI (SEQ ID NO: 84) |
| 72C2 | TYAIS (SEQ ID NO: 85) (Kabat); GGTFITY (SEQ ID NO: 86) (Chothia); GGTFITYAIS (SEQ ID NO: 87) (Extended) | GIIPFFGTANYAQ KFQG (SEQ ID NO: 88) (Kabat); IPFFGT (SEQ ID NO: 89) (Chothia) | WELFFFDF (SEQ ID NO: 90) ID |
| 2F10 | YYSMN (SEQ ID NO: 91) (Kabat); GFTFTYY (SEQ ID NO: 92) (Chothia); GFTFTYYSMN (SEQ ID NO: 93) (Extended) | HISIRSSTIYFADS AKG (SEQ ID NO: 94) (Kabat); SIRSST (SEQ ID NO: 95) (Chothia) | GSGWYGDYFDY (SEQ ID NO: 96) |
| 4F11 | NARMGVT (SEQ ID NO: 97) (Kabat); GFSLSNARM (SEQ ID NO: 98) (Chothia); GFSLSNARMGVT (SEQ ID NO: 99) (Extended) | HIFSNDEKSYSTS LKS (SEQ ID NO: 100) (Kabat); FSNDE (SEQ ID NO: 101) (Chothia) | IRDYYDISSYYDY (SEQ ID NO: 102) |
| 10H10 | NHNIH (SEQ ID NO: 103) (Kabat); GFTFSNH (SEQ ID NO: 104) (Chothia); GFTFSNHNIH (SEQ ID NO: 105) (Extended) | YISRSSSTIYYAD SVKG (SEQ ID NO: 106) (Kabat); SRSSST (SEQ ID NO: 107) (Chothia) | DHAQWYGMDV (SEQ ID NO: 108) |
| 17G6 | SYWMS (SEQ ID NO: 109) (Kabat); GFTFSSY (SEQ ID NO: 110) (Chothia); GFTFSSYWMS (SEQ ID NO: 111) (Extended) | SIKQDGSEKYYV DSVKG (SEQ ID NO: 112) (Kabat); KQDGSE (SEQ ID NO: 113) (Chothia) | EGVNWGWRLYW HFDL (SEQ ID NO: 114) |
| 65E11 | SYSMN (SEQ ID NO: 115) (Kabat); GFTFSSY (SEQ ID NO: 116) (Chothia); GFTFSSYSMN (SEQ ID NO: 117) (Extended) | HSSISRGNIYFAD SVKG (SEQ ID NO: 118) (Kabat); SISRGN (SEQ ID NO: 119) (Chothia) | GSGWYGDYFDY (SEQ ID NO: 120) |

TABLE 2-continued

| | | | |
|---|---|---|---|
| P02B10 | NYAMS (SEQ ID NO: 121) (Kabat); GFAFSNY (SEQ ID NO: 122) (Chothia); GFAFSNYAMS (SEQ ID NO: 123) (Extended) | AIRGGGGSTYYA DSVKG (SEQ ID NO: 124) (Kabat); RGGGGS (SEQ ID NO: 125) (Chothia) | DFISGTWYPDY (SEQ ID NO: 126) |
| P07D03 | SYWIG (SEQ ID NO: 127) (Kabat); GYRFTSY (SEQ ID NO: 128) (Chothia); GYRFTSYWIG (SEQ ID NO: 129) (Extended) | SIYPDDSDTRYSP SFQG (SEQ ID NO: 130) (Kabat); YPDDSD (SEQ ID NO: 131) (Chothia) | STVDYPGYSYFD Y (SEQ ID NO: 132) |
| P08A02 | NYWIA (SEQ ID NO: 133) (Kabat); GYTFTNY (SEQ ID NO: 134) (Chothia); GYTFTNYWIA (SEQ ID NO: 135) (Extended) | IIYPDGSDTRYSP SFQG (SEQ ID NO: 136) (Kabat); YPDGSD (SEQ ID NO: 137) (Chothia) | DITSWYYGEPAF DI (SEQ ID NO: 138) |
| P08E02 | SSWIG (SEQ ID NO: 139) (Kabat); GYSFTSS (SEQ ID NO: 140) (Chothia); GYSFTSSWIG (SEQ ID NO: 141) (Extended) | IIYPGDSDTRYSP SFQG (SEQ ID NO: 142) (Kabat); YPGDSD (SEQ ID NO: 143) (Chothia) | GLSQAMTGFGFD Y (SEQ ID NO: 144) |
| P08F08 | SYWIG (SEQ ID NO: 145) (Kabat); GYGFTSY (SEQ ID NO: 146) (Chothia); GYGFTSYWIG (SEQ ID NO: 147) (Extended) | IIHPDDSDTKYSP SFQG (SEQ ID NO: 148) (Kabat); HPDDSD (SEQ ID NO: 149) (Chothia) | SYLRGLWGGYF DY (SEQ ID NO: 150) |
| P08G02 | SSWIG (SEQ ID NO: 151) (Kabat); GYTFPSS (SEQ ID NO: 152) (Chothia); GYTFPSSWIG (SEQ ID NO: 153) (Extended) | IIYPDTSHTRYSP SFQ (SEQ ID NO: 154) (Kabat); YPDTSH (SEQ ID NO: 155) (Chothia) | ASYFDRGTGYSS WWMDV (SEQ ID NO: 156) |
| P12809 | QYSMS (SEQ ID NO: 157) (Kabat); GFTFSQY (SEQ ID NO: 158) (Chothia); GFTFSQYSMS (SEQ ID NO: 159) (Extended) | AISGGGVSTYYA DSVKG (SEQ ID NO: 160) (Kabat); SGGGVS (SEQ ID NO: 161) (Chothia) | DISDSGGSHWYF DY (SEQ ID NO: 162) |
| P12F02 | SYAMS (SEQ ID NO: 163) (Kabat); GFTFSSY (SEQ ID NO: 164) (Chothia); GFTFSSYAMS (SEQ ID NO: 165) (Extended) | TISGTGGTTYYAD SVKG (SEQ ID NO: 166) (Kabat); SGTGGT (SEQ ID NO: 167) (Chothia) | VRAGIDPTASDV (SEQ ID NO: 168) |
| P12G07 | NFAMS (SEQ ID NO: 169) (Kabat); GFTFNNF (SEQ ID NO: 170) (Chothia); GFTFNNFAMS (SEQ ID NO: 171) (Extended) | GISGSGDNTYYA DSVKG (SEQ ID NO: 172) (Kabat); SGSGDN (SEQ ID NO: 173) (Chothia) | DRDIGLGWYSYY LDV (SEQ ID NO: 174) |
| P13F04 | SYAIS (SEQ ID NO: 175) (Kabat); GGTFSSY (SEQ ID NO: 176) (Chothia); GGTFSSYAIS (SEQ ID NO: 177) (Extended) | EIIPIFGTASYAQK FQG (SEQ ID NO: 178) (Kabat); IPIFGT (SEQ ID NO: 179) (Chothia) | AGWDDSWFDY (SEQ ID NO: 180) |
| P15D02 | SYWIG (SEQ ID NO: 181) (Kabat); GYSFASY (SEQ ID NO: 182) (Chothia); GYSFASYWIG (SEQ ID NO: 183) (Extended) | VIYPGTSETRYSP SFQG (SEQ ID NO: 184) (Kabat); YPGTSE (SEQ ID NO: 185) (Chothia) | GLSASASGYSFQ Y (SEQ ID NO: 186) |

TABLE 2-continued

| | | | |
|---|---|---|---|
| P16C05 | DYWIG (SEQ ID NO: 187) (Kabat); GYSFTDY (SEQ ID NO: 188) (Chothia); GYSFTDYWIG (SEQ ID NO: 189) (Extended) | MISPGGSTTIYRP SFQG (SEQ ID NO: 190) (Kabat); SPGGST (SEQ ID NO: 191) (Chothia) | MYTGGYGGSWY FDY (SEQ ID NO: 192) |
| 10A1 | YYYWT (SEQ ID NO: 332) (Kabat); GGSISYY (SEQ ID NO: 333) (Chothia); GGSISYYYWT (SEQ ID NO: 334) (Extended) | HIYYSGSTNYNPS LKS (SEQ ID NO: 335) (Kabat); YYSGS (SEQ ID NO: 336) (Chothia) | AEGSIDAFDF (SEQ ID NO: 337) |
| 10E2 | SNYMT (SEQ ID NO: 338) (Kabat); GFTVSSN (SEQ ID NO: 339) (Chothia); GFTVSSNYMT (SEQ ID NO: 340) (Extended) | VIYSGGSTYYADS VKG (SEQ ID NO: 341) (Kabat); YSGGS (SEQ ID NO: 342) (Chothia) | NWGDYW (SEQ ID NO: 343) |
| 11A1 | YYFWN (SEQ ID NO: 344) (Kabat); GGSIDYY (SEQ ID NO: 345) (Chothia); GGSIDYYFWN (SEQ ID NO: 346) (Extended) | HVYDIGNTKYNP SLKS (SEQ ID NO: 347) (Kabat); YDIGN (SEQ ID NO: 348) (Chothia) | GEGAIDAFDI (SEQ ID NO: 349) |
| 11C1 | YYYWT (SEQ ID NO: 350) (Kabat); GGSISYY (SEQ ID NO: 351) (Chothia); GGSISYYYWT (SEQ ID NO: 352) (Extended) | HVIYSGTTNYNPS LKS (SEQ ID NO: 353) (Kabat); IYSGT (SEQ ID NO: 354) (Chothia) | AEGSIDAFDL (SEQ ID NO: 355) |
| 11D1 | DYGIH (SEQ ID NO: 356) (Kabat); GFTFSDY (SEQ ID NO: 357) (Chothia); GFTFSDYGIH (SEQ ID NO: 358) (Extended) | VIWYDGSiKKYSD SVKG (SEQ ID NO: 359) (Kabat); WYDGSi (SEQ ID NO: 360) (Chothia) | DEVGtfGAFDF (SEQ ID NO: 361) |
| 11E1 | SdgYYWS (SEQ ID NO: 362) (Kabat); GGSISSdgY (SEQ ID NO: 363) (Chothia); GGSISSdgYYWS (SEQ ID NO: 364) (Extended) | YMYYSGSTYYNP SLKS (SEQ ID NO: 365) (Kabat); YYSGS (SEQ ID NO: 366) (Chothia) | DFGWYFDL (SEQ ID NO: 367) |
| 12A2 | SdgYYWS (SEQ ID NO: 368) (Kabat); GGSVSSdgY (SEQ ID NO: 369) (Chothia); GGSVSSdgYYWS (SEQ ID NO: 370) (Extended) | YIYYRRITDYNPS LKS (SEQ ID NO: 371) (Kabat); YYRRI (SEQ ID NO: 372) (Chothia) | DFGWYFDL (SEQ ID NO: 373) |
| 12C4 | GYYLH (SEQ ID NO: 374) (Kabat); GYTFTGY (SEQ ID NO: 375) (Chothia); GYTFTGYYLH (SEQ ID NO: 376) (Extended) | WINpNSGGTNYA QKFQG (SEQ ID NO: 377) (Kabat); NpNSGG (SEQ ID NO: 378) (Chothia) | DRGVtmivDGMD D (SEQ ID NO: 379) |
| 12C5 | DYGMH (SEQ ID NO: 380) (Kabat); GFTFSDY (SEQ ID NO: 381) (Chothia); GFTFSDYGMH (SEQ ID NO: 382) (Extended) | VIWYDGSnKYYA DSVKG (SEQ ID NO: 383) (Kabat); WYDGSn (SEQ ID NO: 384) (Chothia) | DEVGfvGAFDI (SEQ ID NO: 385) |
| 12D3 | SdgYYWS (SEQ ID NO: 386) (Kabat); GGSISSdgY (SEQ ID NO: 387) (Chothia); GGSISSdgYYWS (SEQ ID NO: 388) (Extended) | YMYYSGITYHNP SLKS (SEQ ID NO: 389) (Kabat); YYSGI (SEQ ID NO: 390) (Chothia) | DFGWYFDL (SEQ ID NO: 391) |

TABLE 2-continued

| | | | |
|---|---|---|---|
| 12D6 | SdaYYWS (SEQ ID NO: 392) (Kabat); GGSISSdaY (SEQ ID NO: 393) (Chothia); GGSISSdaYYWS (SEQ ID NO: 394) (Extended) | YMYYSGITYYNPSLKS (SEQ ID NO: 395) (Kabat); YYSGI (SEQ ID NO: 396) (Chothia) | DFGWYFDL (SEQ ID NO: 397) |
| 12D7 | DYGIH (SEQ ID NO: 398) (Kabat); GFTFSDY (SEQ ID NO: 399) (Chothia); GFTFSDYGIH (SEQ ID NO: 400) (Extended) | VIWYDGSIKKYSDSVKG (SEQ ID NO: 401) (Kabat); WYDGSi (SEQ ID NO: 402) (Chothia) | DEVGtfGAFDF (SEQ ID NO: 403) |
| 12F5 | NAWMS (SEQ ID NO: 404) (Kabat); GFTFSNA (SEQ ID NO: 405) (Chothia); GFTFSNAWMS (SEQ ID NO: 406) (Extended) | RIKsktGGGTTDYAAPVKG (SEQ ID NO: 407) (Kabat); KsktGGGT (SEQ ID NO: 408) (Chothia) | LIVGaiSLFDY (SEQ ID NO: 409) |
| 12H4 | YYFWT (SEQ ID NO: 410) (Kabat); GGSISYY (SEQ ID NO: 411) (Chothia); GGSISYYFWT (SEQ ID NO: 412) (Extended) | QIYYSGNTNSNPSLKS (SEQ ID NO: 413) (Kabat); YYSGN (SEQ ID NO: 414) (Chothia) | AEGSIDAFDI (SEQ ID NO: 415) |
| 8C8 | SYSMN (SEQ ID NO: 416) (Kabat); GFTFSSY (SEQ ID NO: 417) (Chothia); GFTFSSYSMN (SEQ ID NO: 418) (Extended) | SIStSSNYIHYADSLQG (SEQ ID NO: 419) (Kabat); StSSNY (SEQ ID NO: 420) (Chothia) | DKGTtltnWYFDL (SEQ ID NO: 421) |
| 8F7 | SYGMH (SEQ ID NO: 422) (Kabat); GFTFSSY (SEQ ID NO: 423) (Chothia); GFTFSSYGMH (SEQ ID NO: 424) (Extended) | VIWYDGSnKYYADSLKG (SEQ ID NO: 425) (Kabat); WYDGSn (SEQ ID NO: 426) (Chothia) | DGYSgssDAFDI (SEQ ID NO: 427) |
| 8F8 | YYYWS (SEQ ID NO: 428) (Kabat); GGSISYY (SEQ ID NO: 429) (Chothia); GGSISYYYWS (SEQ ID NO: 430) (Extended) | NINYMGNTIYNPSLKS (SEQ ID NO: 431) (Kabat); NYMGN (SEQ ID NO: 432) (Chothia) | AEGSIDAFDF (SEQ ID NO: 433) |
| 9D8 | GYYIY (SEQ ID NO: 434) (Kabat); GYIFTGY (SEQ ID NO: 435) (Chothia); GYIFTGYYIY (SEQ ID NO: 436) (Extended) | WINpSSGGTNYAQKFQG (SEQ ID NO: 437) (Kabat); NpSSGG (SEQ ID NO: 438) (Chothia) | DRKReyyynFGMDV (SEQ ID NO: 439) |
| 9E10 | SHYIY (SEQ ID NO: 440) (Kabat); GYTFTSH (SEQ ID NO: 441) (Chothia); GYTFTSHYIY (SEQ ID NO: 442) (Extended) | WINpNSGGTNYAQKFQD (SEQ ID NO: 443) (Kabat); NpNSGG (SEQ ID NO: 444) (Chothia) | DRKReyyynFGMDV (SEQ ID NO: 4454) |
| 9E5 | SHYIY (SEQ ID NO: 446) (Kabat); GFTFTSH (SEQ ID NO: 447) (Chothia); GFTFTSHYIY (SEQ ID NO: 448) (Extended) | WINpNSGGTKYAQKFQD (SEQ ID NO: 449) (Kabat); NpNSGG (SEQ ID NO: 450) (Chothia) | DRKReyyynFGMDV (SEQ ID NO: 451) |
| 9F4 | IYAIH (SEQ ID NO: 452) (Kabat); GFTLSIY (SEQ ID NO: 453) (Chothia); GFTLSIYAIH (SEQ ID NO: 454) (Extended) | SFGgRGSSTYFADSVKG (SEQ ID NO: 455) (Kabat); GgRGSS (SEQ ID NO: 456) (Chothia) | EKDWgRGFDY (SEQ ID NO: 457) |

TABLE 2-continued

| 9F8 | NYSMN (SEQ ID NO: 458) (Kabat); GFTFSNY (SEQ ID NO: 459) (Chothia); GFTFSNYSMN (SEQ ID NO: 460) (Extended) | SISsSTIYIYYADS VKG (SEQ ID NO: 461) (Kabat); SsSTIY (SEQ ID NO: 462) (Chothia) | DIGWevftLGFDY (SEQ ID NO: 463) |

Light Chain

| mAb | CDRL1 | CDRL2 | CDRL3 |
|---|---|---|---|
| 31H1 | RSSQSLVHSDGNTYLS (SEQ ID NO: 193); | KISNRFS (SEQ ID NO: 194) | MQATQFPLT (SEQ ID NO: 195) |
| 63B2 | RSSQSLVHSDGNTYLS (SEQ ID NO: 196); | KISNRFS (SEQ ID NO: 197) | MQATQFPLT (SEQ ID NO: 198) |
| 40E3 | RASQGISNYLA (SEQ ID NO: 199); | AASSLQS (SEQ ID NO: 200) | QQYNSYPLT (SEQ ID NO: 201) |
| 42C3 | RSSQSLVYSDENTYLN (SEQ ID NO: 202); | QVSNRDS (SEQ ID NO: 203) | MQGTYWPPT (SEQ ID NO: 204) |
| 45F11 | RASQSVSSSLA (SEQ ID NO: 205); | GASTRAT (SEQ ID NO: 206) | QQYINWPH (SEQ ID NO: 207) |
| 64F9 | QASQDISNYLN (SEQ ID NO: 208); | GASNLET (SEQ ID NO: 209) | QQYDNFPIT (SEQ ID NO: 210) |
| 72C2 | RASQSVSSNLA (SEQ ID NO: 211); | SASTRAS (SEQ ID NO: 212) | QQYDNWPPLT (SEQ ID NO: 213) |
| 2F10 | RASQSVSSSYLA (SEQ ID NO: 214); | GASSRAT (SEQ ID NO: 215) | QQYGSSPLT (SEQ ID NO: 216) |
| 4F11 | RASQDISNYLA (SEQ ID NO: 217); | AASSLQS (SEQ ID NO: 218) | LQLNSFPFT (SEQ ID NO: 219) |
| 10H10 | RASQGISSWLA (SEQ ID NO: 220); | AASSLQS (SEQ ID NO: 221) | QQAFSFPFT (SEQ ID NO: 222) |
| 17G6 | KSSQSVLYSYNNKNYVA (SEQ ID NO: 223); | WASTRES (SEQ ID NO: 224) | QQYYSTLT (SEQ ID NO: 225) |
| 65E11 | RASQSVSSSYLA (SEQ ID NO: 226); | DASSRAT (SEQ ID NO: 227) | QQYGSSPLT (SEQ ID NO: 228) |
| P02B10 | SGSSSNIGSNYVY (SEQ ID NO: 229); | RNNQRPS (SEQ ID NO: 230) | AAWDDSLSGVV (SEQ ID NO: 231) |
| P07D03 | SGSRSNIGSNYVY (SEQ ID NO: 232); | RNNQRPS (SEQ ID NO: 233) | ASWDGSLSAVV (SEQ ID NO: 234) |
| P08A02 | SGSSSNIGSNYVY (SEQ ID NO: 235); | RNNQRPS (SEQ ID NO: 236) | ATWDDSLGSPV (SEQ ID NO: 237) |
| P08E02 | RASQSISRYLN (SEQ ID NO: 238); | AASILQT (SEQ ID NO: 239) | QQSYSTTMWT (SEQ ID NO: 240) |
| P08F08 | SGSSSNIGSNYVN (SEQ ID NO: 241); | GDYQRPS (SEQ ID NO: 242) | ATRDDSLSGSVV (SEQ ID NO: 243) |
| P08G02 | RASQSIYDYLH (SEQ ID NO: 244); | DASNLQS (SEQ ID NO: 245) | QQSYTTPLFT (SEQ ID NO: 246) |
| P12809 | RASQYIGRYLN (SEQ ID NO: 247); | GATSLAS (SEQ ID NO: 248) | QQSYSTTSPT (SEQ ID NO: 249) |
| P12F02 | SGSTSNIGRNYVY (SEQ ID NO: 250); | RTNQRPS (SEQ ID NO: 251) | AAWDDSLSGRV (SEQ ID NO: 252) |
| P12G07 | SGSSSNIGSNYVY (SEQ ID NO: 253); | MNNQRPS (SEQ ID NO: 254) | AAWDDSLSAVV (SEQ ID NO: 255) |
| P13F04 | SGSNSNIGTNYVS (SEQ ID NO: 256); | RSSRRPS (SEQ ID NO: 257) | AAWDGSLSGHWV (SEQ ID NO: 258) |

TABLE 2-continued

| | | | |
|---|---|---|---|
| P15D02 | RASQSIDTYLN (SEQ ID NO: 259); | SASSLHS (SEQ ID NO: 260) | QQSYSTTAWT (SEQ ID NO: 261) |
| P16C05 | RASQSIGQSLN (SEQ ID NO: 262); | GASSLQS (SEQ ID NO: 263) | QQSYSTPIT (SEQ ID NO: 264) |
| 10A1 | RASQSISTWLA (SEQ ID NO: 464); | KASSLES (SEQ ID NO: 465) | QQYKSYSHT (SEQ ID NO: 466) |
| 10E2 | RASQSISSWLA (SEQ ID NO: 467); | KASSLES (SEQ ID NO: 468) | QQYKSFSLT (SEQ ID NO: 469) |
| 11A1 | RASQSISSWLA (SEQ ID NO: 470); | KASTLES (SEQ ID NO: 471) | QQYNSYSYT (SEQ ID NO: 472) |
| 11C1 | RASQSVSSWLA (SEQ ID NO: 473); | KASSLES (SEQ ID NO: 474) | QQYNTYSHT (SEQ ID NO: 475) |
| 11D1 | RASQGIRNDLG (SEQ ID NO: 476); | AASSLQS (SEQ ID NO: 477) | LQDYNYPFT (SEQ ID NO: 478) |
| 11E1 | RASQDIDNYLA (SEQ ID NO: 479); | AASALQS (SEQ ID NO: 480) | QNYNSGPRT (SEQ ID NO: 481) |
| 12A2 | RASQDISNYLT (SEQ ID NO: 482); | AASALQS (SEQ ID NO: 483) | QNYNSAPRT (SEQ ID NO: 484) |
| 12C4 | RSSQSLLHSNGYNYLD (SEQ ID NO: 485); | LGSNRAS (SEQ ID NO: 486) | MQTLQTPFT (SEQ ID NO: 487) |
| 12C5 | RASQGINSHLA (SEQ ID NO: 488); | YASTLPS (SEQ ID NO: 489) | QQLNHYPIT (SEQ ID NO: 490) |
| 12D3 | RASQGISNYLA (SEQ ID NO: 491); | AASTLHS (SEQ ID NO: 492) | QKYNSAPRT (SEQ ID NO: 493) |
| 12D6 | RASQDISNYLA (SEQ ID NO: 494); | AASTLHS (SEQ ID NO: 495) | QKYNSAPRT (SEQ ID NO: 496) |
| 12D7 | RASQDISSFLA (SEQ ID NO: 497); | VASTLQS (SEQ ID NO: 498) | QQLHVYPIT (SEQ ID NO: 499) |
| 12F5 | RSSQSLLDSDDGNtYLD (SEQ ID NO: 500) | TLSYRAS (SEQ ID NO: 501) | MQRIEFPFT (SEQ ID NO: 502) |
| 12H4 | RASQTISTWLA (SEQ ID NO: 503); | KASNLES (SEQ ID NO: 504) | QQYQTFSHT (SEQ ID NO: 505) |
| 8C8 | RASQGISNYLA (SEQ ID NO: 506); | AASTLQS (SEQ ID NO: 507) | QKYNSAPLT (SEQ ID NO: 508) |
| 8F7 | RSSQTLVHSNGYNYLN (SEQ ID NO: 509) | LGSNRAS (SEQ ID NO: 510) | MQAIQTPYT (SEQ ID NO: 511) |
| 8F8 | RASQSISSWLA (SEQ ID NO: 512); | KASNLES (SEQ ID NO: 513) | QQYNSYSCT (SEQ ID NO: 514) |
| 9D8 | QASQDINNYLH (SEQ ID NO: 515); | DASDWET (SEQ ID NO: 516) | QQYDHLPIT (SEQ ID NO: 517) |
| 9E10 | QASQDISNYLH (SEQ ID NO: 518); | DASDLET (SEQ ID NO: 519) | QQYDHLPIT (SEQ ID NO: 520) |
| 9E5 | QASQDISNYLH (SEQ ID NO: 521); | DASDLET (SEQ ID NO: 522) | QQYDHLPIT (SEQ ID NO: 523) |
| 9F4 | QASQDISNYLN (SEQ ID NO: 524); | DASNLET (SEQ ID NO: 525) | QQYDNLPYT (SEQ ID NO: 526) |
| 9F8 | RSSQSLLYSNGYNYLD (SEQ ID NO: 527); | LNSNRAS (SEQ ID NO: 528) | MQALQTPLT (SEQ ID NO: 529) |

In some embodiments, the present invention provides an antibody that binds to CD70 and competes with the antibody as described herein, including 31H1, 6362, 40E3, 42C3, 45F11, 64F9, 72C2, 2F10, 4F11, 10H10, 17G6, 65E11, P02B10, P07D03, P08A02, P08E02, P08F08, P08G02, P12B09, P12F02, P12G07, P13F04, P15D02, P16C05, 10A1, 10E2, 11A1, 11C1, 11D1, 11E1, 12A2, 12C4, 12C5, 12D3, 12D6, 12D7, 12F5, 12H4, 8C8, 8F7, 8F8, 9D8, 9E10, 9E5, 9F4 or 9F8.

In some embodiments, the invention also provides CDR portions of antibodies to CD70 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity (Ko) of the CD70 antibody as described herein to CD70 (such as human CD70 (e.g., (SEQ ID NO: 278)) can be about 0.001 to about 5000 nM. In some embodiments, the binding affinity is about any of 5000 nM, 4500 nM, 4000 nM, 3500 nM, 3000 nM, 2500 nM, 2000 nM, 1789 nM, 1583 nM, 1540 nM, 1500 nM, 1490 nM, 1064 nM, 1000 nM, 933 nM, 894 nM, 750 nM, 705 nM, 678 nM, 532 nM, 500 nM, 494 nM, 400 nM, 349 nM, 340 nM, 353 nM, 300 nM, 250 nM, 244 nM, 231 nM, 225 nM, 207 nM, 200 nM, 186 nM, 172 nM, 136 nM, 113 nM, 104 nM, 101 nM, 100 nM, 90 nM, 83 nM, 79 nM, 74 nM, 54 nM, 50 nM, 45 nM, 42 nM, 40 nM, 35 nM, 32 nM, 30 nM, 25 nM, 24 nM, 22 nM, 20 nM, 19 nM, 18 nM, 17 nM, 16 nM, 15 nM, 12 nM, 10 nM, 9 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.001 nM. In some embodiments, the binding affinity is less than about any of 5000 nM, 4000 nM, 3000 nM, 2000 nM, 1000 nM, 900 nM, 800 nM, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

Bispecific antibodies, monoclonal antibodies that have binding specificities for at least two different antigens, can be prepared using the antibodies disclosed herein. Methods for making bispecific antibodies are known in the art (see, e.g., Suresh et al., Methods in Enzymology 121:210, 1986). Traditionally, the recombinant production of bispecific antibodies was based on the coexpression of two immunoglobulin heavy chain-light chain pairs, with the two heavy chains having different specificities (Millstein and Cuello, Nature 305, 537-539, 1983). Accordingly, in one aspect, provided is a bispecific antibody wherein the bispecific antibody is a full-length human antibody, comprising a first antibody variable domain of the bispecific antibody specifically binding to a target antigen (e.g., CD70), and comprising a second antibody variable domain of the bispecific antibody capable of recruiting the activity of a human immune effector cell by specifically binding to an effector antigen located on the human immune effector cell.

The human immune effector cell can be any of a variety of immune effector cells known in the art. For example, the immune effector cell can be a member of the human lymphoid cell lineage, including, but not limited to, a T cell (e.g., a cytotoxic T cell), a B cell, and a natural killer (NK) cell. The immune effector cell can also be, for example without limitation, a member of the human myeloid lineage, including, but not limited to, a monocyte, a neutrophilic granulocyte, and a dendritic cell. Such immune effector cells may have either a cytotoxic or an apoptotic effect on a target cell or other desired effect upon activation by binding of an effector antigen.

The effector antigen is an antigen (e.g., a protein or a polypeptide) that is expressed on the human immune effector cell. Examples of effector antigens that can be bound by the heterodimeric protein (e.g., a heterodimeric antibody or a bispecific antibody) include, but are not limited to, human CD3 (or CD3 (Cluster of Differentiation) complex), CD16, NKG2D, NKp46, CD2, CD28, CD25, CD64, and CD89.

The target cell can be a cell that is native or foreign to humans. In a native target cell, the cell may have been transformed to be a malignant cell or pathologically modified (e.g., a native target cell infected with a virus, a *plasmodium*, or a bacterium). In a foreign target cell, the cell is an invading pathogen, such as a bacterium, a *plasmodium*, or a virus.

The target antigen is expressed on a target cell in a diseased condition (e.g., an inflammatory disease, a proliferative disease (e.g., cancer), an immunological disorder, a neurological disease, a neurodegenerative disease, an autoimmune disease, an infectious disease (e.g., a viral infection or a parasitic infection), an allergic reaction, a graft-versus-host disease or a host-versus-graft disease). A target antigen is not effector antigen. In some embodiments, the target antigen is CD70.

In some embodiments, provided is a bispecific antibody, wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises a heavy chain variable (VH) region comprising a VH CDR1, VH CDR2, and VH CDR3 of the VH sequence shown in SEQ ID NO: 2, 4, 6, 8, 10, 12, 14, 16, 18, 20, 22, 24, 26, 28, 30, 32, 34, 36, 38, 40, 42, 44, 46, 48, 289, 291, 293, 295, 297, 299, 301, 303, 305, 307, 309, 311, 313, 315, 317, 319, 321, 323, 325, 327, 329 or 331; or a light chain variable (VL) region comprising VL CDR1, VL CDR2, and VL CDR3 of the VL sequence shown in SEQ ID NO: 1, 3, 5, 7, 9, 11, 13, 15, 17, 19, 21, 23, 25, 27, 29, 31, 33, 35, 37, 39, 41, 43, 45, 47, 288, 290, 292, 294, 296, 298, 300, 302, 304, 306, 308, 310, 312, 314, 316, 318, 320, 322, 324, 326, 328 or 330.

In some embodiments, provided is a bispecific antibody, wherein the bispecific antibody is a full-length antibody, comprising a first antibody variable domain of the bispecific antibody specifically binding to a target antigen, and comprising a second antibody variable domain of the bispecific antibody capable of recruiting the activity of a human immune effector cell by specifically binding to an effector antigen located on the human immune effector cell, wherein the first antibody variable domain comprises (a) a heavy chain variable (VH) region comprising (i) a VH complementarity determining region one (CDR1) comprising the sequence shown in SEQ ID NO: 49, 50, 51, 55, 56, 57, 61, 62, 63, 67, 68, 69, 73, 74, 75, 79, 80, 81, 85, 86, 87, 91, 92, 93, 97, 98, 99, 103, 104, 105, 109, 110, 111, 115, 116, 117, 121, 122, 123, 127, 128, 129, 133, 134, 135, 139, 140, 141, 145, 146, 147, 151, 152, 153, 157, 158, 159, 163, 164, 165, 169, 170, 171, 175, 176, 177, 181, 182, 183, 187, 188, 189, 332, 333, 334, 338, 339, 340, 344, 345, 346, 350, 351, 352, 356, 357, 358, 362, 363, 364, 368, 369, 370, 374, 375, 376, 380, 381, 382, 386, 387, 388, 392, 393, 394, 398, 399, 400, 404, 405, 406, 410, 411, 412, 416, 437, 418, 422, 423, 424, 428, 429, 430, 434, 435, 436, 440, 441, 442, 446, 447, 448, 452, 453, 454, 458, 459 or 460; (ii) a VH CDR2 comprising the sequence shown in SEQ ID NO: 52, 53, 58, 59, 64, 65, 70, 71, 76, 77, 82, 83, 88, 89, 94, 95, 100, 101, 106, 107, 112, 113, 118, 119, 124, 125, 130, 131, 136, 137, 142, 143, 148, 149, 154, 155, 160, 161, 166, 167, 172, 173, 178, 179, 184, 185, 190, 191, 335, 336, 341, 342, 347, 348, 353, 354, 359, 360, 365, 366, 371, 372, 377, 378, 383, 384, 389, 390, 395, 396, 401, 402, 407, 408, 413, 414, 419, 420, 425, 426, 431, 432, 437, 438, 443, 444, 449, 450, 455, 456, 461 or 462; and iii) a VH CDR3 comprising the sequence shown in SEQ ID NO: 54, 60, 66, 72, 78, 84, 90, 96, 102, 108, 114, 120, 126, 132, 138, 144, 150, 156, 162, 168, 174, 180, 186, 192, 337, 343, 349, 355, 361, 367, 373, 379, 385, 391, 397, 403, 409, 415, 421, 427, 433, 439, 445, 451, 457 or 463; or a light chain variable (VL) region comprising (i) a VL CDR1 comprising the sequence shown in SEQ ID NO: 193, 196, 199, 202, 205, 208, 211, 214, 217, 220, 223, 226, 229, 232, 235, 238, 241, 244, 247, 250, 253, 256, 259, 262, 464, 467, 470, 473, 476, 479, 482, 485, 488, 491, 494, 497, 500, 503, 506, 509, 512, 515, 518, 521, 524 or 527; (ii) a VL CDR2 comprising the sequence shown in SEQ ID NO: 194, 197, 200, 203, 206, 209, 212, 215, 218, 221, 224, 227, 230, 233, 236, 239, 242, 245, 248, 251, 254, 257, 260, 263, 465, 468, 471, 474, 477, 480, 483, 486, 489, 492, 495, 498, 501, 504, 507, 510, 513, 516, 519, 522, 525 or 528; and (iii) a VL CDR3 comprising the sequence shown in SEQ ID NO: 195, 198, 201, 204, 207, 210, 213, 216, 219, 222, 225, 228, 231, 234, 237, 240, 243, 246, 249, 252, 255, 258, 261, 264, 466, 469, 472, 475, 478, 481, 484, 487, 490, 493, 496, 499, 502, 505, 508, 511, 514, 517, 520, 523, 526 or 529.

In some embodiments, the second antibody variable domain comprises a heavy chain variable (VH) region comprising a VH CDR1, VH CDR2, and VH CDR3 of the VH sequence shown in SEQ ID NO: 266; or a light chain variable (VL) region comprising VL CDR1, VL CDR2, and VL CDR3 of the VL sequence shown in SEQ ID NO: 265.

In some embodiments, the second antibody variable domain comprises (a) a heavy chain variable (VH) region comprising (i) a VH complementary determining region one (CDR1) comprising the sequence shown in SEQ ID NO: 267, 268, or 269; (ii) a VH CDR2 comprising the sequence shown in SEQ ID NO: 270 or 271; and iii) a VH CDR3 comprising the sequence shown in SEQ ID NO: 272; or (b) a light chain variable (VL) region comprising (i) a VL CDR1 comprising the sequence shown in SEQ ID NO: 273; (ii) a VL CDR2 comprising the sequence shown in SEQ ID NO: 274; and (iii) a VL CDR3 comprising the sequence shown in SEQ ID NO: 275.

Table 3 shows the specific amino acid and nucleic acid sequences of the second antibody variable domain, which is specific to CD3. In Table 3, the underlined sequences are CDR sequences according to Kabat and in bold according to Chothia.

TABLE 3

| mAb | Light Chain | Heavy Chain |
| --- | --- | --- |
| h2B4_HNPS_VL_TK | DIVMTQSPDSLAVSLGERATINC KSSQSLFNVRSRKNYLAWYQQK PGQPPKLLISWASTRESGVPDRF SGSGSGTDFTLTISSLQAEDVAV YYCKQSYDLFTFGSGTKLEIK (SEQ ID NO: 265) | EVQLVESGGGLVQPGGSLRLSCA ASGFTFSDYYMTWVRQAPGKGLE WVAFIRNRARGYTSDHNPSVKGR FTISRDNAKNSLYLQMNSLRAEDT AVYYCARDRPSYYVLDYWGQGTT VTVSS (SEQ ID NO: 266) |
| h2B4_HNPS_VL_TK | GACATTGTGATGACTCAATCCC CCGACTCCCTGGCTGTGTCCCT CGGCGAACGCGCAACTATCAAC TGTAAAAGCAGCCAGTCCCTGT TCAACGTCCGGTCGAGGAAGAA CTACCTGGCCTGGTATCAGCAG AAACCTGGGCAGCCGCCGAAG CTTCTGATCTCATGGGCCTCAA CTCGGGAAAGCGGAGTGCCAG ATAGATTCTCCGGATCTGGCTC CGGAACCGACTTCACCCTGACG ATTTCGAGCTTGCAAGCGGAGG ATGTGGCCGTGTACTACTGCAA GCAGTCCTACGACCTCTTCACC TTTGGTTCGGGCACCAAGCTGG AGATCAAA (SEQ ID NO: 276) | GAAGTCCAACTTGTCGAATCGGG AGGAGGCCTTGTGCAACCCGGT GGATCCCTGAGGCTGTCATGCG CGGCCTCGGGCTTCACCTTTTCC GATTACTACATGACCTGGGTCAG ACAGGCCCCTGGAAAGGGGTTG GAATGGGTGGCATTCATCCGGA ATAGAGCCCGCGGATACACTTCC GACCACAACCCCAGCGTGAAGG GGCGGTTCACCATTAGCCGCGA CAACGCCAAGAACTCCCTCTACC TCCAAATGAACAGCCTGCGGGC GGAGGATACCGCTGTGTACTACT GCGCCCGCGACCGGCCGTCCTA CTATGTGCTGGACTACTGGGGC CAGGGTACTACGGTCACCGTCT CCTCA (SEQ ID NO: 277) |

Table 4 shows the examples of CDR sequences of the second antibody variable domain, which is specific to CD3.

TABLE 4

| Heavy Chain | | | |
|---|---|---|---|
| mAb | CDRH1 | CDRH2 | CDRH3 |
| h2B4_HNPS_VL_TK | SDYYMT (SEQ ID NO: 267) (Kabat); GFTFSDY (SEQ ID NO: 268) (Chothia); GFTFSDYYMT (SEQ ID NO: 269) (Extended) | RNRARGYT (SEQ ID NO: 270) (Kabat) FIRNRARGYTSDHNPSVKG (SEQ ID NO: 271) (Extended) | DRPSYYVLDY (SEQ ID NO: 272) |

| Light Chain | | | |
|---|---|---|---|
| mAb | CDRH1 | CDRH2 | CDRH3 |
| h2B4_HNPS_VL_TK | KSSQSLFNVRSRKNYLA (SEQ ID NO: 273) | WASTRES (SEQ ID NO: 274) | KQSYDLFT (SEQ ID NO: 275) |

In some embodiments, a bispecific antibody provided herein which contains a CD3-specific variable domain having an anti-CD3 sequence as provided in U.S. Publication No. 20160297885, which is hereby incorporated by reference for all purposes.

According to one approach to making bispecific antibodies, antibody variable domains with the desired binding specificities (antibody-antigen combining sites) are fused to immunoglobulin constant region sequences. The fusion preferably is with an immunoglobulin heavy chain constant region, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In another approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690.

In another approach, the bispecific antibodies are composed of amino acid modification in the first hinge region in one arm, and the substituted/replaced amino acid in the first hinge region has an opposite charge to the corresponding amino acid in the second hinge region in another arm. This approach is described in International Patent Application No. PCT/US2011/036419 (WO2011/143545).

In another approach, the formation of a desired heteromultimeric or heterodimeric protein (e.g., bispecific antibody) is enhanced by altering or engineering an interface between a first and a second immunoglobulin-like Fc region (e.g., a hinge region or a CH3 region). In this approach, the bispecific antibodies may be composed of a CH3 region, wherein the CH3 region comprises a first CH3 polypeptide and a second CH3 polypeptide which interact together to form a CH3 interface, wherein one or more amino acids within the CH3 interface destabilize homodimer formation and are not electrostatically unfavorable to homodimer formation. This approach is described in International Patent Application No. PCT/US2011/036419 (WO2011/143545).

In another approach, the bispecific antibodies can be generated using a glutamine-containing peptide tag engineered to the antibody directed to an epitope (e.g., CD70) in one arm and another peptide tag (e.g., a Lys-containing peptide tag or a reactive endogenous Lys) engineered to a second antibody directed to a second epitope in another arm in the presence of transglutaminase. This approach is described in International Patent Application No. PCT/IB2011/054899 (WO2012/059882).

In some embodiments, the heterodimeric protein (e.g., bispecific antibody) as described herein comprises a full-length human antibody, wherein a first antibody variable domain of the bispecific antibody specifically binding to a target antigen (e.g., CD70), and comprising a second antibody variable domain of the bispecific antibody capable of recruiting the activity of a human immune effector cell by specifically binding to an effector antigen (e.g., CD3) located on the human immune effector cell, wherein the first and second antibody variable domain of the heterodimeric protein comprise amino acid modifications at positions 223, 225, and 228 (e.g., (C223E or C223R), (E225E or E225R), and (P228E or P228R)) in the hinge region and at position 409 or 368 (e.g., K409R or L368E (EU numbering scheme)) in the CH3 region of human IgG2 (SEQ ID NO: 279).

In some embodiments, the first and second antibody variable domains of the heterodimeric protein comprise amino acid modifications at positions 221 and 228 (e.g., (D221R or D221E) and (P228R or P228E)) in the hinge region and at position 409 or 368 (e.g., K409R or L368E (EU numbering scheme)) in the CH3 region of human IgG1 (SEQ ID NO: 280).

In some embodiments, the first and second antibody variable domains of the heterodimeric protein comprise amino acid modifications at positions 228 (e.g., (P228E or P228R)) in the hinge region and at position 409 or 368 (e.g., R409 or L368E (EU numbering scheme)) in the CH3 region of human IgG4 (SEQ ID NO: 281).

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the CD70 monospecific antibody or the CD70 bispecific antibody (e.g., CD70-CD3) as described herein is a monoclonal antibody. For example, the CD70 monospecific antibody is a human monoclonal antibody. In another example, the CD70 arm of the CD70-CD3 bispecific antibody is a human monoclonal antibody, and the CD3 arm of the CD70-CD3 bispecific antibody is a humanized monoclonal antibody.

In some embodiments, the antibody comprises a modified constant region, such as, for example without limitation, a constant region that has increased potential for provoking an immune response. For example, the constant region may be modified to have increased affinity to an Fc gamma receptor such as, e.g., FcγRI, FcγRIIA, or FcγRIII.

In some embodiments, the antibody comprises a modified constant region, such as a constant region that is immunologically inert, that is, having a reduced potential for provoking an immune response. In some embodiments, the constant region is modified as described in Eur. J. Immunol., 29:2613-2624, 1999; PCT Application No. PCT/GB99/01441; or UK Patent Application No. 98099518. The Fc can be human IgG1, human IgG2, human IgG3, or human IgG4. The Fc can be human IgG2 containing the mutation A330P331 to S330S331 (IgG2Δa), in which the amino acid residues are numbered with reference to the wild type IgG2 sequence. Eur. J. Immunol., 29:2613-2624, 1999. In some embodiments, the antibody comprises a constant region of IgG4 comprising the following mutations (Armour et al., Molecular Immunology 40 585-593, 2003): E233F234L235 to P233V234A235 (IgG4Δc), in which the numbering is with reference to wild type IgG4. In yet another embodiment, the Fc is human IgG4 E233F234L235 to P233V234A235 with deletion G236 (IgG4Δb). In another embodiment, the Fc is any human IgG4 Fc (IgG4, IgG4Δb or IgG4Δc) containing hinge stabilizing mutation S228 to P228 (Aalberse et al., Immunology 105, 9-19, 2002). In another embodiment, the Fc can be aglycosylated Fc.

In some embodiments, the constant region is aglycosylated by mutating the oligosaccharide attachment residue (such as Asn297) or flanking residues that are part of the glycosylation recognition sequence in the constant region. In some embodiments, the constant region is aglycosylated for N-linked glycosylation enzymatically. The constant region may be aglycosylated for N-linked glycosylation enzymatically or by expression in a glycosylation deficient host cell.

In some embodiments, the constant region has a modified constant region that removes or reduces Fc gamma receptor binding. For example, the Fc can be human IgG2 containing the mutation D265, in which the amino acid residues are numbered with reference to the wild type IgG2 sequence (SEQ ID NO: 279). Accordingly, in some embodiments, the constant region has a modified constant region having the sequence shown in SEQ ID NO: 282: ASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTVERKCRVRCPRCPAPPVAGPSV FLFPPKPKDTLMISRTPEVTCVVVAVSHEDPEVQFNVVYVDGVEVHNAKTKPREEQFNSTF RWSVLTVLHQDWLNGKEYKCKVSNKGLPSSIEKTISKTKGQPREPQVYTLPPSREEMTK NQVSLTCLVKGFYPSDIAVEWESNGQPENNYKTTPPMLDSDGSFFLYSRLTVDKSRWQQ GNVFSCSVMHEALHNHYTQKSLSLSPGK. And the nucleic acid encoding the sequence shown in SEQ ID NO: 282 is shown in SEQ ID NO: 283.

In some embodiments, the constant region has a modified constant region having the sequence shown in SEQ ID NO: 284: ASTKGPSVFPLAPCSRSTSESTAALGCLVKDYFPEPVTVSWNSGALTSGVHTFPAVLQSS GLYSLSSVVTVPSSNFGTQTYTCNVDHKPSNTKVDKTVERKCEVECPECPAPPVAGPSV FLFPPKPKDTLMISRTPEVTCVVVAVSHEDPEVQFNVVYVDGVEVHNAKTKPREEQFNSTF RWSVLTWHQDWLNGKEYKCKVSNKGLPSSIEKTISKTKGQPREPQVYTLPPSREEMTK NQVSLTCEVKGFYPSDIAVEWESNGQPENNYKTTPPMLDSDGSFFLYSKLTVDKSRWQQ GNVFSCSVMHEALHNHYTQKSLSLSPGK. And the nucleic acid encoding the sequence shown in SEQ ID NO: 284 is shown in SEQ ID NO: 285.

The amino acid of the human Kappa constant region is shown in SEQ ID NO: 286: GTVAAPSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC.
And the nucleic acid encoding the sequence of SEQ ID NO: 286 is shown in SEQ ID NO: 287.

One way of determining binding affinity of antibodies to CD70 is by measuring binding affinity of the bivalent antibody to monomeric CD70 protein. The affinity of an CD70 antibody can be determined by surface plasmon resonance (Biacore™3000™ surface plasmon resonance (SPR) system, Biacore™, INC, Piscataway N.J.) equipped with pre-immobilized anti-mouse Fc or anti-human Fc using HBS-EP running buffer (0.01M HEPES, pH 7.4, 0.15 NaCl, 3 mM EDTA, 0.005% v/v Surfactant P20). Monomeric 8-histidine tagged human CD70 extracellular domain (SEQ ID NO: 530) can be diluted into HBS-EP buffer to a concentration of less than 0.5 μg/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound CD70 protein while keeping the activity of CD70 antibodies on the chip for over 200 injections. Typically, serial dilutions (spanning concentrations of 0.1-10× estimated Ko) of purified 8-histidine tagged CD70 samples (SEQ ID NO: 530) are injected for 1 min at 100 μL/minute and dissociation times of up to 2 hours are allowed. The concentrations of the CD70 proteins are determined by absorbance at 280 nm based on sequence specific extinction coefficient of the 8-histidine tagged CD70 protein (SEQ ID NO: 530). Kinetic association rates ($k_{on}$ or $k_a$) and dissociation rates ($k_{off}$ or $k_d$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant (Ko) values are calculated as $k_{off}/k_{on}$. This protocol is suitable for use in determining binding affinity of an antibody to any monomeric CD70, including human CD70, CD70 of another mammal (such as mouse CD70, rat CD70, or primate CD70), as well as different forms of CD70 (e.g., glycosylated CD70). Binding affinity of an antibody is generally measured at 25° C., but can also be measured at 37° C.

The antibodies as described herein may be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for CD70, or portions thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with cells expressing human CD70, a human CD70 protein, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups, can yield a population of antibodies (e.g., monoclonal antibodies).

If desired, the antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In an alternative, the polynucleotide sequence may be used for genetic manipulation to "humanize" the antibody or to improve the affinity, or other characteristics of the antibody. For example, the constant region may be engineered to more nearly resemble human constant regions to avoid immune response if the antibody is used in clinical trials and treatments in humans. It may be desirable to genetically manipulate the antibody sequence to obtain greater affinity to CD70 and greater efficacy in inhibiting CD70.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen binding site derived from a non-human immunoglobulin have been described, including chimeric antibodies having rodent or modified rodent V regions and their associated CDRs fused to human constant regions. See, for example, Winter et al. Nature 349:293-299, 1991, Lobuglio et al. Proc. Nat. Acad. Sci. USA 86:4220-4224, 1989, Shaw et al. J Immunol. 138:4534-4538, 1987, and Brown et al. Cancer Res. 47:3577-3583, 1987. Other references describe rodent CDRs grafted into a human supporting framework region (FR) prior to fusion with an appropriate human antibody constant region. See, for example, Riechmann et al. Nature 332:323-327, 1988, Verhoeyen et al. Science 239:1534-1536, 1988, and Jones et al. Nature 321: 522-525, 1986. Another reference describes rodent CDRs supported by recombinantly engineered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476, 1991, and in U.S. Pat. Nos. 6,180,377; 6,054,297; 5,997,867; 5,866,692; 6,210, 671; and 6,350,861; and in PCT Publication No. WO 01/27160.

The general principles related to humanized antibodies discussed above are also applicable to customizing antibodies for use, for example, in dogs, cats, primate, equines and bovines. Further, one or more aspects of humanizing an antibody described herein may be combined, e.g., CDR grafting, framework mutation and CDR mutation.

In one variation, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455, 1994. Alternatively, the phage display technology (McCafferty et al., Nature 348:552-553, 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571, 1993. Several sources of V-gene segments can be used for phage display. Clackson et al., Nature 352:624-628, 1991, isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597, 1991, or Griffith et al., EMBO J. 12:725-734, 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." (Marks et al., Bio/Technol. 10:779-783, 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266, 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen binding site, i.e., the epitope governs (imprints) the choice of partner. When the process is repeated in order to replace the remaining rodent V domain, a human antibody is obtained (see PCT Publication No. WO 93/06213). Unlike traditional humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar Int. Rev. Immunol 13:65, 1995; and Pollock, et al., J Immunol Methods 231:147, 1999. Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for CD70, or tumor antigens of interest.

The antibodies as described herein can be bound to many different carriers. Carriers can be active or inert. Examples of well-known carriers include polypropylene, polystyrene, polyethylene, dextran, nylon, amylases, glass, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO87/04462. The DNA also may be modified, for example, by substituting the coding sequence for human heavy and light chain constant regions in place of the homologous murine sequences, Morrison et al., Proc. Nat. Acad. Sci. 81:6851, 1984, or by covalently joining to the immunoglobulin coding sequence all or part of the coding sequence for a non-immunoglobulin polypeptide. In that manner, "chimeric" or "hybrid" antibodies are prepared that have the binding specificity of a monoclonal antibody herein.

The CD70 antibodies as described herein can be identified or characterized using methods known in the art, whereby reduction of CD70 expression levels are detected or measured. In some embodiments, an CD70 antibody is identified by incubating a candidate agent with CD70 and monitoring binding or attendant reduction of CD70 expression levels. The binding assay may be performed with purified CD70 polypeptide(s), or with cells naturally expressing, or transfected to express, CD70 polypeptide(s). In one embodiment, the binding assay is a competitive binding assay, where the ability of a candidate antibody to compete with a known CD70 antibody for CD70 binding is evaluated. The assay may be performed in various formats, including the ELISA format.

Following initial identification, the activity of a candidate CD70 antibody can be further confirmed and refined by bioassays, known to test the targeted biological activities. Alternatively, bioassays can be used to screen candidates directly. Some of the methods for identifying and characterizing antibodies are described in detail in the Examples.

CD70 antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an CD70 or other tumor antigen antibody. In another example, the epitope to which the CD70 antibody binds can be determined in a systematic screening by using overlapping peptides derived from the CD70 sequence and determining binding by the CD70 antibody. According to the gene fragment expression assays, the open reading frame encoding CD70 is fragmented either randomly or by specific genetic constructions and the reactivity of the expressed fragments of CD70 with the antibody to be tested is determined. The gene fragments may, for example, be produced by PCR and then transcribed and translated into protein in vitro, in the presence of radioactive amino acids. The binding of the antibody to the radioactively labeled CD70 is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, or necessary for epitope binding. For example, domain swapping experiments can be performed using a mutant CD70 in which various fragments of the CD70 protein have been replaced (swapped) with sequences from CD70 from another species (e.g., mouse), or a closely related, but antigenically distinct protein. By assessing binding of the antibody to the mutant CD70, the importance of the particular CD70 fragment to antibody binding can be assessed. In the case of CD70 specific antibody (i.e. antibody that does not bind CD70 wt (wild type) or any other proteins), epitope can be deduced from the sequence alignment of CD70 to CD70 wt.

Yet another method which can be used to characterize an CD70 antibody is to use competition assays with other antibodies known to bind to the same antigen, i.e., various fragments on CD70, to determine if the CD70 antibody binds to the same epitope as other antibodies. Competition assays are well known to those of skill in the art.

An expression vector can be used to direct expression of an CD70 antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 263:621, 1988; Wu et al., J. Biol. Chem., 269:542, 1994; Zenke et al., Proc. Natl. Acad. Sci. USA, 87:3655, 1990; and Wu et al., J. Biol. Chem., 266:338, 1991. Therapeutic compositions containing a polynucleotide are administered in a range of about 100 ng to about 200 mg of DNA for local administration in a gene therapy protocol. Concentration ranges of about 500 ng to about 50 mg, about 1 to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1:51, 1994; Kimura, Human Gene Therapy, 5:845, 1994; Connelly, Human Gene Therapy, 1995, 1:185; and Kaplitt, Nature Genetics, 6:148, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Pat. No. 2,200,651; and EP Pat. No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 3:147, 1992); ligand-linked DNA (see, e.g., Wu, J. Biol. Chem., 264:16985, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 14:2411, 1994 and in Woffendin, Proc. Natl. Acad. Sci., 91:1581, 1994.

In some embodiments, the invention encompasses compositions, including pharmaceutical compositions, comprising antibodies described herein or made by the methods and having the characteristics described herein. As used herein, compositions comprise one or more antibodies that bind to CD70, or one or more polynucleotides comprising sequences encoding one or more these antibodies. These compositions may further comprise suitable excipients, such as pharmaceutically acceptable excipients including buffers, which are well known in the art.

The invention also provides methods of making any of these antibodies. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain or the light chain variable regions of antibody 31H1, 6362, 40E3, 42C3, 45F11, 64F9, 72C2, 2F10, 4F11, 10H10, 17G6, 65E11, P02B10, P07D03, P08A02, P08E02, P08F08, P08G02, P12B09, P12F02, P12G07, P13F04, P15D02 or P16C05. The sequence encoding the antibody of interest may be maintained in a vector in a host cell and the host cell can then be expanded and frozen for future use. Vectors (including expression vectors) and host cells are further described herein.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT Publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In the recombinant humanized antibodies, the Fcγ portion can be modified to avoid interaction with Fcγ receptor and the complement and immune systems. The techniques for preparation of such antibodies are described in WO 99/58572. For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to the antibodies and polypeptides of the invention including variants shown in Table 5, including functionally equivalent antibodies which do not significantly affect their properties and variants which have enhanced or decreased activity or affinity. For example, the amino acid sequence may be mutated to obtain an antibody with the desired binding affinity to CD70. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 5 under the heading of "conservative substitutions." If such substitutions result in a change in biological activity, then more substantial changes, denominated "exemplary substitutions" in Table 5, or as further described below in reference to amino acid classes, may be introduced and the products screened. In some embodiments, substitution variants of antibodies provided herein have no more than 15, 14, 13, 12, 11, 10, 9, 8, 7, 6, 5, 4, 3, 2, or 1 conservative substitution in the VH or VL region as compared to the reference parent antibody. In some embodiments, the substitutions are not within a CDR of the VH or VL region.

TABLE 5

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acid residues are divided into groups based on common side-chain properties:

(1) Non-polar: Norleucine, Met, Ala, Val, Leu, Ile;
(2) Polar without charge: Cys, Ser, Thr, Asn, Gin;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, Chem. Immunol. 65:111-128, 1997; Wright and Morrison, TibTECH 15:26-32, 1997). The oligosaccharide side chains of the immunoglobulins affect the protein's function (Boyd et al., Mol. Immunol. 32:1311-1318, 1996; Wittwe and Howard, Biochem. 29:4175-4180, 1990) and the intramolecular interaction between portions of the glycoprotein, which can affect the conformation and presented three-dimensional surface of the glycoprotein (Jefferis and Lund, supra; Wyss and Wagner, Current Opin. Biotech. 7:409-416, 1996). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., Mature Biotech. 17:176-180, 1999).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., J. Biol. Chem. 272:9062-9070, 1997).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation.

Modifications can be used, for example, for attachment of labels for immunoassay. Modified polypeptides are made using established procedures in the art and can be screened using standard assays known in the art, some of which are described below and in the Examples.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain is capable of specifically binding FcRn or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., Bio/Technology, 10:779-783, 1992; Barbas et al., Proc Nat. Acad. Sci, USA 91:3809-3813, 1994; Schier et al., Gene, 169:147-155, 1995; Yelton et al., J. Immunol., 155:1994-2004, 1995; Jackson et al., J. Immunol., 154(7):3310-9, 1995, Hawkins et al., J. Mol. Biol., 226:889-896, 1992; and PCT Publication No. WO2004/058184).

The following methods may be used for adjusting the affinity of an antibody and for characterizing a CDR. One way of characterizing a CDR of an antibody or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased, or no binding are identified. Methods for determining binding affinity are well-known in the art. Binding affinity may be determined using Biacore™ surface plasmon resonance analysis, which detects differences in binding affinity of about 2-fold or greater. Biacore™ is particularly useful when the starting antibody already binds with a relatively high affinity, for example a Ko of about 10 nM or lower. Screening using Biacore™ surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., Gene 137(1):109-18, 1993.

The CDR may be CDRH3 or CDRL3. The CDR may be one or more of CDRL1, CDRL2, CDRL3, CDRH1, CDRH2, or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved or altered binding affinity using any method known in the art, including screening using Biacore™ surface plasmon resonance analysis, and selection using any method known in the art for selection, including phage display, yeast display, and ribosome display.

The invention also encompasses fusion proteins comprising one or more fragments or regions from the antibodies of this invention. In one embodiment, a fusion polypeptide is provided that comprises at least 10 contiguous amino acids of the variable light chain region shown in SEQ ID NOs: 1, 3, 5, 7, 9, 11, 13, 15, 17, 19, 21, 23, 25, 27, 29, 31, 33, 35, 37, 39, 41, 43, 45 or 47, or at least 10 amino acids of the variable heavy chain region shown in SEQ ID NOs: 2, 4, 6, 8, 10, 12, 14, 16, 18, 20, 22, 24, 26, 28, 30, 32, 34, 36, 38, 40, 42, 44, 46 or 48. In other embodiments, a fusion polypeptide is provided that comprises at least about 10, at least about 15, at least about 20, at least about 25, or at least about 30 contiguous amino acids of the variable light chain region or at least about 10, at least about 15, at least about 20, at least about 25, or at least about 30 contiguous amino acids of the variable heavy chain region. In another embodiment, the fusion polypeptide comprises one or more CDR(s). In still other embodiments, the fusion polypeptide comprises CDR H3 (VH CDR3) or CDR L3 (VL CDR3). For purposes of this invention, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag (SEQ ID NO: 531). Tags are well known in the art.

A fusion polypeptide can be created by methods known in the art, for example, synthetically or recombinantly. Typically, the fusion proteins of this invention are made by preparing an expressing a polynucleotide encoding them using recombinant methods described herein, although they may also be prepared by other means known in the art, including, for example, chemical synthesis.

This invention also provides compositions comprising antibodies conjugated (for example, linked) to an agent that facilitate coupling to a solid support (such as biotin or avidin). For simplicity, reference will be made generally to antibodies with the understanding that these methods apply to any of the CD70 antibody embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The invention also provides isolated polynucleotides encoding the antibodies of the invention, and vectors and host cells comprising the polynucleotide.

Accordingly, the invention provides polynucleotides (or compositions, including pharmaceutical compositions), comprising polynucleotides encoding any of the following: 31H1, 6362, 40E3, 42C3, 45F11, 64F9, 72C2, 2F10, 4F11, 10H10, 17G6, 65E11, P02B10, P07D03, P08A02, P08E02, P08F08, P08G02, P12B09, P12F02, P12G07, P13F04, P15D02 or P16C05, or any fragment or part thereof having the ability to bind CD70.

In another aspect, the invention provides polynucleotides encoding any of the antibodies (including antibody fragments) and polypeptides described herein, such as antibodies and polypeptides having impaired effector function. Polynucleotides can be made and expressed by procedures known in the art.

In another aspect, the invention provides compositions (such as a pharmaceutical compositions) comprising any of the polynucleotides of the invention. In some embodiments, the composition comprises an expression vector comprising a polynucleotide encoding any of the antibodies described herein.

Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions or substitutions of nucleotides. The resulting mRNA and protein may, but need not, have an altered structure or function. Alleles may be identified using standard techniques (such as hybridization, amplification or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtilis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells. Screening the host cells for a specific binding to CD70 is effected by an immunoassay or FACS. A cell overexpressing the antibody or protein of interest can be identified.

Methods of Using the CD70 Antibodies

The antibodies of the present invention are useful in various applications including, but are not limited to, therapeutic treatment methods and diagnostic treatment methods.

The antibodies (e.g., monospecific and bispecific) obtained by the methods described above can be used as a medicament. In some embodiments, such a medicament can be used for treating cancer. In some embodiments, the cancer is a cancer of hematopoietic origin, such as a lymphoma or leukemia. In some embodiments, the cancer is Renal Cell Carcinoma, Glioblastoma, glioma such as low grade glioma, Non-Hodgkin's Lymphoma (NHL), Hodgkin's Disease (HD), Waldenstrom's macroglobulinemia, Acute Myeloid Leukemia, Multiple Myeloma, diffuse large-cell lymphoma, follicular lymphoma or Non-Small Cell Lung Cancer In some embodiments, provided is a method of inhibiting tumor growth or progression in a subject who has malignant cells expressing CD70, comprising administering to the subject in need thereof an effective amount of a composition comprising the CD70 antibodies (e.g., CD70-CD3 bispecific antibodies) as described herein. In other embodiments, provided is a method of inhibiting metastasis of cells expressing CD70 in a subject, comprising administering to the subject in need thereof an effective amount of a composition comprising the CD70 antibodies (e.g., CD70-CD3 bispecific antibodies) as described herein. In other embodiments, provided is a method of inducing tumor regression in malignant cells in a subject, comprising administering to the subject in need thereof an effective amount of a composition comprising the CD70 antibodies (e.g., CD70-CD3 bispecific antibodies) as described herein.

In some embodiments, the antibody (e.g., CD70-CD3 bispecific antibody) according to the invention can be used in the manufacture of a medicament for treatment of a cancer in a patient in need thereof.

In some embodiments, the treatment can be in combination with one or more therapies against cancer selected from the group of antibodies therapy, chemotherapy, cytokines therapy, targeted therapy, vaccine therapy, dendritic cell therapy, gene therapy, hormone therapy, surgical resection, laser light therapy and radiation therapy.

For example, in some embodiments, the CD70 antibodies (e.g., CD70-CD3 bispecific antibodies) of the present invention are administered to a patient in conjunction with (e.g., before, simultaneously or following) treatment with small molecule Tyrosine Kinase Inhibitors (TKIs) such as sunitinib and pazopanib that target Vascular Endothelial Growth Factor (VEGF) receptor, monoclonal antibody targeting VEGF such as bevacizumab, mammalian target of Rapamycin (mTOR) inhibitor temsirolimus, as well as high dose IL-2. In some embodiments, the CD70 antibodies (e.g., CD70-CD3 bispecific antibodies) of the present invention are administered to a patient in conjunction with one or more of the following: an anti-PD-1 antibody (e.g., nivolumab, pembrolizumab, or PF-06801591), an anti-PD-L1 antibody (e.g., avelumab, atezolizumab, or durvalumab) an anti-OX40 antibody (e.g., PF-04518600), an anti-4-1 BB antibody (e.g., PF-05082566), an anti-MCSF antibody (e.g., PD-0360324), an anti-GITR antibody, or an anti-TIGIT antibody.

The administration of the antibodies (e.g., monospecific or bispecific) according to the invention may be carried out in any convenient manner, including by aerosol inhalation, injection, ingestion, transfusion, implantation or transplantation. The compositions described herein may be administered to a patient subcutaneously, intradermally, intratumorally, intracranially, intranodally, intramedullary, intramuscularly, by intravenous or intralymphatic injection, or intraperitoneally. In one embodiment, the antibody compositions of the invention are preferably administered by intravenous injection.

In some embodiments, the administration of the antibodies (e.g., monospecific or bispecific) can comprise administration of, for example, about 0.01 to about 20 mg per kg body weight including all integer values of mg per kg within those ranges. In some embodiments, the administration of the antibodies can comprise administration of about 0.1 to 10 mg per kg body weight including all integer values of mg per kg within those ranges. The antibody can be administrated in one or more doses. In some embodiments, said effective amount of the antibody can be administrated as a single dose. In some embodiments, said effective amount of antibodies can be administrated as more than one dose over a period time. Timing of administration is within the judgment of managing physician and depends on the clinical condition of the patient. While individual needs vary, determination of optimal ranges of effective amounts of a given antibody (e.g., monospecific or bispecific) for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of heteromultimeric antibody or composition comprising those antibodies are administrated parenterally. In some embodiments, administration can be an intravenous administration. In some embodiments, administration can be directly done by injection within a tumor.

In some embodiments, anti-CD70 antibodies provided herein may be used for diagnostic purposes, such in assays to identify CD70 protein in samples (e.g. in immunohistochemistry assays) or in patients.

Compositions

In one aspect, the present invention provides a pharmaceutical composition comprising an antibody (e.g., monospecific or bispecific) of the invention or portion thereof as described above in a pharmaceutically acceptable carrier. In certain embodiments, the polypeptides of the invention may be present in a neutral form (including zwitter ionic forms) or as a positively or negatively-charged species. In some embodiments, the polypeptides may be complexed with a counterion to form a "pharmaceutically acceptable salt," which refers to a complex comprising one or more polypeptides and one or more counterions, where the counterions are derived from pharmaceutically acceptable inorganic and organic acids and bases.

The antibody (e.g., monospecific or bispecific) or portions thereof, may be administered alone or in combination with one or more other polypeptides of the invention or in combination with one or more other drugs (or as any combination thereof). The pharmaceutical compositions, methods and uses of the invention thus also encompass embodiments of combinations (co-administration) with other active agents, as detailed below.

As used herein, the terms "co-administration," "co-administered" and "in combination with," referring to the antibodies of the invention and one or more other therapeutic agents, is intended to mean, and does refer to and include the following: (i) simultaneous administration of such combination of an antibody disclosed herein and therapeutic agent(s) to a patient in need of treatment, when such components are formulated together into a single dosage form which releases said components at substantially the same time to said patient; (ii) substantially simultaneous administration of such combination of an antibody disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of an antibody disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of an antibody disclosed herein and therapeutic agent(s) to a patient in need of treatment, when such components are formulated together into a single dosage form which releases said components in a controlled manner whereupon they are concurrently, consecutively, or overlappingly released at the same or different times to said patient, where each part may be administered by either the same or a different route.

Generally, the antibody (e.g., monospecific or bispecific) disclosed herein or portions thereof are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the heterodimeric proteins and portions thereof disclosed herein.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Preferred embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate or modified release. Modified release formulations include controlled, delayed, sustained, pulsed, targeted and programmed release formulations. For example, in one aspect, sterile injectable solutions can be prepared by incorporating the heterodimeric protein, e.g., bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects or laboratory values. Thus, the present invention encompasses intrapatient dose-escalation as determined by the skilled artisan. Determining appropriate dosages and regimens are well-known in the relevant art and would be understood to be encompassed by the skilled artisan once provided the teachings disclosed herein.

Generally, for administration of the antibodies described herein (monospecific or bispecific), the candidate dosage can be administered daily, every week, every other week, every three weeks, every four weeks, every five weeks, every six weeks, every seven weeks, every eight weeks, every ten weeks, every twelve weeks, or more than every twelve weeks. For repeated administrations over several days or longer, depending on the condition, the treatment is sustained until a desired suppression of symptoms occurs or until sufficient therapeutic levels are achieved, for example, to reduce symptoms associated with cancer. The progress of this therapy is easily monitored by conventional techniques and assays. The dosing regimen (including the anti-FLT monospecific or bispecific antibody used) can vary over time.

In some embodiments, the candidate dosage is administered daily with the dosage ranging from about any of 1 µg/kg to 30 µg/kg to 300 µg/kg to 3 mg/kg, to 30 mg/kg, to 100 mg/kg or more, depending on the factors mentioned above. For example, daily dosage of about 0.01 mg/kg, about 0.03 mg/kg, about 0.1 mg/kg, about 0.3 mg/kg, about 1 mg/kg, about 2.5 mg/kg, about 3 mg/kg, about 5 mg/kg, about 10 mg/kg, about 15 mg/kg, and about 25 mg/kg may be used.

In some embodiments, the candidate dosage is administered every week with the dosage ranging from about any of 1 µg/kg to 30 µg/kg to 300 µg/kg to 3 mg/kg, to 30 mg/kg, to 100 mg/kg or more, depending on the factors mentioned above. For example, a weekly dosage of about 0.01 mg/kg, about 0.03 mg/kg, about 0.1 mg/kg, about 0.3 mg/kg, about 0.5 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every two weeks with the dosage ranging from about any of 1 µg/kg to 30 µg/kg to 300 µg/kg to 3 mg/kg, to 30 mg/kg, to 100 mg/kg or more, depending on the factors mentioned above. For example, a bi-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every three weeks with the dosage ranging from about any of 1 µg/kg to 30 µg/kg to 300 µg/kg to 3 mg/kg, to 30 mg/kg, to 100 mg/kg or more, depending on the factors mentioned above. For example, a tri-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In some embodiments, the candidate dosage is administered every month or every four weeks with the dosage ranging from about any of 1 µg/kg to 30 µg/kg to 300 µg/kg to 3 mg/kg, to 30 mg/kg, to 100 mg/kg or more, depending on the factors mentioned above. For example, a monthly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In other embodiments, the candidate dosage is administered daily with the dosage ranging from about 0.01 mg to about 1200 mg or more, depending on the factors mentioned above. For example, daily dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, or about 1200 mg may be used.

In other embodiments, the candidate dosage is administered every week with the dosage ranging from about 0.01 mg to about 2000 mg or more, depending on the factors mentioned above. For example, weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every two weeks with the dosage ranging from about 0.01 mg to about 2000 mg or more, depending on the factors mentioned above. For example, bi-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every three weeks with the dosage ranging from about 0.01 mg to about 2500 mg or more, depending on the factors mentioned above. For example, tri-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg may be used.

In other embodiments, the candidate dosage is administered every four weeks or month with the dosage ranging from about 0.01 mg to about 3000 mg or more, depending on the factors mentioned above. For example, monthly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, or about 3000 mg may be used.

Kits

The invention also provides kits for use in the instant methods. Kits of the invention include one or more containers comprising the antibody (e.g., monospecific or bispecific) as described herein and instructions for use in accordance with any of the methods of the invention described herein. Generally, these instructions comprise a description of administration of the antibody protein for the above described therapeutic treatments.

The instructions relating to the use of the antibody (e.g., monospecific or bispecific) as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a bispecific antibody. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1: Determination of Kinetics and Affinity of Human CD70/CD70 Antibodies Interactions at 37° C.

The kinetics and affinity of anti-CD70 antibodies disclosed herein can be measured on a Biacore T200 surface Plasmon resonance biosensor (GE Lifesciences, Piscataway N.J.).

Example 2: T-Cell Mediated Killing of RCC Cell Lines Using CD70-CD3 Bispecific IgG In Vitro Human anti-CD70 and human anti-CD3 (h2B4-VH-hnps VL-TK ("H2B4")) antibodies are expressed as human IgG2dA_D265A engineered with EEEE on one arm and RRRR on the other arm for bispecific exchange at positions 223, 225, and 228 (e.g., (C223E or C223R), (E225E or E225R), and (P228E or P228R)) in the hinge region and at position 409 or 368 (e.g., K409R or L368E (EU numbering scheme)) in the CH3 region of human IgG2 (SEQ ID NO: 279). The CD70/CD3 bispecific antibody also has the mutation from D to A at position 265 (EU numbering scheme).

CD3+ T cells from human PBMC are negatively selected using Pan T Cell Isolation kit, human (Miltenyi, San Diego Calif.). Target expressing (786-0) cells and CD3+ T-cells are seeded on clear U-bottom plates at 20000 and 100000 cells/well respectively. Cells are treated with 8-fold serially diluted bispecific antibody. RCC cell depletion is determined by flow-cytometry analysis 24 hours after treatment. Cell depletion is measured by contrast to control treated cells. EC50 is calculated by Prism software.

Example 3: CD70-CD3 Bispecific IgG Induces Tumor Ablation in RCC Subcutaneous Xenograft Model NOD scid gamma (NSG) mice are implanted with 786-0 tumors subcutaneously and once the tumors attained a volume of 200 mm$^3$, the mice are dosed with 20 million expanded T cells each intraperitoneally. Two days later the anti CD70 bispecific antibodies are dosed at 300, 100, or 30 ug/mL intravenously via tail vein injection to determine the optimal bispecific antibody dose.

Materials and Methods:

NOD scid gamma (NSG) mice are shaved and prepared for subcutaneous tumor implant on the right flank. 786-0 tumor cells that are known to express CD70 are expanded in RPMI supplemented with 10% FBS. On Day 0, 786-0 cells are resuspended in serum-free RPMI at the required concentration to inject 5 million cells per animal. Tumor cells are injected in 100 uL of serum-free RPMI combined with 100 uL Matrigel (Corning) per animal subcutaneously. Day 0 baseline body weights are recorded for all animals immediately after tumor implant. Tumors are measured twice a week starting on Day 9 using Digimatic Calipers (Mitutoyo) and body weights recorded. On Day 14, when the tumors attained 200 mm$^3$ (standard error 8.39) 40 tumor-bearing mice are randomized to 4 groups of 10 mice each. T cells are thawed and expanded and then resuspended in serum-free RPMI at the required concentration to inject 20 million T cells per animal. T cells are injected in 200 uL of serum-free RPMI per animal intraperitoneally. Two days later bispecifics are dosed intravenously via tail vein at 300, 100, or 30 ug/mL per animal. Tumors are measured and body weights recorded twice a week till the untreated group reached the study end-point (1500 mm$^3$ tumor volume).

Tumor volumes (mean and error SEM) are plotted on GraphPad Prism and statistics are calculated using one-way ANOVA with repeated measures.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

It is claimed:

1. An isolated antibody, which specifically binds to Cluster of Differentiation 70 (CD70), wherein the antibody comprises a heavy chain variable (VH) region comprising a VH complementarity determining region one (CDR1), a VH CDR2, and a VH CDR3, and a light chain variable (VL) region comprising a VL CDR1, a VL CDR2, and a VL CDR3, wherein:
   the VH CDR1 comprises the amino acid sequence of SEQ ID NO: 97,
   the VH CDR2 comprises the amino acid sequence of SEQ ID NO: 100,
   the VH CDR3 comprises the amino acid sequence of SEQ ID NO: 102; or
   the VH CDR1 comprises the amino acid sequence of SEQ ID NO: 98,
   the VH CDR2 comprises the amino acid sequence of SEQ ID NO: 101,
   the VH CDR3 comprises the amino acid sequence of SEQ ID NO: 102; or
   the VH CDR1 comprises the amino acid sequence of SEQ ID NO: 99,
   the VH CDR2 comprises the amino acid sequence of SEQ ID NO: 100,
   the VH CDR3 comprises the amino acid sequence of SEQ ID NO: 102; and
   wherein
   the VL CDR1 comprises the amino acid sequence of SEQ ID NO: 217,
   the VL CDR2 comprises the amino acid sequence of SEQ ID NO: 218, and
   the VL CDR3 comprises the amino acid sequence of SEQ ID NO: 219.

2. The antibody of claim 1, wherein the VH region comprises the amino acid sequence of SEQ ID NO: 18 and the VL region comprises the amino acid sequence of SEQ ID NO: 17.

3. A bispecific antibody wherein the bispecific antibody is a full-length antibody, comprising a first antigen binding site of the bispecific antibody specifically binding to a target antigen, and comprising a second antigen binding site of the bispecific antibody capable of recruiting the activity of a human immune effector cell by specifically binding to an effector antigen located on the human immune effector cell, wherein the first antigen binding site comprises a heavy chain variable (VH) region comprising a VH CDR1, VH CDR2, and VH CDR3 and a light chain variable (VL) region comprising a VL CDR1, VL CDR2, and VL CDR3, wherein the VH region comprises the amino acid sequence of SEQ ID NO: 18 and the VL region comprises the amino acid sequence of SEQ ID NO: 17.

4. A bispecific antibody wherein the bispecific antibody is a full-length antibody, comprising a first antigen binding site of the bispecific antibody specifically binding to CD70, and comprising a second antigen binding site of the bispecific antibody capable of recruiting the activity of a human immune effector cell by specifically binding to an effector antigen located on the human immune effector cell, wherein the first antigen binding site comprises a heavy chain variable (VH) region comprising a VH complementarity determining region one (CDR1), a VH CDR2, and a VH CDR3, and a light chain variable (VL) region comprising a VL CDR1, a VL CDR2, and a VL CDR3 wherein:
   the VH CDR1 comprises the amino acid sequence of SEQ ID NO: 97,
   the VH CDR2 comprises the amino acid sequence of SEQ ID NO: 100,
   the VH CDR3 comprises the amino acid sequence of SEQ ID NO: 102; or
   the VH CDR1 comprises the amino acid sequence of SEQ ID NO: 98,
   the VH CDR2 comprises the amino acid sequence of SEQ ID NO: 101,
   the VH CDR3 comprises the amino acid sequence of SEQ ID NO: 102; or
   the VH CDR1 comprises the amino acid sequence of SEQ ID NO: 99,
   the VH CDR2 comprises the amino acid sequence of SEQ ID NO: 100,
   the VH CDR3 comprises the amino acid sequence of SEQ ID NO: 102; and
   wherein
   the VL CDR1 comprises the amino acid sequence of SEQ ID NO: 217,
   the VL CDR2 comprises the amino acid sequence of SEQ ID NO: 218, and
   the VL CDR3 comprises the amino acid sequence of SEQ ID NO: 219.

5. The bispecific antibody of claim 4, wherein the second antigen binding site specifically binds to the effector antigen CD3.

6. The bispecific antibody of claim 5, wherein the second antigen binding site comprises a) a heavy chain variable (VH) region comprising (i) a VH complementary determining region one (CDR1) comprising the sequence shown in SEQ ID NO: 267, 268, or 269; (ii) a VH CDR2 comprising the sequence shown in SEQ ID NO: 270 or 271; and (iii) a VH CDR3 comprising the sequence shown in SEQ ID NO: 272; and b) a light chain variable (VL) region comprising (i) a VL CDR1 comprising the sequence shown in SEQ ID NO: 273; (ii) a VL CDR2 comprising the sequence shown in SEQ ID NO: 274; and (iii) a VL CDR3 comprising the sequence shown in SEQ ID NO: 275.

7. The bispecific antibody of claim 3, wherein both the first and the second antigen binding sites of the bispecific antibody comprise amino acid modifications at positions 223, 225, and 228 in the hinge region and at position 409 or 368, according to the EU numbering scheme, in the CH3 region of a human IgG2 comprising SEQ ID NO: 279.

8. The bispecific antibody of claim 7, further comprising an amino acid modification at one or more of positions 265, 330 and 331 of the human IgG2.

9. A nucleic acid encoding the antibody of claim 1.

10. A vector comprising the nucleic acid of claim 9.

11. A host cell comprising the nucleic acid of claim 9.

12. A method of treating a subject in need thereof comprising:
a) providing the antibody of claim 1; and
b) administering said antibody to said subject.

13. A pharmaceutical composition comprising the antibody of claim 1.

14. A method of treating a condition associated with malignant cells expressing CD70 in a subject comprising administering to a subject in need thereof an effective amount of the antibody of claim 1.

15. The method of claim 14, wherein the condition is a cancer.

16. The method of claim 15, wherein the cancer is an CD70 related cancer selected from the group consisting of Renal Cell Carcinoma, Glioblastoma, glioma such as low grade glioma, Non-Hodgkin's Lymphoma (NHL), Hodgkin's Disease (HD), Waldenstrom's macroglobulinemia, Acute Myeloid Leukemia, Multiple Myeloma, diffuse large-cell lymphoma, follicular lymphoma or Non-Small Cell Lung Cancer.

17. A method of inhibiting tumor growth or progression in a subject who has malignant cells expressing CD70, comprising administering to the subject in need thereof an effective amount of the pharmaceutical composition of claim 13 to the subject.

18. A method of inhibiting metastasis of malignant cells expressing CD70 in a subject, comprising administering to the subject in need thereof an effective amount of the pharmaceutical composition of claim 13 to the subject.

19. A method of inducing tumor regression in a subject who has malignant cells expressing CD70, comprising administering to the subject in need thereof an effective amount of the pharmaceutical composition of claim 13 to the subject.

20. A method of producing an antibody, comprising culturing the host cell of claim 11 under conditions that result in production of the antibody, and isolating the antibody from the host cell or culture.

21. The antibody of claim 1, wherein:
the VH CDR1 comprises the amino acid sequence of SEQ ID NO: 97,
the VH CDR2 comprises the amino acid sequence of SEQ ID NO: 100, and
the VH CDR3 comprises the amino acid sequence of SEQ ID NO: 102.

22. An isolated antibody, which specifically binds to Cluster of Differentiation 70 (CD70), wherein the antibody comprises a heavy chain variable (VH) region comprising a VH complementarity determining region one (CDR1), a VH CDR2, and a VH CDR3, and a light chain variable (VL) region comprising a VL CDR1, a VL CDR2, and a VL CDR3, wherein the VL region comprises the amino acid sequence of SEQ ID NO: 17 and the VH region comprises the amino acid sequence of SEQ ID NO: 18.

23. The bispecific antibody of claim 4, wherein:
the VH CDR1 comprises the amino acid sequence of SEQ ID NO: 97,
the VH CDR2 comprises the amino acid sequence of SEQ ID NO: 100, and
the VH CDR3 comprises the amino acid sequence of SEQ ID NO: 102.

24. A pharmaceutical composition comprising the antibody of claim 2.

25. A pharmaceutical composition comprising the antibody of claim 3.

26. A pharmaceutical composition comprising the antibody of claim 4.

27. A pharmaceutical composition comprising the antibody of claim 5.

28. A pharmaceutical composition comprising the antibody of claim 6.

29. A pharmaceutical composition comprising the antibody of claim 7.

30. A pharmaceutical composition comprising the antibody of claim 8.

31. A pharmaceutical composition comprising the antibody of claim 21.

32. A pharmaceutical composition comprising the antibody of claim 22.

33. A pharmaceutical composition comprising the antibody of claim 23.

34. A host cell comprising the vector of claim 10.

35. A method of making the host cell of claim 11, comprising introducing the nucleic acid of claim 9 into a host cell.

36. A method of making the host cell of claim 34, comprising introducing the vector of claim 11 into a host cell.

* * * * *

UNITED STATES PATENT AND TRADEMARK OFFICE
CERTIFICATE OF CORRECTION

PATENT NO. : 11,377,500 B2  
APPLICATION NO. : 16/264485  
DATED : July 5, 2022  
INVENTOR(S) : Siler Panowski et al.

Page 1 of 1

It is certified that error appears in the above-identified patent and that said Letters Patent is hereby corrected as shown below:

In the Claims

In Claim 36, Line 55, delete "claim 11" and insert -- claim 10 --.

Signed and Sealed this  
Seventh Day of January, 2025

Derrick Brent  
*Acting Director of the United States Patent and Trademark Office*

```
                        SEQUENCE LISTING

<160> NUMBER OF SEQ ID NOS: 531

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Val Met Thr Gln Asn Pro Leu Ser Ser Pro Val Thr Leu Gly
1               5                   10                  15
```

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Leu Thr Ile Gly Gly Gly Ser Lys Val Glu Ile Lys
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Phe Ser Trp Val Arg Gln Ala Pro Gly Gln Gly Leu Glu Trp Met
        35                  40                  45

Gly Gly Ile Ile Pro Ile Phe Gly Ser Ala Asn Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ile Ser Leu Arg Ser Glu Asp Thr Ala Val Tyr Tyr Cys
                85                  90                  95

Ala Arg Gly Gly Ser Ser Ser Pro Phe Ala Tyr Trp Gly Gln Gly Thr
            100                 105                 110

Leu Val Thr Val Ser Ser
        115

<210> SEQ ID NO 3
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Ser
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
            85                  90                  95

Thr Gln Phe Pro Leu Thr Ile Gly Gly Gly Ser Lys Val Glu Ile Lys
            100                 105                 110

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Gly Phe Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Val Phe
65                  70                  75                  80

Met Glu Leu Ile Ser Leu Arg Ser Glu Tyr Thr Ala Val Tyr Tyr Cys
                85                  90                  95

Ala Arg Gly Gly Ser Ser Pro Phe Ala Tyr Trp Gly Gln Gly Thr
            100                 105                 110

Leu Val Thr Val Ser Ser
        115

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
            35                  40                  45

Tyr Ala Ala Ser Ser Leu Gln Ser Gly Val Pro Ser Lys Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 6
<211> LENGTH: 112
<212> TYPE: PRT
<213> ORGANISM: Artificial Sequence
<220> FEATURE:

-continued

<223> OTHER INFORMATION: Description of Artificial Sequence: Synthetic
     polypeptide

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Asn Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Asp Ile Arg Thr Trp Gly Gln Gly Thr Leu Val Thr Val Ser Ser
            100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 7

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Glu Asn Thr Tyr Leu Asn Trp Phe Gln Gln Arg Pro Gly Gln Ser
        35                  40                  45

Leu Arg Arg Leu Ile Tyr Gln Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Met Gln Gly
                85                  90                  95

Thr Tyr Trp Pro Pro Thr Phe Gly Gly Gly Thr Lys Val Glu Ile Lys
            100                 105                 110

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Ser
            20                  25                  30

Trp Met Ser Trp Val Arg Gln Ala Pro Gly Lys Gly Leu Glu Trp Val
        35                  40                  45

Ala Asn Ile Lys Arg Asp Gly Ser Glu Lys Tyr Tyr Val Asp Ser Val 50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Thr Gly Ser Phe Asp Tyr Trp Gly Gln Gly Thr Leu
                100                 105                 110

Val Thr Val Ser Ser
            115

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ile Val Met Thr Gln Ser Pro Ala Thr Leu Ser Met Ser Leu Gly
 1               5                  10                  15

Glu Arg Ala Thr Leu Ser Cys Arg Ala Ser Gln Ser Val Ser Ser Ser
                20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Thr Gly Ile Pro Ala Arg Phe Gly Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ile Asn Trp Pro His
                 85                  90                  95

Phe Gly Gly Gly Thr Lys Val Glu Ile Lys
            100                 105

<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Arg Gly Ser Gly Pro Gly Leu Val Lys Pro Ser Glu
 1               5                  10                  15

Thr Leu Ser Leu Thr Cys Thr Val Ser Asp Asp Ser Ile Ser Val Tyr
                20                  25                  30

Tyr Trp Ser Trp Ile Arg Gln Pro Ala Gly Lys Gly Leu Glu Trp Ile
             35                  40                  45

Gly Arg Val Tyr Ser Ser Gly Asn Ile Asn Tyr Asn Pro Ser Leu Glu
             50                  55                  60

Ser Arg Val Thr Met Ser Val Asp Thr Ser Lys Ser Arg Phe Ser Leu
 65                  70                  75                  80

Asn Leu Ser Ser Val Thr Ala Ala Asp Thr Ala Val Tyr Tyr Cys Ala
                 85                  90                  95

Arg Gly Leu Asp Ala Phe Asp Ile Trp Gly Gln Gly Thr Met Val Thr
            100                 105                 110

Val Ser Ser

```
                                 115

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Ile Leu Ile
        35                  40                  45

Tyr Gly Ala Ser Asn Leu Glu Thr Gly Val Pro Ser Arg Phe Ser Gly
    50                  55                  60

Ser Gly Ser Gly Thr Asp Phe Thr Phe Ala Ile Ser Ser Leu Gln Pro
65                  70                  75                  80

Glu Asp Val Ala Thr Tyr Tyr Cys Gln Gln Tyr Asp Asn Phe Pro Ile
                85                  90                  95

Thr Phe Gly Gln Gly Thr Arg Leu Glu Ile Lys
            100                 105

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Leu Glu Ser Gly Gly Gly Leu Val Gln Pro Gly Glu
1               5                   10                  15

Ser Leu Arg Leu Ser Cys Glu Val Ser Gly Phe Thr Phe Thr Ser Tyr
            20                  25                  30

Ala Met Ser Trp Val Arg Gln Val Pro Gly Lys Gly Leu Glu Trp Val
        35                  40                  45

Ser Ile Ile Ser Gly Val Ala Phe Thr Thr Tyr Tyr Ala Asp Ser Val
    50                  55                  60

Lys Gly Arg Phe Thr Ile Ser Arg Asp His Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Val Lys Val Asp Gly Glu Val Tyr Trp Gly Gln Gly Thr Leu Val Thr
            100                 105                 110

Val Ser Ser
        115

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

Glu Ile Val Met Thr Gln Ser Pro Asp Thr Leu Ser Val Ser Pro Gly
1               5                   10                  15

Glu Arg Ala Ile Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Ser Ala Ser Thr Arg Ala Ser Gly Ile Pro Ala Arg Phe Ser Gly
50                  55                  60

Ser Gly Ser Gly Thr Glu Phe Thr Leu Ser Ile Ser Ser Leu Gln Ser
65                  70                  75                  80

Glu Asp Phe Ala Val Tyr Tyr Cys Gln Gln Tyr Asp Asn Trp Pro Pro
                85                  90                  95

Leu Thr Phe Gly Gly Gly Thr Lys Val Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
1               5                   10                  15

Ser Val Lys Val Ser Cys Glu Ala Ser Gly Gly Thr Phe Ile Thr Tyr
                20                  25                  30

Ala Ile Ser Trp Val Arg Gln Ala Pro Gly Gln Gly Leu Glu Trp Met
            35                  40                  45

Gly Gly Ile Ile Pro Phe Phe Gly Thr Ala Asn Tyr Ala Gln Lys Phe
50                  55                  60

Gln Gly Arg Val Thr Ile Thr Ala Asp Lys Ser Thr Ser Thr Ala Ser
65                  70                  75                  80

Met Glu Leu Arg Ser Leu Arg Ser Glu Asp Thr Ala Met Tyr Tyr Cys
                85                  90                  95

Ala Gln Trp Glu Leu Phe Phe Phe Asp Phe Trp Gly Gln Gly Thr Pro
            100                 105                 110

Val Thr Val Ser Ser
        115

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Gln Pro Gly Gln Ala Pro Arg Leu Leu
            35                  40                  45

Ile Tyr Gly Ala Ser Ser Arg Ala Thr Gly Ile Pro Asp Arg Phe Ser
50                  55                  60

```
Gly Ser Gly Ser Gly Thr Asp Phe Thr Leu Thr Ile Ser Arg Leu Glu
 65                  70                  75                  80

Pro Glu Asp Phe Ala Ile Tyr Tyr Cys Gln Gln Tyr Gly Ser Ser Pro
                 85                  90                  95

Leu Thr Phe Gly Gly Gly Thr Lys Val Glu Ile Lys
            100                 105
```

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Ala Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Tyr Tyr
             20                  25                  30

Ser Met Asn Trp Val Arg Gln Ala Pro Gly Lys Gly Leu Glu Trp Val
         35                  40                  45

Ser His Ile Ser Ile Arg Ser Ser Thr Ile Tyr Phe Ala Asp Ser Ala
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Gly Ser Gly Trp Tyr Gly Asp Tyr Phe Asp Tyr Trp Gly Gln
            100                 105                 110

Gly Thr Leu Val Thr Val Ser Ser
            115                 120
```

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Asp Ile Gln Met Thr Gln Ser Pro Ser Ala Met Ser Ala Ser Val Gly
  1               5                  10                  15

Asp Arg Val Thr Ile Thr Cys Arg Ala Ser Gln Asp Ile Ser Asn Tyr
             20                  25                  30

Leu Ala Trp Phe Gln Gln Lys Pro Gly Lys Val Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Leu Pro
 65                  70                  75                  80

Glu Asp Phe Ala Thr Tyr Tyr Cys Leu Gln Leu Asn Ser Phe Pro Phe
                 85                  90                  95

Thr Phe Gly Gly Gly Thr Lys Val Glu Ile Asn
            100                 105
```

<210> SEQ ID NO 18

<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Thr Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Thr Gln Val
65                  70                  75                  80

Val Leu Thr Met Thr Asn Met Asp Pro Val Asp Thr Ala Thr Tyr Tyr
                85                  90                  95

Cys Ala Arg Ile Arg Asp Tyr Tyr Asp Ile Ser Ser Tyr Tyr Asp Tyr
            100                 105                 110

Trp Gly Gln Gly Thr Leu Val Ser Val Ser Ser
        115                 120
```

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Ser Phe Pro Phe
                85                  90                  95

Thr Phe Gly Pro Gly Thr Lys Val Asp Ile Lys
            100                 105
```

<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Glu Val Gln Leu Val Glu Ser Gly Gly Gly Leu Val Gln Pro Gly Gly
1               5                   10                  15
```

Ser Leu Arg Leu Ser Cys Ala Val Ser Gly Phe Thr Phe Ser Asn His
            20                  25                  30

Asn Ile His Trp Val Arg Gln Ala Pro Gly Lys Gly Leu Glu Trp Ile
        35                  40                  45

Ser Tyr Ile Ser Arg Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp His Ala Gln Trp Tyr Gly Met Asp Val Trp Gly Gln Gly
                100                 105                 110

Thr Thr Val Thr Val Ser Ser
            115

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Tyr Asn Asn Lys Asn Tyr Val Ala Trp Tyr Gln Gln Lys Pro Gly Gln
        35                  40                  45

Pro Pro Asn Leu Leu Ile Phe Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Leu Thr Phe Gly Gly Gly Thr Lys Val Glu Ile Lys
                100                 105                 110

<210> SEQ ID NO 22
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Val Tyr
65                  70                  75                  80

```
Leu Gln Met Asn Ser Leu Arg Ala Glu Asp Thr Gly Val Tyr Tyr Cys
                85                  90                  95

Ala Arg Glu Gly Val Asn Trp Gly Trp Arg Leu Tyr Trp His Phe Asp
            100                 105                 110

Leu Trp Gly Arg Gly Thr Leu Val Thr Val Ser Ser
        115                 120

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser His Ser Ser Ile Ser Arg Gly Asn Ile Tyr Phe Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Ser Gly Trp Tyr Gly Asp Tyr Phe Asp Tyr Trp Gly Gln
            100                 105                 110

Gly Thr Leu Val Thr Val Ser Ser
        115                 120

<210> SEQ ID NO 25
<211> LENGTH: 112
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Leu Gln Ser Val Leu Thr Gln Pro Pro Ser Ala Ser Gly Thr Pro
1               5                   10                  15

Gly Gln Arg Val Thr Ile Ser Cys Ser Gly Ser Ser Asn Ile Gly
            20                  25                  30

Ser Asn Tyr Val Tyr Trp Tyr Gln Gln Leu Pro Gly Thr Ala Pro Lys
        35                  40                  45

Leu Leu Ile Tyr Arg Asn Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Ala Trp Asp Asp
                85                  90                  95

Ser Leu Ser Gly Val Val Phe Gly Gly Gly Thr Lys Leu Thr Val Leu
            100                 105                 110

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Asn Tyr
            20                  25                  30

Ala Met Ser Trp Val Arg Gln Ala Pro Gly Lys Gly Leu Glu Trp Val
        35                  40                  45

Ser Ala Ile Arg Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Ile Ser Gly Thr Trp Tyr Pro Asp Tyr Trp Gly Gln
            100                 105                 110

Gly Thr Leu Val Thr Val Ser Ser
        115                 120

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Leu Gln Ser Val Leu Thr Gln Pro Pro Ser Ala Ser Gly Thr Pro
1               5                   10                  15

Gly Gln Arg Val Thr Ile Ser Cys Ser Gly Ser Arg Ser Asn Ile Gly

```
                    20                  25                  30
Ser Asn Tyr Val Tyr Trp Tyr Gln Gln Leu Pro Gly Thr Ala Pro Lys
            35                  40                  45

Leu Leu Ile Tyr Arg Asn Asn Gln Arg Pro Ser Gly Val Pro Asp Arg
        50                  55                  60

Phe Ser Gly Ser Lys Ser Gly Thr Ser Ala Ser Leu Ala Ile Ser Gly
 65                  70                  75                  80

Leu Arg Ser Glu Asp Glu Ala Asp Tyr Tyr Cys Ala Ser Trp Asp Gly
                85                  90                  95

Ser Leu Ser Ala Val Val Phe Gly Thr Gly Thr Lys Leu Thr Val Leu
            100                 105                 110

<210> SEQ ID NO 28
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ser Ile Tyr Pro Asp Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Ser Ser Thr Val Asp Tyr Pro Gly Tyr Ser Tyr Phe Asp Tyr Trp
            100                 105                 110

Gly Gln Gly Thr Leu Val Thr Val Ser Ser
        115                 120

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Leu Gln Ser Val Leu Thr Gln Pro Pro Ser Ala Ser Gly Thr Pro
 1               5                  10                  15

Gly Gln Arg Val Thr Ile Ser Cys Ser Gly Ser Ser Ser Asn Ile Gly
            20                  25                  30

Ser Asn Tyr Val Tyr Trp Tyr Gln Gln Leu Pro Gly Thr Ala Pro Lys
            35                  40                  45

Leu Leu Ile Tyr Arg Asn Asn Gln Arg Pro Ser Gly Val Pro Asp Arg
        50                  55                  60

Phe Ser Gly Ser Lys Ser Gly Thr Ser Ala Ser Leu Ala Ile Ser Gly
 65                  70                  75                  80

Leu Arg Ser Glu Asp Glu Ala Asp Tyr Tyr Cys Ala Thr Trp Asp Asp
```

```
                    85                  90                  95
Ser Leu Gly Ser Pro Val Phe Gly Thr Gly Thr Lys Leu Thr Val Leu
                100                 105                 110

<210> SEQ ID NO 30
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Pro Asp Gly Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ile Thr Ser Trp Tyr Tyr Gly Glu Pro Ala Phe Asp Ile
                100                 105                 110

Trp Gly Gln Gly Thr Leu Val Thr Val Ser Ser
            115                 120

<210> SEQ ID NO 31
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
                20                  25                  30

Arg Tyr Leu Asn Trp Tyr Gln Gln Lys Pro Gly Lys Ala Pro Lys Leu
            35                  40                  45

Leu Ile Tyr Ala Ala Ser Ile Leu Gln Thr Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Thr Met Trp Thr Phe Gly Gln Gly Thr Lys Val Glu Ile Lys
                100                 105                 110

<210> SEQ ID NO 32
<211> LENGTH: 122
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Gly Leu Ser Gln Ala Met Thr Gly Phe Gly Phe Asp Tyr Trp
            100                 105                 110

Gly Gln Gly Thr Leu Val Thr Val Ser Ser
            115                 120

<210> SEQ ID NO 33
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Leu Gln Ser Val Leu Thr Gln Pro Pro Ser Ala Ser Gly Thr Pro
1               5                   10                  15

Gly Gln Arg Val Thr Ile Ser Cys Ser Gly Ser Ser Ser Asn Ile Gly
            20                  25                  30

Ser Asn Tyr Val Asn Trp Tyr Gln Gln Leu Pro Gly Thr Ala Pro Lys
        35                  40                  45

Leu Leu Ile Tyr Gly Asp Tyr Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Thr Arg Asp Asp
                85                  90                  95

Ser Leu Ser Gly Ser Val Val Phe Gly Thr Gly Thr Lys Leu Thr Val
            100                 105                 110

Leu

<210> SEQ ID NO 34
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Gly Phe Thr Ser Tyr
            20                  25                  30

Trp Ile Gly Trp Val Arg Gln Met Pro Gly Lys Gly Leu Glu Trp Met
            35                  40                  45

Gly Ile Ile His Pro Asp Asp Ser Asp Thr Lys Tyr Ser Pro Ser Phe
 50                      55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Ser Ser Tyr Leu Arg Gly Leu Trp Gly Tyr Phe Asp Tyr Trp
            100                 105                 110

Gly Gln Gly Thr Leu Val Thr Val Ser Ser
        115                 120

<210> SEQ ID NO 35
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Leu Asp Ile Gln Met Thr Gln Ser Pro Ser Ser Leu Ser Ala Ser
 1               5                  10                  15

Val Gly Asp Arg Val Thr Ile Thr Cys Arg Ala Ser Gln Ser Ile Tyr
            20                  25                  30

Asp Tyr Leu His Trp Tyr Gln Gln Lys Pro Gly Lys Ala Pro Lys Leu
            35                  40                  45

Leu Ile Tyr Asp Ala Ser Asn Leu Gln Ser Gly Val Pro Ser Arg Phe
 50                      55                  60

Ser Gly Ser Gly Ser Gly Thr Asp Phe Thr Leu Thr Ile Ser Ser Leu
 65                  70                  75                  80

Gln Pro Glu Asp Phe Ala Thr Tyr Tyr Cys Gln Gln Ser Tyr Thr Thr
                 85                  90                  95

Pro Leu Phe Thr Phe Gly Gln Gly Thr Lys Val Glu Ile Lys
            100                 105                 110

<210> SEQ ID NO 36
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Thr Phe Pro Ser Ser
            20                  25                  30

Trp Ile Gly Trp Val Arg Gln Met Pro Gly Lys Gly Leu Glu Trp Met
            35                  40                  45

Gly Ile Ile Tyr Pro Asp Thr Ser His Thr Arg Tyr Ser Pro Ser Phe
 50                      55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Ala Ser Tyr Phe Asp Arg Gly Thr Gly Tyr Ser Ser Trp Trp
            100                 105                 110

Met Asp Val Trp Gly Gln Gly Thr Leu Val Thr Val Ser Ser
            115                 120                 125

<210> SEQ ID NO 37
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Tyr Ile Gly
            20                  25                  30

Arg Tyr Leu Asn Trp Tyr Gln Gln Lys Arg Gly Lys Ala Pro Lys Leu
        35                  40                  45

Leu Ile His Gly Ala Thr Ser Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Thr Ser Pro Thr Phe Gly Gln Gly Thr Lys Val Glu Ile Lys
            100                 105                 110

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Ser Met Ser Trp Val Arg Gln Ala Pro Gly Lys Gly Leu Glu Trp Val
        35                  40                  45

Ser Ala Ile Ser Gly Gly Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Asp Ile Ser Asp Ser Gly Gly Ser His Trp Tyr Phe Asp Tyr
            100                 105                 110

Trp Gly Gln Gly Thr Leu Val Thr Val Ser Ser
        115                 120

<210> SEQ ID NO 39
<211> LENGTH: 112
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 39

Glu Leu Gln Ser Val Leu Thr Gln Pro Pro Ser Ala Ser Gly Thr Pro
1               5                   10                  15

Gly Gln Arg Val Thr Ile Ser Cys Ser Gly Ser Thr Ser Asn Ile Gly
            20                  25                  30

Arg Asn Tyr Val Tyr Trp Tyr Gln Gln Leu Pro Gly Thr Ala Pro Lys
        35                  40                  45

Leu Leu Ile Tyr Arg Thr Asn Gln Arg Pro Ser Gly Val Pro Asp Arg
    50                  55                  60

Phe Ser Gly Ser Lys Ser Gly Thr Ser Ala Ser Leu Ala Ile Ser Gly
65                  70                  75                  80

Leu Arg Ser Glu Asp Glu Ala Asp Tyr Tyr Cys Ala Ala Trp Asp Asp
                85                  90                  95

Ser Leu Ser Gly Arg Val Phe Gly Thr Gly Thr Lys Leu Thr Val Leu
            100                 105                 110

<210> SEQ ID NO 40
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Gly Thr Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Ala Gly Ile Asp Pro Thr Ala Ser Asp Val Trp Gly
            100                 105                 110

Gln Gly Thr Leu Val Thr Val Ser Ser
        115                 120

<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Leu Gln Ser Val Leu Thr Gln Pro Pro Ser Ala Ser Gly Thr Pro
1               5                   10                  15

Gly Gln Arg Val Thr Ile Ser Cys Ser Gly Ser Ser Ser Asn Ile Gly
            20                  25                  30

Ser Asn Tyr Val Tyr Trp Tyr Gln Gln Leu Pro Gly Thr Ala Pro Lys

```
                35                  40                  45
Pro Leu Ile Tyr Met Asn Asn Gln Arg Pro Ser Gly Val Pro Asp Arg
         50                  55                  60

Phe Ser Gly Ser Lys Ser Gly Thr Ser Ala Ser Leu Ala Ile Ser Gly
 65                  70                  75                  80

Leu Arg Ser Glu Asp Glu Ala Asp Tyr Tyr Cys Ala Ala Trp Asp Asp
                 85                  90                  95

Ser Leu Ser Ala Val Val Phe Gly Thr Gly Thr Lys Leu Thr Val Leu
            100                 105                 110

<210> SEQ ID NO 42
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Phe
             20                  25                  30

Ala Met Ser Trp Val Arg Gln Ala Pro Gly Lys Gly Leu Glu Trp Val
         35                  40                  45

Ser Gly Ile Ser Gly Ser Gly Asp Asn Thr Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Asp Ile Gly Leu Gly Trp Tyr Ser Tyr Tyr Leu Asp
            100                 105                 110

Val Trp Gly Gln Gly Thr Leu Val Thr Val Ser Ser
         115                 120

<210> SEQ ID NO 43
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Leu Gln Ser Val Leu Thr Gln Pro Pro Ser Ala Ser Gly Thr Pro
 1               5                  10                  15

Gly Gln Arg Val Thr Ile Ser Cys Ser Gly Ser Asn Ser Asn Ile Gly
             20                  25                  30

Thr Asn Tyr Val Ser Trp Tyr Gln Gln Leu Pro Gly Thr Ala Pro Lys
         35                  40                  45

Leu Leu Ile Tyr Arg Ser Ser Arg Arg Pro Ser Gly Val Pro Asp Arg
         50                  55                  60

Phe Ser Gly Ser Lys Ser Gly Thr Ser Ala Ser Leu Ala Ile Ser Gly
 65                  70                  75                  80

Leu Arg Ser Glu Asp Glu Ala Asp Tyr Tyr Cys Ala Ala Trp Asp Gly
                 85                  90                  95

Ser Leu Ser Gly His Trp Val Phe Gly Thr Gly Thr Lys Leu Thr Val
```

<210> SEQ ID NO 44
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Glu Ile Ile Pro Ile Phe Gly Thr Ala Ser Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Trp Asp Asp Ser Trp Phe Asp Tyr Trp Gly Gln Gly
            100                 105                 110

Thr Leu Val Thr Val Ser Ser
        115

<210> SEQ ID NO 45
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Asp
                20                  25                  30

Thr Tyr Leu Asn Trp Tyr Gln Gln Lys Pro Gly Lys Ala Pro Lys Leu
            35                  40                  45

Leu Ile Tyr Ser Ala Ser Ser Leu His Ser Gly Val Pro Ser Arg Phe
        50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Thr Ala Trp Thr Phe Gly Gln Gly Thr Lys Val Glu Ile Lys
            100                 105                 110

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ala Ser Tyr
            20                  25                  30

Trp Ile Gly Trp Val Arg Gln Met Pro Gly Lys Gly Leu Glu Trp Met
        35                  40                  45

Gly Val Ile Tyr Pro Gly Thr Ser Glu Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Gly Leu Ser Ala Ser Ala Ser Gly Tyr Ser Phe Gln Tyr Trp
            100                 105                 110

Gly Gln Gly Thr Leu Val Thr Val Ser Ser
        115                 120

<210> SEQ ID NO 47
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Leu Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Gly
            20                  25                  30

Gln Ser Leu Asn Trp Tyr Gln Gln Lys Pro Gly Lys Ala Pro Lys Leu
        35                  40                  45

Leu Ile Tyr Gly Ala Ser Ser Leu Gln Ser Gly Val Pro Ser Arg Phe
50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Ile Thr Phe Gly Gln Gly Thr Lys Val Glu Ile Lys
            100                 105

<210> SEQ ID NO 48
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Trp Ile Gly Trp Val Arg Gln Met Pro Gly Lys Gly Leu Glu Trp Met
        35                  40                  45

```
Gly Met Ile Ser Pro Gly Gly Ser Thr Thr Ile Tyr Arg Pro Ser Phe
    50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Glu Met Tyr Thr Gly Tyr Gly Gly Ser Trp Tyr Phe Asp
            100                 105                 110

Tyr Trp Gly Gln Gly Thr Leu Val Thr Val Ser Ser
        115                 120

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Tyr Gly Phe Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Thr Phe Ser Ser Tyr
1               5

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Thr Phe Ser Ser Tyr Gly Phe Ser
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ile Ile Pro Ile Phe Gly Ser Ala Asn Tyr Ala Gln Lys Phe Gln
1               5                   10                  15

Gly

<210> SEQ ID NO 53
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 53

Ile Pro Ile Phe Gly Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Ser Ser Ser Pro Phe Ala Tyr
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Tyr Gly Phe Ser
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gly Thr Phe Ser Ser Tyr
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Thr Phe Ser Ser Tyr Gly Phe Ser
1               5                   10

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ile Ile Pro Ile Phe Gly Thr Ala Asn Tyr Ala Gln Lys Phe Gln
1               5                   10                  15

Gly
```

```
<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Pro Ile Phe Gly Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Ser Ser Ser Pro Phe Ala Tyr
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Tyr Tyr Trp Asn
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Ser Ile Ser Ser Tyr
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Ser Ile Ser Ser Tyr Tyr Trp Asn
1               5                   10

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 64

Tyr Ile Tyr Tyr Ser Gly Ser Thr Asn Tyr Asn Pro Ser Leu Lys Ser
1               5                   10                  15

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Tyr Ser Gly Ser
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Ile Arg Thr Trp
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Ser Trp Met Ser
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Thr Phe Arg Asn Ser
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Phe Thr Phe Arg Asn Ser Trp Met Ser
1               5                   10

<210> SEQ ID NO 70
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asn Ile Lys Arg Asp Gly Ser Glu Lys Tyr Tyr Val Asp Ser Val Lys
1               5                   10                  15
Gly

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Arg Asp Gly Ser Glu
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Gln Thr Gly Ser Phe Asp Tyr
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Tyr Tyr Trp Ser
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Asp Ser Ile Ser Val Tyr
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75
```

```
Asp Asp Ser Ile Ser Val Tyr Tyr Trp Ser
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Tyr Ser Ser Gly Asn Ile Asn Tyr Asn Pro Ser Leu Glu Ser
1               5                   10                  15

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Ser Ser Gly Asn
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Leu Asp Ala Phe Asp Ile
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Tyr Ala Met Ser
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Phe Thr Phe Thr Ser Tyr
1               5

<210> SEQ ID NO 81
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 81

Gly Phe Thr Phe Thr Ser Tyr Ala Met Ser
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Val Tyr Ser Ser Gly Asn Ile Asn Tyr Asn Pro Ser Leu Glu Ser
1               5                   10                  15

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Ser Ser Gly Asn
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Leu Asp Ala Phe Asp Ile
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Tyr Ala Ile Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Gly Thr Phe Ile Thr Tyr
1               5
```

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Thr Phe Ile Thr Tyr Ala Ile Ser
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ile Ile Pro Phe Phe Gly Thr Ala Asn Tyr Ala Gln Lys Phe Gln
1               5                   10                  15

Gly

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Pro Phe Phe Gly Thr
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Trp Glu Leu Phe Phe Phe Asp Phe
1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Tyr Tyr Ser Met Asn
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gly Phe Thr Phe Thr Tyr Tyr
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Phe Thr Phe Thr Tyr Tyr Ser Met Asn
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

His Ile Ser Ile Arg Ser Ser Thr Ile Tyr Phe Ala Asp Ser Ala Lys
1               5                   10                  15
Gly

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Ile Arg Ser Ser Thr
1               5

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ser Gly Trp Tyr Gly Asp Tyr Phe Asp Tyr
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asn Ala Arg Met Gly Val Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Ser Leu Ser Asn Ala Arg Met
1               5

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Phe Ser Leu Ser Asn Ala Arg Met Gly Val Thr
1               5                   10

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

His Ile Phe Ser Asn Asp Glu Lys Ser Tyr Ser Thr Ser Leu Lys Ser
1               5                   10                  15

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Phe Ser Asn Asp Glu
1               5

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Arg Asp Tyr Tyr Asp Ile Ser Ser Tyr Tyr Asp Tyr
1               5                   10

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 103

Asn His Asn Ile His
1               5

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Phe Thr Phe Ser Asn His
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Phe Thr Phe Ser Asn His Asn Ile His
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Ile Ser Arg Ser Ser Ser Thr Ile Tyr Tyr Ala Asp Ser Val Lys
1               5                   10                  15

Gly

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Arg Ser Ser Ser Thr
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp His Ala Gln Trp Tyr Gly Met Asp Val
1               5                   10

<210> SEQ ID NO 109
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Tyr Trp Met Ser
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Phe Thr Phe Ser Ser Tyr
1               5

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Phe Thr Phe Ser Ser Tyr Trp Met Ser
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Ile Lys Gln Asp Gly Ser Glu Lys Tyr Tyr Val Asp Ser Val Lys
1               5                   10                  15

Gly

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Gln Asp Gly Ser Glu
1               5

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 114

Glu Gly Val Asn Trp Gly Trp Arg Leu Tyr Trp His Phe Asp Leu
1               5                   10                  15

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ser Tyr Ser Met Asn
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Thr Phe Ser Ser Tyr
1               5

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gly Phe Thr Phe Ser Ser Tyr Ser Met Asn
1               5                   10

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

His Ser Ser Ile Ser Arg Gly Asn Ile Tyr Phe Ala Asp Ser Val Lys
1               5                   10                  15

Gly

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Ile Ser Arg Gly Asn
1               5

<210> SEQ ID NO 120
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ser Gly Trp Tyr Gly Asp Tyr Phe Asp Tyr
1               5                   10

<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asn Tyr Ala Met Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Phe Ala Phe Ser Asn Tyr
1               5

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Ala Phe Ser Asn Tyr Ala Met Ser
1               5                   10

<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Ile Arg Gly Gly Gly Ser Thr Tyr Tyr Ala Asp Ser Val Lys
1               5                   10                  15

Gly

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 125

Arg Gly Gly Gly Gly Ser
1               5

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Asp Phe Ile Ser Gly Thr Trp Tyr Pro Asp Tyr
1               5                   10

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Tyr Trp Ile Gly
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Tyr Arg Phe Thr Ser Tyr
1               5

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Tyr Arg Phe Thr Ser Tyr Trp Ile Gly
1               5                   10

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ser Ile Tyr Pro Asp Asp Ser Asp Thr Arg Tyr Ser Pro Ser Phe Gln
1               5                   10                  15

Gly

<210> SEQ ID NO 131
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Tyr Pro Asp Asp Ser Asp
1               5

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Thr Val Asp Tyr Pro Gly Tyr Ser Tyr Phe Asp Tyr
1               5                   10

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Asn Tyr Trp Ile Ala
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Tyr Thr Phe Thr Asn Tyr
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Tyr Thr Phe Thr Asn Tyr Trp Ile Ala
1               5                   10

<210> SEQ ID NO 136
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136
```

```
Ile Ile Tyr Pro Asp Gly Ser Asp Thr Arg Tyr Ser Pro Ser Phe Gln
1               5                   10                  15

Gly

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Tyr Pro Asp Gly Ser Asp
1               5

<210> SEQ ID NO 138
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Asp Ile Thr Ser Trp Tyr Tyr Gly Glu Pro Ala Phe Asp Ile
1               5                   10

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ser Ser Trp Ile Gly
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gly Tyr Ser Phe Thr Ser Ser
1               5

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Tyr Ser Phe Thr Ser Ser Trp Ile Gly
1               5                   10

<210> SEQ ID NO 142
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 142

Ile Ile Tyr Pro Gly Asp Ser Asp Thr Arg Tyr Ser Pro Ser Phe Gln
1               5                   10                  15

Gly

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Tyr Pro Gly Asp Ser Asp
1               5

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Leu Ser Gln Ala Met Thr Gly Phe Gly Phe Asp Tyr
1               5                   10

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Tyr Trp Ile Gly
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Tyr Gly Phe Thr Ser Tyr
1               5

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147
```

```
Gly Tyr Gly Phe Thr Ser Tyr Trp Ile Gly
1               5                   10
```

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Ile Ile His Pro Asp Asp Ser Asp Thr Lys Tyr Ser Pro Ser Phe Gln
1               5                   10                  15

Gly
```

<210> SEQ ID NO 149
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
His Pro Asp Asp Ser Asp
1               5
```

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Ser Tyr Leu Arg Gly Leu Trp Gly Gly Tyr Phe Asp Tyr
1               5                   10
```

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
Ser Ser Trp Ile Gly
1               5
```

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

```
Gly Tyr Thr Phe Pro Ser Ser
1               5
```

<210> SEQ ID NO 153
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 153

Gly Tyr Thr Phe Pro Ser Ser Trp Ile Gly
1               5                   10

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Ile Tyr Pro Asp Thr Ser His Thr Arg Tyr Ser Pro Ser Phe Gln
1               5                   10                  15

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Tyr Pro Asp Thr Ser His
1               5

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ala Ser Tyr Phe Asp Arg Gly Thr Gly Tyr Ser Ser Trp Trp Met Asp
1               5                   10                  15

Val

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Tyr Ser Met Ser
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

Gly Phe Thr Phe Ser Gln Tyr
1               5

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Phe Thr Phe Ser Gln Tyr Ser Met Ser
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ile Ser Gly Gly Gly Val Ser Thr Tyr Tyr Ala Asp Ser Val Lys
1               5                   10                  15
Gly

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Gly Gly Gly Val Ser
1               5

<210> SEQ ID NO 162
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asp Ile Ser Asp Ser Gly Gly Ser His Trp Tyr Phe Asp Tyr
1               5                   10

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Tyr Ala Met Ser
1               5

<210> SEQ ID NO 164
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 164

Gly Phe Thr Phe Ser Ser Tyr
1               5

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Phe Thr Phe Ser Ser Tyr Ala Met Ser
1               5                   10

<210> SEQ ID NO 166
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Thr Ile Ser Gly Thr Gly Gly Thr Thr Tyr Tyr Ala Asp Ser Val Lys
1               5                   10                  15

Gly

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Gly Thr Gly Gly Thr
1               5

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Val Arg Ala Gly Ile Asp Pro Thr Ala Ser Asp Val
1               5                   10

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169
```

Asn Phe Ala Met Ser
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Phe Thr Phe Asn Asn Phe
1               5

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gly Phe Thr Phe Asn Asn Phe Ala Met Ser
1               5                   10

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Ile Ser Gly Ser Gly Asp Asn Thr Tyr Tyr Ala Asp Ser Val Lys
1               5                   10                  15

Gly

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Gly Ser Gly Asp Asn
1               5

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Arg Asp Ile Gly Leu Gly Trp Tyr Ser Tyr Tyr Leu Asp Val
1               5                   10                  15

<210> SEQ ID NO 175
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 175

Ser Tyr Ala Ile Ser
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gly Thr Phe Ser Ser Tyr
1               5

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Gly Thr Phe Ser Ser Tyr Ala Ile Ser
1               5                   10

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Glu Ile Ile Pro Ile Phe Gly Thr Ala Ser Tyr Ala Gln Lys Phe Gln
1               5                   10                  15

Gly

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ile Pro Ile Phe Gly Thr
1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180
```

```
Ala Gly Trp Asp Asp Ser Trp Phe Asp Tyr
1               5                   10
```

<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

```
Ser Tyr Trp Ile Gly
1               5
```

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Gly Tyr Ser Phe Ala Ser Tyr
1               5
```

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

```
Gly Tyr Ser Phe Ala Ser Tyr Trp Ile Gly
1               5                   10
```

<210> SEQ ID NO 184
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Val Ile Tyr Pro Gly Thr Ser Glu Thr Arg Tyr Ser Pro Ser Phe Gln
1               5                   10                  15

Gly
```

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Tyr Pro Gly Thr Ser Glu
1               5
```

<210> SEQ ID NO 186
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 186

Gly Leu Ser Ala Ser Ala Ser Gly Tyr Ser Phe Gln Tyr
1               5                   10

<210> SEQ ID NO 187
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Tyr Trp Ile Gly
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Tyr Ser Phe Thr Asp Tyr
1               5

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Tyr Ser Phe Thr Asp Tyr Trp Ile Gly
1               5                   10

<210> SEQ ID NO 190
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Met Ile Ser Pro Gly Gly Ser Thr Thr Ile Tyr Arg Pro Ser Phe Gln
1               5                   10                  15

Gly

<210> SEQ ID NO 191
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191
```

```
Ser Pro Gly Gly Ser Thr
1               5

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Met Tyr Thr Gly Gly Tyr Gly Gly Ser Trp Tyr Phe Asp Tyr
1               5                   10

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Ser Ser Gln Ser Leu Val His Ser Asp Gly Asn Thr Tyr Leu Ser
1               5                   10                  15

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Lys Ile Ser Asn Arg Phe Ser
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Met Gln Ala Thr Gln Phe Pro Leu Thr
1               5

<210> SEQ ID NO 196
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Arg Ser Ser Gln Ser Leu Val His Ser Asp Gly Asn Thr Tyr Leu Ser
1               5                   10                  15

<210> SEQ ID NO 197
<211> LENGTH: 7
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 197

Lys Ile Ser Asn Arg Phe Ser
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 198

Met Gln Ala Thr Gln Phe Pro Leu Thr
1               5

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 199

Arg Ala Ser Gln Gly Ile Ser Asn Tyr Leu Ala
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 200

Ala Ala Ser Ser Leu Gln Ser
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 201

Gln Gln Tyr Asn Ser Tyr Pro Leu Thr
1               5

<210> SEQ ID NO 202
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 202

Arg Ser Ser Gln Ser Leu Val Tyr Ser Asp Glu Asn Thr Tyr Leu Asn
1               5                   10                  15

```
<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Val Ser Asn Arg Asp Ser
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Met Gln Gly Thr Tyr Trp Pro Pro Thr
1               5

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ala Ser Gln Ser Val Ser Ser Ser Leu Ala
1               5                   10

<210> SEQ ID NO 206
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Ala Ser Thr Arg Ala Thr
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Gln Tyr Ile Asn Trp Pro His
1               5

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208
```

Gln Ala Ser Gln Asp Ile Ser Asn Tyr Leu Asn
1               5                   10

<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Ala Ser Asn Leu Glu Thr
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Gln Tyr Asp Asn Phe Pro Ile Thr
1               5

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Ala Ser Gln Ser Val Ser Ser Asn Leu Ala
1               5                   10

<210> SEQ ID NO 212
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Ala Ser Thr Arg Ala Ser
1               5

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Gln Tyr Asp Asn Trp Pro Pro Leu Thr
1               5                   10

<210> SEQ ID NO 214
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 214

Arg Ala Ser Gln Ser Val Ser Ser Tyr Leu Ala
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gly Ala Ser Ser Arg Ala Thr
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gln Gln Tyr Gly Ser Ser Pro Leu Thr
1               5

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ala Ser Gln Asp Ile Ser Asn Tyr Leu Ala
1               5                   10

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ala Ala Ser Ser Leu Gln Ser
1               5

<210> SEQ ID NO 219
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Leu Gln Leu Asn Ser Phe Pro Phe Thr
1               5
```

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Arg Ala Ser Gln Gly Ile Ser Ser Trp Leu Ala
1               5                   10

<210> SEQ ID NO 221
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ala Ala Ser Ser Leu Gln Ser
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Gln Gln Ala Phe Ser Phe Pro Phe Thr
1               5

<210> SEQ ID NO 223
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Lys Ser Ser Gln Ser Val Leu Tyr Ser Tyr Asn Asn Lys Asn Tyr Val
1               5                   10                  15

Ala

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Ala Ser Thr Arg Glu Ser
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Gln Gln Tyr Tyr Ser Thr Leu Thr
1               5

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Ala Ser Gln Ser Val Ser Ser Ser Tyr Leu Ala
1               5                   10

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asp Ala Ser Ser Arg Ala Thr
1               5

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gln Gln Tyr Gly Ser Ser Pro Leu Thr
1               5

<210> SEQ ID NO 229
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Gly Ser Ser Ser Asn Ile Gly Ser Asn Tyr Val Tyr
1               5                   10

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Arg Asn Asn Gln Arg Pro Ser
1               5

<210> SEQ ID NO 231

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ala Ala Trp Asp Asp Ser Leu Ser Gly Val Val
1               5                   10

<210> SEQ ID NO 232
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Gly Ser Arg Ser Asn Ile Gly Ser Asn Tyr Val Tyr
1               5                   10

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Arg Asn Asn Gln Arg Pro Ser
1               5

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ala Ser Trp Asp Gly Ser Leu Ser Ala Val Val
1               5                   10

<210> SEQ ID NO 235
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Gly Ser Ser Ser Asn Ile Gly Ser Asn Tyr Val Tyr
1               5                   10

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236
```

-continued

Arg Asn Asn Gln Arg Pro Ser
1               5

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ala Thr Trp Asp Asp Ser Leu Gly Ser Pro Val
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Arg Ala Ser Gln Ser Ile Ser Arg Tyr Leu Asn
1               5                   10

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ala Ala Ser Ile Leu Gln Thr
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gln Gln Ser Tyr Ser Thr Thr Met Trp Thr
1               5                   10

<210> SEQ ID NO 241
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Gly Ser Ser Ser Asn Ile Gly Ser Asn Tyr Val Asn
1               5                   10

<210> SEQ ID NO 242
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 242

Gly Asp Tyr Gln Arg Pro Ser
1               5

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Thr Arg Asp Asp Ser Leu Ser Gly Ser Val Val
1               5                   10

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Arg Ala Ser Gln Ser Ile Tyr Asp Tyr Leu His
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Ala Ser Asn Leu Gln Ser
1               5

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gln Gln Ser Tyr Thr Thr Pro Leu Phe Thr
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Arg Ala Ser Gln Tyr Ile Gly Arg Tyr Leu Asn
1               5                   10

```
<210> SEQ ID NO 248
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Ala Thr Ser Leu Ala Ser
1               5

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gln Gln Ser Tyr Ser Thr Thr Ser Pro Thr
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Gly Ser Thr Ser Asn Ile Gly Arg Asn Tyr Val Tyr
1               5                   10

<210> SEQ ID NO 251
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Arg Thr Asn Gln Arg Pro Ser
1               5

<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Ala Ala Trp Asp Asp Ser Leu Ser Gly Arg Val
1               5                   10

<210> SEQ ID NO 253
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253
```

```
Ser Gly Ser Ser Ser Asn Ile Gly Ser Asn Tyr Val Tyr
1               5                   10

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Met Asn Asn Gln Arg Pro Ser
1               5

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Ala Trp Asp Asp Ser Leu Ser Ala Val Val
1               5                   10

<210> SEQ ID NO 256
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ser Gly Ser Asn Ser Asn Ile Gly Thr Asn Tyr Val Ser
1               5                   10

<210> SEQ ID NO 257
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Arg Ser Ser Arg Arg Pro Ser
1               5

<210> SEQ ID NO 258
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ala Ala Trp Asp Gly Ser Leu Ser Gly His Trp Val
1               5                   10

<210> SEQ ID NO 259
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 259

Arg Ala Ser Gln Ser Ile Asp Thr Tyr Leu Asn
1               5                   10

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Ser Ala Ser Ser Leu His Ser
1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Gln Ser Tyr Ser Thr Thr Ala Trp Thr
1               5                   10

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Ala Ser Gln Ser Ile Gly Gln Ser Leu Asn
1               5                   10

<210> SEQ ID NO 263
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gly Ala Ser Ser Leu Gln Ser
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gln Gln Ser Tyr Ser Thr Pro Ile Thr
1               5
```

```
<210> SEQ ID NO 265
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Val
            20                  25                  30

Arg Ser Arg Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asp Leu Phe Thr Phe Gly Ser Gly Thr Lys Leu Glu Ile Lys
            100                 105                 110

<210> SEQ ID NO 266
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Val Arg Gln Ala Pro Gly Lys Gly Leu Glu Trp Val
        35                  40                  45

Ala Phe Ile Arg Asn Arg Ala Arg Gly Tyr Thr Ser Asp His Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Pro Ser Tyr Tyr Val Leu Asp Tyr Trp Gly
            100                 105                 110

Gln Gly Thr Thr Val Thr Val Ser Ser
        115                 120

<210> SEQ ID NO 267
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Asp Tyr Tyr Met Thr
```

```
<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Phe Thr Phe Ser Asp Tyr
1               5

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Phe Thr Phe Ser Asp Tyr Tyr Met Thr
1               5                   10

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Arg Asn Arg Ala Arg Gly Tyr Thr
1               5

<210> SEQ ID NO 271
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Phe Ile Arg Asn Arg Ala Arg Gly Tyr Thr Ser Asp His Asn Pro Ser
1               5                   10                  15

Val Lys Gly

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asp Arg Pro Ser Tyr Tyr Val Leu Asp Tyr
1               5                   10

<210> SEQ ID NO 273
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 273

Lys Ser Ser Gln Ser Leu Phe Asn Val Arg Ser Arg Lys Asn Tyr Leu
1               5                   10                  15

Ala

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Trp Ala Ser Thr Arg Glu Ser
1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Lys Gln Ser Tyr Asp Leu Phe Thr
1               5

<210> SEQ ID NO 276
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
gacattgtga tgactcaatc ccccgactcc ctggctgtgt ccctcggcga acgcgcaact    60
atcaactgta aaagcagcca gtccctgttc aacgtccggt cgaggaagaa ctacctggcc   120
tggtatcagc agaaacctgg gcagccgccg aagcttctga tctcatgggc ctcaactcgg   180
gaaagcggag tgccagatag attctccgga tctggctccg gaaccgactt caccctgacg   240
atttcgagct tgcaagcgga ggatgtggcc gtgtactact gcaagcagtc ctacgacctc   300
ttcacctttg gttcgggcac caagctggag atcaaa                             336

<210> SEQ ID NO 277
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 277
gaagtccaac ttgtcgaatc gggaggaggc cttgtgcaac ccggtggatc cctgaggctg    60
tcatgcgcgg cctcgggctt cacctttcc gattactaca tgacctgggt cagacaggcc   120
cctggaaagg ggttggaatg ggtggcattc atccggaata gagcccgcgg atacactttcc   180
```

-continued

```
gaccacaacc ccagcgtgaa ggggcggttc accattagcc gcgacaacgc caagaactcc      240
ctctacctcc aaatgaacag cctgcgggcg gaggataccg ctgtgtacta ctgcgcccgc      300
gaccggccgt cctactatgt gctggactac tggggccagg gtactacggt caccgtctcc      360
tca                                                                   363
```

<210> SEQ ID NO 278
<211> LENGTH: 193
<212> TYPE: PRT
<213> ORGANISM: Homo sapiens

<400> SEQUENCE: 278

```
Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro
```

<210> SEQ ID NO 279
<211> LENGTH: 255
<212> TYPE: PRT
<213> ORGANISM: Homo sapiens

<400> SEQUENCE: 279

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95
```

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp
            245                 250                 255

<210> SEQ ID NO 280
<211> LENGTH: 255
<212> TYPE: PRT
<213> ORGANISM: Homo sapiens

<400> SEQUENCE: 280

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly

```
                210               215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe
                245                 250                 255
```

<210> SEQ ID NO 281
<211> LENGTH: 255
<212> TYPE: PRT
<213> ORGANISM: Homo sapiens

<400> SEQUENCE: 281

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser
                245                 250                 255
```

<210> SEQ ID NO 282
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
                20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Arg Val Arg Cys Pro Arg Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Arg
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 283
<211> LENGTH: 255
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 283
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtagtgacc gtgccctcca gcaacttcgg cacccagacc     240
tacacctgca acgta                                                      255
```

<210> SEQ ID NO 284
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 284

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Glu Val Glu Cys Pro Glu Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Ala
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Glu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 285
<211> LENGTH: 255
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 285

```
gcctccacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtagtgacc gtgccctcca gcaacttcgg cacccagacc     240
tacacctgca acgta                                                      255
```

<210> SEQ ID NO 286
<211> LENGTH: 107
<212> TYPE: PRT
<213> ORGANISM: Homo sapiens

<400> SEQUENCE: 286

```
Gly Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 287
<211> LENGTH: 255
<212> TYPE: DNA
<213> ORGANISM: Homo sapiens

<400> SEQUENCE: 287

```
ggaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctac                                                      255
```

<210> SEQ ID NO 288
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 288

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Thr Trp
```

```
            20                  25                  30

Leu Ala Trp Tyr Gln Gln Lys Pro Gly Lys Ala Pro Lys Val Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Ile Leu Thr Ile Asn Ser Leu Gln Pro
65                  70                  75                  80

Asp Asp Phe Ala Ser Tyr Tyr Cys Gln Gln Tyr Lys Ser Tyr Ser His
                85                  90                  95

Thr Phe Gly Gln Gly Thr Lys Leu Glu Ile Lys
                100                 105

<210> SEQ ID NO 289
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Tyr Tyr
            20                  25                  30

Tyr Trp Thr Trp Ile Arg Gln Pro Pro Gly Lys Gly Leu Glu Trp Ile
        35                  40                  45

Gly His Ile Tyr Tyr Ser Gly Ser Thr Asn Tyr Asn Pro Ser Leu Lys
    50                  55                  60

Ser Arg Val Thr Ile Ser Ile Asp Thr Ser Lys Asn Leu Phe Ser Leu
65                  70                  75                  80

Lys Leu Ser Ser Val Thr Ala Ala Asp Thr Ala Val Tyr Tyr Cys Ala
                85                  90                  95

Arg Ala Glu Gly Ser Leu Asp Ala Phe Asp Phe Trp Gly Gln Gly Thr
            100                 105                 110

Met Val Thr Val Ser Ser
        115

<210> SEQ ID NO 290
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Lys Ser Phe Ser Leu
```

85                  90                  95

Thr Phe Gly Gln Gly Thr Lys Leu Glu Ile Lys
                100                 105

<210> SEQ ID NO 291
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
                20                  25                  30

Tyr Met Thr Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Trp Gly Asp Tyr Trp Gly Gln Gly Thr Leu Val Thr Val Ser
                100                 105                 110

Ser

<210> SEQ ID NO 292
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Val Leu Ile
            35                  40                  45

Tyr Lys Ala Ser Thr Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly His Gly Thr Lys Leu Glu Ile Lys
                100                 105

<210> SEQ ID NO 293
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Val Gln Leu Gln Glu Ser Gly Pro Gly Leu Val Lys Pro Ser Gly
1               5                   10                  15

Thr Leu Ser Leu Thr Cys Thr Val Ser Gly Gly Ser Ile Asp Tyr Tyr
            20                  25                  30

Phe Trp Asn Trp Phe Arg Gln Ser Pro Val Lys Gly Leu Glu Trp Ile
        35                  40                  45

Gly His Val Tyr Asp Ile Gly Asn Thr Lys Tyr Asn Pro Ser Leu Lys
    50                  55                  60

Ser Arg Val Thr Ile Ser Ile Asp Thr Ser Glu Asn Gln Phe Ser Leu
65                  70                  75                  80

Lys Leu Asn Ser Val Thr Ala Ala Asp Thr Ala Val Tyr Tyr Cys Ala
                85                  90                  95

Arg Gly Glu Gly Ala Leu Asp Ala Phe Asp Ile Trp Gly Gln Gly Thr
            100                 105                 110

Met Val Thr Val Ser Ser
            115

<210> SEQ ID NO 294
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Asp Ile Gln Met Thr Gln Ser Pro Ser Ile Leu Ser Ala Ser Val Gly
1               5                   10                  15

Asp Arg Val Thr Ile Thr Cys Arg Ala Ser Gln Ser Val Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Thr Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Asn Thr Tyr Ser His
                85                  90                  95

Thr Phe Gly Gln Gly Thr Lys Leu Glu Ile Lys
            100                 105

<210> SEQ ID NO 295
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gln Val Gln Leu Gln Glu Ser Gly Pro Gly Leu Val Lys Pro Ser Glu
1               5                   10                  15

Thr Leu Ser Leu Asn Cys Thr Val Ser Gly Gly Ser Ile Ser Tyr Tyr
            20                  25                  30

Tyr Trp Thr Trp Ile Arg Gln Pro Pro Gly Lys Gly Leu Glu Trp Ile
        35                  40                  45

Gly His Val Ile Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Val
                85                  90                  95

Arg Ala Glu Gly Ser Leu Asp Ala Phe Asp Leu Trp Gly Gln Gly Thr
            100                 105                 110

Met Val Thr Val Ser Ser
            115

<210> SEQ ID NO 296
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Phe
                85                  90                  95

Thr Phe Gly Pro Gly Thr Lys Val Asp Ile Lys
            100                 105

<210> SEQ ID NO 297
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asp Tyr
                20                  25                  30

Gly Ile His Trp Val Arg Gln Ala Pro Gly Met Gly Gln Glu Trp Val
            35                  40                  45

Ala Val Ile Trp Tyr Asp Gly Ser Ile Lys Lys Tyr Ser Asp Ser Val
    50                  55                  60

Lys Gly Arg Phe Ile Ile Ser Arg Asp Asn Ser Glu Asn Thr Val Tyr
65                  70                  75                  80

Leu Gln Met Asn Ser Leu Arg Gly Glu Asp Thr Ala Ile Tyr Tyr Cys
                85                  90                  95

Ala Arg Asp Glu Val Gly Thr Phe Gly Ala Phe Asp Phe Trp Gly Gln
            100                 105                 110

<210> SEQ ID NO 298
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 298

Asp Ile Gln Met Thr Gln Ser Pro Ser Ser Leu Ser Ala Ser Val Gly
1               5                   10                  15

Asp Ser Ile Thr Ile Thr Cys Arg Ala Ser Gln Asp Ile Asp Asn Tyr
            20                  25                  30

Leu Ala Trp Tyr Gln Gln Lys Thr Gly Lys Val Pro Lys Val Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Gly Pro Arg
                85                  90                  95

Thr Phe Gly Gln Gly Thr Lys Val Glu Ile Lys
            100                 105

<210> SEQ ID NO 299
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 299

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Asp
            20                  25                  30

Gly Tyr Tyr Trp Ser Trp Ile Arg Gln Asn Pro Gly Lys Gly Leu Glu
        35                  40                  45

Trp Ile Gly Tyr Met Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Thr Arg Asp Phe Gly Trp Tyr Phe Asp Leu Trp Gly Arg Gly Thr
            100                 105                 110

Leu Val Thr Val Ser Ser
            115

<210> SEQ ID NO 300
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 300

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Thr Trp Tyr Gln Gln Lys Pro Gly Arg Val Pro Glu Val Leu Ile
        35                  40                  45

Tyr Ala Ala Ser Ala Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Ser Ala Pro Arg
                85                  90                  95

Thr Phe Gly Gln Gly Thr Lys Val Glu Ile Lys
            100                 105

<210> SEQ ID NO 301
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Gln Val Gln Leu Gln Glu Ser Gly Pro Gly Leu Val Lys Pro Ser Gln
1               5                   10                  15

Ser Leu Ser Leu Thr Cys Ser Val Ser Gly Ser Val Ser Ser Asp
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Arg Arg Ile Thr Asp Tyr Asn Pro Ser
50                  55                  60

Leu Lys Ser Arg Val Asn Ile Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Phe Gly Trp Tyr Phe Asp Leu Trp Gly Arg Gly Thr
            100                 105                 110

Leu Val Ala Val Ser Ser
        115

<210> SEQ ID NO 302
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Val Leu Ile Leu Leu Gly Ser Asn Arg Ala Ser Gly Val Pro

```
                    50                  55                  60

Asp Arg Val Ser Ala Ser Gly Ser Gly Thr Asp Phe Thr Leu Lys Ile
 65                  70                  75                  80

Ser Arg Met Gln Ala Glu Asp Val Gly Ile Tyr Tyr Cys Met Gln Thr
                    85                  90                  95

Leu Gln Thr Pro Phe Thr Phe Gly Gln Gly Thr Lys Leu Glu Ile Lys
                100                 105                 110

<210> SEQ ID NO 303
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Leu His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Thr Thr Ala Tyr
 65                  70                  75                  80

Met Glu Leu Ser Arg Leu Arg Ile Asp Asp Thr Ala Val Tyr Tyr Cys
                85                  90                  95

Ala Arg Asp Arg Gly Val Thr Met Ile Val Asp Gly Met Asp Asp Trp
                100                 105                 110

Gly Gln Gly Thr Thr Val Thr Val Ser Ser
                115                 120

<210> SEQ ID NO 304
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Ile Gln Leu Thr Gln Ser Pro Ser Phe Leu Ser Ala Ser Val Gly
 1               5                  10                  15

Asp Arg Val Ile Ile Thr Cys Arg Ala Ser Gln Gly Ile Asn Ser His
                20                  25                  30

Leu Ala Trp Tyr Gln Gln Lys Pro Gly Lys Ala Pro Lys Leu Leu Ile
                35                  40                  45

Tyr Tyr Ala Ser Thr Leu Pro Ser Gly Val Pro Ser Arg Phe Ser Gly
 50                  55                  60

Ser Gly Ser Gly Thr Glu Phe Thr Leu Thr Val Thr Ser Leu Gln Pro
 65                  70                  75                  80

Glu Asp Phe Ala Thr Tyr Tyr Cys Gln Gln Leu Asn His Tyr Pro Ile
                85                  90                  95

Thr Phe Gly Gln Gly Thr Arg Leu Asp Ile Asn
                100                 105
```

<210> SEQ ID NO 305
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Val Glu Leu Val Glu Ser Gly Gly Met Val Gln Pro Gly Arg
1               5                   10                  15

Ser Leu Arg Leu Ser Cys Ala Ala Ser Gly Phe Thr Phe Ser Asp Tyr
                20                  25                  30

Gly Met His Trp Val Arg Gln Ala Pro Gly Met Gly Leu Glu Trp Val
            35                  40                  45

Thr Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Val Phe
65                  70                  75                  80

Leu Gln Met Asn Ser Leu Arg Ala Glu Asp Thr Ala Val Tyr Tyr Cys
                85                  90                  95

Ala Arg Asp Glu Val Gly Phe Val Gly Ala Phe Asp Ile Trp Gly Gln
            100                 105                 110

Gly Thr Met Val Thr Val Ser Ser
        115                 120

<210> SEQ ID NO 306
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Val Glu Ile Lys
            100                 105

<210> SEQ ID NO 307
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Gly Ser Ile Ser Ser Asp
             20                  25                  30

Gly Tyr Tyr Trp Ser Trp Ile Arg Gln His Pro Gly Lys Gly Leu Glu
         35                  40                  45

Trp Ile Gly Tyr Met Tyr Tyr Ser Gly Ile Thr Tyr His Asn Pro Ser
 50                  55                  60

Leu Lys Ser Arg Val Thr Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
             85                  90                  95

Cys Ala Arg Asp Phe Gly Trp Tyr Phe Asp Leu Trp Gly Arg Gly Thr
            100                 105                 110

Leu Val Thr Val Ser Ser
            115

<210> SEQ ID NO 308
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Asp Asp Phe Ala Ala Tyr Tyr Cys Gln Lys Tyr Asn Ser Ala Pro Arg
             85                  90                  95

Thr Phe Gly Gln Gly Thr Lys Val Glu Ile Lys
            100                 105

<210> SEQ ID NO 309
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
             20                  25                  30

Ala Tyr Tyr Trp Ser Trp Ile Arg Gln His Pro Gly Lys Gly Leu Glu
         35                  40                  45

Trp Ile Gly Tyr Met Tyr Tyr Ser Gly Ile Thr Tyr Tyr Asn Pro Ser
 50                  55                  60

Leu Lys Ser Arg Val Thr Ile Ser Val Asp Thr Ser Lys Asn Gln Phe
65                  70                  75                  80
```

Ser Leu Lys Leu Ser Ser Val Thr Ala Ala Asp Thr Ala Val Tyr Tyr
            85                  90                  95

Cys Ala Arg Asp Phe Gly Trp Tyr Phe Asp Leu Trp Gly Arg Gly Thr
        100                 105                 110

Leu Val Thr Val Ser Ser
        115

<210> SEQ ID NO 310
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Asp Ile Gln Leu Thr Gln Ser Pro Ser Phe Leu Ser Ala Ser Val Gly
1               5                   10                  15

Asp Arg Val Ser Ile Thr Cys Arg Ala Ser Gln Asp Ile Ser Ser Phe
            20                  25                  30

Leu Ala Trp Tyr Gln Gln Lys Pro Gly Lys Ala Pro Val Leu Leu Ile
        35                  40                  45

Tyr Val Ala Ser Thr Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Gln Gln Leu His Val Tyr Pro Ile
                85                  90                  95

Thr Phe Gly Gln Gly Thr Arg Leu Glu Ile Arg
        100                 105

<210> SEQ ID NO 311
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asp Tyr
            20                  25                  30

Gly Ile His Trp Val Arg Gln Ala Pro Gly Met Gly Gln Glu Trp Val
        35                  40                  45

Ala Val Ile Trp Tyr Asp Gly Ser Ile Lys Lys Tyr Ser Asp Ser Val
    50                  55                  60

Lys Gly Arg Phe Ile Ile Ser Arg Asp Asn Ser Glu Asn Thr Val Tyr
65                  70                  75                  80

Leu Gln Met Asn Ser Leu Arg Gly Glu Asp Thr Ala Ile Tyr Tyr Cys
                85                  90                  95

Ala Arg Asp Glu Val Gly Thr Phe Gly Ala Phe Asp Phe Trp Gly Gln
        100                 105                 110

Gly Thr Lys Val Thr Val Ser Ser
        115                 120

<210> SEQ ID NO 312

<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro Phe Thr Phe Gly Pro Gly Thr Lys Val Asp Ile
            100                 105                 110

Lys

<210> SEQ ID NO 313
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Gly Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ser Leu Ile Val Gly Ala Ile Ser Leu Phe Asp Tyr Trp
            100                 105                 110

Gly Gln Gly Thr Leu Val Thr Val Ser Ser
        115                 120

<210> SEQ ID NO 314
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Asp Ile Gln Met Thr Gln Ser Pro Ser Ala Leu Ser Ala Ser Val Gly

```
            1               5                  10                 15
Asp Arg Val Ala Ile Thr Cys Arg Ala Ser Gln Thr Ile Ser Thr Trp
                    20                  25                 30

Leu Ala Trp Tyr Gln Gln Lys Pro Gly Lys Ala Pro Lys Val Leu Ile
            35                  40                 45

Tyr Lys Ala Ser Asn Leu Glu Ser Gly Val Pro Ser Arg Phe Ser Gly
        50                  55                 60

Ser Gly Ser Gly Thr Glu Phe Thr Leu Thr Ile Asn Ser Leu Gln Pro
65                  70                  75                 80

Asp Asp Phe Ala Thr Tyr Tyr Cys Gln Gln Tyr Gln Thr Phe Ser His
                    85                  90                 95

Thr Phe Gly Gln Gly Thr Lys Leu Glu Ile Lys
                100                 105
```

<210> SEQ ID NO 315
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 315

```
            1               5                  10                 15
Gln Val Gln Leu Arg Glu Ser Gly Pro Gly Leu Val Lys Pro Ser Glu

Thr Leu Ser Leu Thr Cys Thr Ile Ser Gly Ser Ile Ser Tyr Tyr
                    20                  25                 30

Phe Trp Thr Trp Ile Arg Gln Pro Pro Gly Arg Gly Leu Glu Trp Ile
            35                  40                 45

Gly Gln Ile Tyr Tyr Ser Gly Asn Thr Asn Ser Asn Pro Ser Leu Lys
        50                  55                 60

Ser Arg Val Thr Ile Ser Ile Asp Thr Ser Lys Asn Gln Phe Ser Leu
65                  70                  75                 80

Lys Leu Thr Ser Val Thr Val Ala Asp Thr Ala Val Tyr Tyr Cys Val
                    85                  90                 95

Arg Ala Glu Gly Ser Leu Asp Ala Phe Asp Ile Trp Gly Gln Gly Thr
                100                 105                110

Met Val Ala Val Ser Ser
            115
```

<210> SEQ ID NO 316
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 316

```
            1               5                  10                 15
Asp Met Gln Met Thr Gln Ser Pro Ser Ser Leu Ser Ala Ser Val Gly

Asp Arg Val Thr Leu Thr Cys Arg Ala Ser Gln Gly Ile Ser Asn Tyr
                    20                  25                 30

Leu Ala Trp Phe Gln Leu Lys Pro Gly Lys Val Pro Lys Leu Leu Ile
            35                  40                 45

Tyr Ala Ala Ser Thr Leu Gln Ser Gly Val Pro Ser Arg Phe Ser Gly
        50                  55                 60

Ser Gly Ser Gly Thr Asp Phe Ala Leu Thr Ile Ser Ser Leu Gln Pro
```

```
                65                  70                  75                  80
Glu Asp Val Ala Thr Tyr Tyr Cys Gln Lys Tyr Asn Ser Ala Pro Leu
                    85                  90                  95

Thr Phe Gly Gly Gly Thr Lys Val Glu Ile Lys
            100                 105
```

<210> SEQ ID NO 317
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

```
Glu Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Ser Tyr
            20                  25                  30

Ser Met Asn Trp Val Arg Gln Phe Pro Gly Lys Gly Leu Glu Trp Val
        35                  40                  45

Ser Ser Ile Ser Thr Ser Ser Asn Tyr Ile His Tyr Ala Asp Ser Leu
    50                  55                  60

Gln Gly Arg Phe Thr Ile Ser Arg Asp Asn Ala Lys Asn Ser Leu Tyr
65                  70                  75                  80

Leu Gln Met Ser Ser Leu Arg Val Glu Asp Thr Ala Val Tyr Tyr Cys
                85                  90                  95

Val Arg Asp Lys Gly Thr Thr Leu Thr Asn Trp Tyr Phe Asp Leu Trp
            100                 105                 110

Gly Arg Gly Thr Leu Val Thr Val Ser Ser
        115                 120
```

<210> SEQ ID NO 318
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Leu Val His Ser
            20                  25                  30

Asn Gly Tyr Asn Tyr Leu Asn Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Asp Phe Thr Leu Lys Ile
65                  70                  75                  80

Ser Arg Met Glu Ala Glu Asp Val Gly Val Tyr Tyr Cys Met Gln Ala
                85                  90                  95

Ile Gln Thr Pro Tyr Thr Phe Gly Gln Gly Thr Asn Val Glu Ile Lys
            100                 105                 110
```

<210> SEQ ID NO 319
<211> LENGTH: 121
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 319

Gln Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Ser Gly Ser Ser Asp Ala Phe Asp Ile Trp Gly
            100                 105                 110

Gln Gly Thr Met Val Thr Val Ser Ser
        115                 120

<210> SEQ ID NO 320
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Cys
                85                  90                  95

Thr Phe Gly Gln Gly Thr Lys Leu Glu Ile Lys
            100                 105

<210> SEQ ID NO 321
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Gln Val Gln Leu Gln Glu Ser Gly Pro Gly Leu Val Gln Pro Ser Glu
1               5                   10                  15

Thr Leu Ser Leu Thr Cys Thr Val Ser Gly Gly Ser Ile Ser Tyr Tyr
            20                  25                  30
```

```
Tyr Trp Ser Trp Ile Arg Gln Pro Pro Gly Lys Gly Leu Glu Trp Ile
            35                  40                  45

Gly Asn Ile Asn Tyr Met Gly Asn Thr Ile Tyr Asn Pro Ser Leu Lys
 50                  55                  60

Ser Arg Val Thr Ile Ser Val Asp Thr Ser Lys Asp Gln Phe Ser Leu
 65                  70                  75                  80

Lys Leu Thr Ser Val Ser Ala Ala Asp Thr Ala Val Tyr Tyr Cys Val
                85                  90                  95

Arg Ala Glu Gly Ser Leu Asp Ala Phe Asp Phe Trp Gly Gln Gly Thr
               100                 105                 110

Leu Val Ala Val Ser Leu
               115

<210> SEQ ID NO 322
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Asp Ile Gln Met Thr Gln Ser Pro Ser Ser Leu Ser Ala Ser Val Gly
 1               5                  10                  15

Asp Arg Ile Ile Phe Thr Cys Gln Ala Ser Gln Asp Ile Asn Asn Tyr
                20                  25                  30

Leu His Trp Tyr Gln Gln Lys Pro Gly Lys Ala Pro Lys Leu Leu Ile
            35                  40                  45

Tyr Asp Ala Ser Asp Trp Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp His Leu Pro Ile
                85                  90                  95

Thr Phe Gly Gln Gly Thr Arg Val Glu Ile Lys
               100                 105

<210> SEQ ID NO 323
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Gln Val Gln Leu Val Gln Ser Gly Ala Glu Val Thr Lys Pro Gly Ala
 1               5                  10                  15

Ser Val Lys Val Ser Cys Lys Ala Ser Gly Tyr Ile Phe Thr Gly Tyr
                20                  25                  30

Tyr Ile Tyr Trp Val Arg Gln Ala Pro Gly Gln Gly Leu Glu Trp Met
            35                  40                  45

Gly Trp Ile Asn Pro Ser Ser Gly Gly Thr Asn Tyr Ala Gln Lys Phe
 50                  55                  60

Gln Gly Arg Val Thr Met Ala Arg Asp Thr Ser Ile Ser Thr Ala Tyr
 65                  70                  75                  80

Met Glu Leu Ser Ser Leu Arg Ser Asp Asp Thr Ala Val Tyr Tyr Cys
                85                  90                  95
```

Ala Arg Asp Arg Lys Arg Glu Tyr Tyr Tyr Asn Phe Gly Met Asp Val
            100                 105                 110

Trp Gly Gln Gly Thr Thr Val Thr Val Ser Thr
        115                 120

<210> SEQ ID NO 324
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Asp Ile Gln Met Thr Gln Ser Pro Ser Ser Leu Ser Ala Ser Val Gly
1               5                   10                  15

Asp Arg Val Ile Leu Thr Cys Gln Ala Ser Gln Asp Ile Ser Asn Tyr
            20                  25                  30

Leu His Trp Tyr Gln Gln Lys Pro Gly Lys Ala Pro Lys Leu Leu Ile
        35                  40                  45

Tyr Asp Ala Ser Asp Leu Glu Thr Gly Val Pro Ser Arg Phe Ser Gly
    50                  55                  60

Ser Gly Ser Gly Ala Asp Phe Thr Phe Thr Ile Ser Asn Leu Gln Pro
65                  70                  75                  80

Glu Asp Phe Ala Thr Tyr Tyr Cys Gln Gln Tyr Asp His Leu Pro Ile
                85                  90                  95

Thr Phe Gly Gln Gly Thr Arg Leu Glu Ile Lys
            100                 105

<210> SEQ ID NO 325
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Val Gln Ser Gly Ala Glu Val Thr Lys Pro Gly Ala
1               5                   10                  15

Ser Val Lys Val Ser Cys Lys Ala Ser Gly Tyr Thr Phe Thr Ser His
            20                  25                  30

Tyr Ile Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Val Thr Met Ala Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Asp Arg Lys Arg Glu Tyr Tyr Tyr Asn Phe Gly Met Asp Val
            100                 105                 110

Trp Gly Gln Gly Thr Thr Val Thr Val Ser Ala
        115                 120

<210> SEQ ID NO 326
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 326

Asp Ile Gln Met Thr Gln Ser Pro Ser Ser Leu Ser Ala Ser Val Gly
1               5                   10                  15

Asp Arg Val Ile Leu Thr Cys Gln Ala Ser Gln Asp Ile Ser Asn Tyr
            20                  25                  30

Leu His Trp Tyr Gln Gln Lys Pro Gly Lys Ala Pro Lys Leu Leu Ile
        35                  40                  45

Tyr Asp Ala Ser Asp Leu Glu Thr Gly Val Pro Ser Arg Phe Ser Gly
50                  55                  60

Ser Gly Ser Gly Ala Asp Phe Thr Phe Thr Ile Ser Asn Leu Gln Pro
65                  70                  75                  80

Glu Asp Phe Ala Thr Tyr Tyr Cys Gln Gln Tyr Asp His Leu Pro Ile
                85                  90                  95

Thr Phe Gly Gln Gly Thr Arg Leu Glu Ile Lys
            100                 105

<210> SEQ ID NO 327
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Gln Val Gln Leu Val Gln Phe Gly Val Glu Val Arg Lys Pro Gly Ala
1               5                   10                  15

Ser Val Lys Val Ser Cys Lys Val Ser Gly Phe Thr Phe Thr Ser His
            20                  25                  30

Tyr Ile Tyr Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
50                  55                  60

Gln Asp Arg Val Thr Met Ala Arg Asp Thr Ser Ile Ser Thr Ala Tyr
65                  70                  75                  80

Met Glu Leu Ser Arg Leu Arg Ser Asp Asp Thr Ser Val Tyr Tyr Cys
                85                  90                  95

Val Lys Asp Arg Lys Arg Glu Tyr Tyr Tyr Asn Phe Gly Met Asp Val
            100                 105                 110

Trp Gly Gln Gly Thr Thr Val Thr Val Ser Ser
        115                 120

<210> SEQ ID NO 328
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30
```

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 329
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Glu Val Gln Met Leu Glu Ser Gly Gly Gly Leu Ile Gln Pro Gly Gly
1               5                   10                  15

Ser Leu Arg Leu Ser Cys Lys Thr Ser Gly Phe Thr Leu Ser Ile Tyr
            20                  25                  30

Ala Ile His Trp Val Arg Gln Ala Pro Gly Arg Gly Leu Glu Trp Val
        35                  40                  45

Ser Ser Phe Gly Gly Arg Gly Ser Ser Thr Tyr Phe Ala Asp Ser Val
 50                  55                  60

Lys Gly Arg Phe Thr Ile Ser Arg Asp Ala Ser Glu Asn Ser Leu Tyr
65                  70                  75                  80

Leu His Met Asn Ser Leu Arg Ala Glu Asp Thr Ala Val Tyr Tyr Cys
                85                  90                  95

Ala Lys Glu Lys Asp Trp Gly Arg Gly Phe Asp Tyr Trp Gly Gln Gly
            100                 105                 110

Thr Leu Val Thr Val Ser Ser
        115

<210> SEQ ID NO 330
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Phe Leu Asn Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 331
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Ser Met Asn Trp Val Arg Gln Ala Pro Gly Lys Gly Leu Glu Trp Val
        35                  40                  45

Ser Ser Ile Ser Ser Ser Thr Ile Tyr Ile Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Gly Trp Glu Val Phe Thr Leu Gly Phe Asp Tyr Trp
            100                 105                 110

Gly Gln Gly Thr Gln Val Thr Val Ser Ser
        115                 120

<210> SEQ ID NO 332
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Tyr Tyr Tyr Trp Thr
1               5

<210> SEQ ID NO 333
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Gly Ser Ile Ser Tyr Tyr
1               5

<210> SEQ ID NO 334
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gly Gly Ser Ile Ser Tyr Tyr Tyr Trp Thr
1               5                   10

```
<210> SEQ ID NO 335
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

His Ile Tyr Tyr Ser Gly Ser Thr Asn Tyr Asn Pro Ser Leu Lys Ser
1               5                   10                  15

<210> SEQ ID NO 336
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Tyr Tyr Ser Gly Ser
1               5

<210> SEQ ID NO 337
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ala Glu Gly Ser Leu Asp Ala Phe Asp Phe
1               5                   10

<210> SEQ ID NO 338
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ser Asn Tyr Met Thr
1               5

<210> SEQ ID NO 339
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gly Phe Thr Val Ser Ser Asn
1               5

<210> SEQ ID NO 340
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 340

Gly Phe Thr Val Ser Ser Asn Tyr Met Thr
1               5                   10

<210> SEQ ID NO 341
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Val Ile Tyr Ser Gly Gly Ser Thr Tyr Tyr Ala Asp Ser Val Lys Gly
1               5                   10                  15

<210> SEQ ID NO 342
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Tyr Ser Gly Gly Ser
1               5

<210> SEQ ID NO 343
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Asn Trp Gly Asp Tyr Trp
1               5

<210> SEQ ID NO 344
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Tyr Tyr Phe Trp Asn
1               5

<210> SEQ ID NO 345
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gly Gly Ser Ile Asp Tyr Tyr
1               5

<210> SEQ ID NO 346
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Gly Gly Ser Ile Asp Tyr Tyr Phe Trp Asn
1               5                   10

<210> SEQ ID NO 347
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

His Val Tyr Asp Ile Gly Asn Thr Lys Tyr Asn Pro Ser Leu Lys Ser
1               5                   10                  15

<210> SEQ ID NO 348
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Tyr Asp Ile Gly Asn
1               5

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gly Glu Gly Ala Leu Asp Ala Phe Asp Ile
1               5                   10

<210> SEQ ID NO 350
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Tyr Tyr Tyr Trp Thr
1               5

<210> SEQ ID NO 351
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gly Gly Ser Ile Ser Tyr Tyr
```

<210> SEQ ID NO 352
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Gly Gly Ser Ile Ser Tyr Tyr Tyr Trp Thr
1               5                   10

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

His Val Ile Tyr Ser Gly Thr Thr Asn Tyr Asn Pro Ser Leu Lys Ser
1               5                   10                  15

<210> SEQ ID NO 354
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ile Tyr Ser Gly Thr
1               5

<210> SEQ ID NO 355
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Ala Glu Gly Ser Leu Asp Ala Phe Asp Leu
1               5                   10

<210> SEQ ID NO 356
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asp Tyr Gly Ile His
1               5

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 357

Gly Phe Thr Phe Ser Asp Tyr
1               5

<210> SEQ ID NO 358
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Phe Thr Phe Ser Asp Tyr Gly Ile His
1               5                   10

<210> SEQ ID NO 359
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Val Ile Trp Tyr Asp Gly Ser Ile Lys Lys Tyr Ser Asp Ser Val Lys
1               5                   10                  15

Gly

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Trp Tyr Asp Gly Ser Ile
1               5

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Asp Glu Val Gly Thr Phe Gly Ala Phe Asp Phe
1               5                   10

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Ser Asp Gly Tyr Tyr Trp Ser
1               5
```

```
<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Gly Ser Ile Ser Ser Asp Gly Tyr
1               5

<210> SEQ ID NO 364
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Gly Gly Ser Ile Ser Ser Asp Gly Tyr Tyr Trp Ser
1               5                   10

<210> SEQ ID NO 365
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Tyr Met Tyr Tyr Ser Gly Ser Thr Tyr Tyr Asn Pro Ser Leu Lys Ser
1               5                   10                  15

<210> SEQ ID NO 366
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Tyr Tyr Ser Gly Ser
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Asp Phe Gly Trp Tyr Phe Asp Leu
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 368

Ser Asp Gly Tyr Tyr Trp Ser
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gly Gly Ser Val Ser Ser Asp Gly Tyr
1               5

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Gly Ser Val Ser Ser Asp Gly Tyr Tyr Trp Ser
1               5                   10

<210> SEQ ID NO 371
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Tyr Ile Tyr Tyr Arg Arg Ile Thr Asp Tyr Asn Pro Ser Leu Lys Ser
1               5                   10                  15

<210> SEQ ID NO 372
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Tyr Tyr Arg Arg Ile
1               5

<210> SEQ ID NO 373
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Asp Phe Gly Trp Tyr Phe Asp Leu
1               5

<210> SEQ ID NO 374
<211> LENGTH: 5
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 374

Gly Tyr Tyr Leu His
1               5

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Gly Tyr Thr Phe Thr Gly Tyr
1               5

<210> SEQ ID NO 376
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Tyr Thr Phe Thr Gly Tyr Tyr Leu His
1               5                   10

<210> SEQ ID NO 377
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Trp Ile Asn Pro Asn Ser Gly Gly Thr Asn Tyr Ala Gln Lys Phe Gln
1               5                   10                  15

Gly

<210> SEQ ID NO 378
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Asn Pro Asn Ser Gly Gly
1               5

<210> SEQ ID NO 379
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

```
Asp Arg Gly Val Thr Met Ile Val Asp Gly Met Asp Asp
1               5                   10
```

<210> SEQ ID NO 380
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

```
Asp Tyr Gly Met His
1               5
```

<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

```
Gly Phe Thr Phe Ser Asp Tyr
1               5
```

<210> SEQ ID NO 382
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

```
Gly Phe Thr Phe Ser Asp Tyr Gly Met His
1               5                   10
```

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

```
Val Ile Trp Tyr Asp Gly Ser Asn Lys Tyr Tyr Ala Asp Ser Val Lys
1               5                   10                  15

Gly
```

<210> SEQ ID NO 384
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

```
Trp Tyr Asp Gly Ser Asn
1               5
```

<210> SEQ ID NO 385
<211> LENGTH: 11
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 385

Asp Glu Val Gly Phe Val Gly Ala Phe Asp Ile
1               5                   10

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ser Asp Gly Tyr Tyr Trp Ser
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gly Gly Ser Ile Ser Ser Asp Gly Tyr
1               5

<210> SEQ ID NO 388
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Gly Ser Ile Ser Ser Asp Gly Tyr Tyr Trp Ser
1               5                   10

<210> SEQ ID NO 389
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Tyr Met Tyr Tyr Ser Gly Ile Thr Tyr His Asn Pro Ser Leu Lys Ser
1               5                   10                  15

<210> SEQ ID NO 390
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Tyr Tyr Ser Gly Ile
1               5

<210> SEQ ID NO 391
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Asp Phe Gly Trp Tyr Phe Asp Leu
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ser Asp Ala Tyr Tyr Trp Ser
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gly Gly Ser Ile Ser Ser Asp Ala Tyr
1               5

<210> SEQ ID NO 394
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gly Gly Ser Ile Ser Ser Asp Ala Tyr Tyr Trp Ser
1               5                   10

<210> SEQ ID NO 395
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Tyr Met Tyr Tyr Ser Gly Ile Thr Tyr Tyr Asn Pro Ser Leu Lys Ser
1               5                   10                  15

<210> SEQ ID NO 396
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 396

Tyr Tyr Ser Gly Ile
1               5

<210> SEQ ID NO 397
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Asp Phe Gly Trp Tyr Phe Asp Leu
1               5

<210> SEQ ID NO 398
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Asp Tyr Gly Ile His
1               5

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Phe Thr Phe Ser Asp Tyr
1               5

<210> SEQ ID NO 400
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Gly Phe Thr Phe Ser Asp Tyr Gly Ile His
1               5                   10

<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Val Ile Trp Tyr Asp Gly Ser Ile Lys Lys Tyr Ser Asp Ser Val Lys
1               5                   10                  15

Gly
```

```
<210> SEQ ID NO 402
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Trp Tyr Asp Gly Ser Ile
1               5

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Asp Glu Val Gly Thr Phe Gly Ala Phe Asp Phe
1               5                   10

<210> SEQ ID NO 404
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Asn Ala Trp Met Ser
1               5

<210> SEQ ID NO 405
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gly Phe Thr Phe Ser Asn Ala
1               5

<210> SEQ ID NO 406
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Gly Phe Thr Phe Ser Asn Ala Trp Met Ser
1               5                   10

<210> SEQ ID NO 407
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407
```

Arg Ile Lys Ser Lys Thr Gly Gly Thr Thr Asp Tyr Ala Ala Pro
1               5                   10                  15

Val Lys Gly

<210> SEQ ID NO 408
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Lys Ser Lys Thr Gly Gly Gly Thr
1               5

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Leu Ile Val Gly Ala Ile Ser Leu Phe Asp Tyr
1               5                   10

<210> SEQ ID NO 410
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Tyr Tyr Phe Trp Thr
1               5

<210> SEQ ID NO 411
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gly Gly Ser Ile Ser Tyr Tyr
1               5

<210> SEQ ID NO 412
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Gly Gly Ser Ile Ser Tyr Tyr Phe Trp Thr
1               5                   10

<210> SEQ ID NO 413
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Gln Ile Tyr Tyr Ser Gly Asn Thr Asn Ser Asn Pro Ser Leu Lys Ser
1               5                   10                  15

<210> SEQ ID NO 414
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Tyr Tyr Ser Gly Asn
1               5

<210> SEQ ID NO 415
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Ala Glu Gly Ser Leu Asp Ala Phe Asp Ile
1               5                   10

<210> SEQ ID NO 416
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Ser Tyr Ser Met Asn
1               5

<210> SEQ ID NO 417
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gly Phe Thr Phe Ser Ser Tyr
1               5

<210> SEQ ID NO 418
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Gly Phe Thr Phe Ser Ser Tyr Ser Met Asn
```

-continued

```
1               5                   10

<210> SEQ ID NO 419
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Ser Ile Ser Thr Ser Ser Asn Tyr Ile His Tyr Ala Asp Ser Leu Gln
1               5                   10                  15

Gly

<210> SEQ ID NO 420
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ser Thr Ser Ser Asn Tyr
1               5

<210> SEQ ID NO 421
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Asp Lys Gly Thr Thr Leu Thr Asn Trp Tyr Phe Asp Leu
1               5                   10

<210> SEQ ID NO 422
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Ser Tyr Gly Met His
1               5

<210> SEQ ID NO 423
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Gly Phe Thr Phe Ser Ser Tyr
1               5

<210> SEQ ID NO 424
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 424

Gly Phe Thr Phe Ser Ser Tyr Gly Met His
1               5                   10

<210> SEQ ID NO 425
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Val Ile Trp Tyr Asp Gly Ser Asn Lys Tyr Tyr Ala Asp Ser Leu Lys
1               5                   10                  15

Gly

<210> SEQ ID NO 426
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Trp Tyr Asp Gly Ser Asn
1               5

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Asp Gly Tyr Ser Gly Ser Ser Asp Ala Phe Asp Ile
1               5                   10

<210> SEQ ID NO 428
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Tyr Tyr Tyr Trp Ser
1               5

<210> SEQ ID NO 429
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Gly Gly Ser Ile Ser Tyr Tyr
```

```
<210> SEQ ID NO 430
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly Gly Ser Ile Ser Tyr Tyr Tyr Trp Ser
1               5                   10

<210> SEQ ID NO 431
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Asn Ile Asn Tyr Met Gly Asn Thr Ile Tyr Asn Pro Ser Leu Lys Ser
1               5                   10                  15

<210> SEQ ID NO 432
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Asn Tyr Met Gly Asn
1               5

<210> SEQ ID NO 433
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Ala Glu Gly Ser Leu Asp Ala Phe Asp Phe
1               5                   10

<210> SEQ ID NO 434
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Gly Tyr Tyr Ile Tyr
1               5

<210> SEQ ID NO 435
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 435

Gly Tyr Ile Phe Thr Gly Tyr
1               5

<210> SEQ ID NO 436
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Gly Tyr Ile Phe Thr Gly Tyr Tyr Ile Tyr
1               5                  10

<210> SEQ ID NO 437
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Trp Ile Asn Pro Ser Ser Gly Gly Thr Asn Tyr Ala Gln Lys Phe Gln
1               5                   10                  15

Gly

<210> SEQ ID NO 438
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Asn Pro Ser Ser Gly Gly
1               5

<210> SEQ ID NO 439
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Asp Arg Lys Arg Glu Tyr Tyr Tyr Asn Phe Gly Met Asp Val
1               5                   10

<210> SEQ ID NO 440
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Ser His Tyr Ile Tyr
1               5
```

<210> SEQ ID NO 441
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gly Tyr Thr Phe Thr Ser His
1               5

<210> SEQ ID NO 442
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Gly Tyr Thr Phe Thr Ser His Tyr Ile Tyr
1               5                   10

<210> SEQ ID NO 443
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Trp Ile Asn Pro Asn Ser Gly Gly Thr Asn Tyr Ala Gln Lys Phe Gln
1               5                   10                  15

Asp

<210> SEQ ID NO 444
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Asn Pro Asn Ser Gly Gly
1               5

<210> SEQ ID NO 445
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Asp Arg Lys Arg Glu Tyr Tyr Tyr Asn Phe Gly Met Asp Val
1               5                   10

<210> SEQ ID NO 446
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 446

Ser His Tyr Ile Tyr
1               5

<210> SEQ ID NO 447
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Gly Phe Thr Phe Thr Ser His
1               5

<210> SEQ ID NO 448
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gly Phe Thr Phe Thr Ser His Tyr Ile Tyr
1               5                   10

<210> SEQ ID NO 449
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Trp Ile Asn Pro Asn Ser Gly Gly Thr Lys Tyr Ala Gln Lys Phe Gln
1               5                   10                  15

Asp

<210> SEQ ID NO 450
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Asn Pro Asn Ser Gly Gly
1               5

<210> SEQ ID NO 451
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Asp Arg Lys Arg Glu Tyr Tyr Tyr Asn Phe Gly Met Asp Val
1               5                   10

```
<210> SEQ ID NO 452
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ile Tyr Ala Ile His
1               5

<210> SEQ ID NO 453
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Gly Phe Thr Leu Ser Ile Tyr
1               5

<210> SEQ ID NO 454
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Gly Phe Thr Leu Ser Ile Tyr Ala Ile His
1               5                   10

<210> SEQ ID NO 455
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Ser Phe Gly Gly Arg Gly Ser Ser Thr Tyr Phe Ala Asp Ser Val Lys
1               5                   10                  15

Gly

<210> SEQ ID NO 456
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

Gly Gly Arg Gly Ser Ser
1               5

<210> SEQ ID NO 457
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 457

Glu Lys Asp Trp Gly Arg Gly Phe Asp Tyr
1               5                   10

<210> SEQ ID NO 458
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 458

Asn Tyr Ser Met Asn
1               5

<210> SEQ ID NO 459
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Gly Phe Thr Phe Ser Asn Tyr
1               5

<210> SEQ ID NO 460
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Gly Phe Thr Phe Ser Asn Tyr Ser Met Asn
1               5                   10

<210> SEQ ID NO 461
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Ser Ile Ser Ser Ser Thr Ile Tyr Ile Tyr Tyr Ala Asp Ser Val Lys
1               5                   10                  15

Gly

<210> SEQ ID NO 462
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Ser Ser Ser Thr Ile Tyr
1               5
```

<210> SEQ ID NO 463
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Asp Ile Gly Trp Glu Val Phe Thr Leu Gly Phe Asp Tyr
1               5                   10

<210> SEQ ID NO 464
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Arg Ala Ser Gln Ser Ile Ser Thr Trp Leu Ala
1               5                   10

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Lys Ala Ser Ser Leu Glu Ser
1               5

<210> SEQ ID NO 466
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Gln Gln Tyr Lys Ser Tyr Ser His Thr
1               5

<210> SEQ ID NO 467
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Arg Ala Ser Gln Ser Ile Ser Ser Trp Leu Ala
1               5                   10

<210> SEQ ID NO 468
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 468

Lys Ala Ser Ser Leu Glu Ser
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gln Gln Tyr Lys Ser Phe Ser Leu Thr
1               5

<210> SEQ ID NO 470
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Arg Ala Ser Gln Ser Ile Ser Ser Trp Leu Ala
1               5                   10

<210> SEQ ID NO 471
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Lys Ala Ser Thr Leu Glu Ser
1               5

<210> SEQ ID NO 472
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gln Gln Tyr Asn Ser Tyr Ser Tyr Thr
1               5

<210> SEQ ID NO 473
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Arg Ala Ser Gln Ser Val Ser Ser Trp Leu Ala
1               5                   10

<210> SEQ ID NO 474
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 474

Lys Ala Ser Ser Leu Glu Ser
1               5

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Gln Gln Tyr Asn Thr Tyr Ser His Thr
1               5

<210> SEQ ID NO 476
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Arg Ala Ser Gln Gly Ile Arg Asn Asp Leu Gly
1               5                   10

<210> SEQ ID NO 477
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Ala Ala Ser Ser Leu Gln Ser
1               5

<210> SEQ ID NO 478
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Leu Gln Asp Tyr Asn Tyr Pro Phe Thr
1               5

<210> SEQ ID NO 479
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Arg Ala Ser Gln Asp Ile Asp Asn Tyr Leu Ala
1               5                   10

<210> SEQ ID NO 480
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Ala Ala Ser Ala Leu Gln Ser
1               5

<210> SEQ ID NO 481
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Gln Asn Tyr Asn Ser Gly Pro Arg Thr
1               5

<210> SEQ ID NO 482
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Arg Ala Ser Gln Asp Ile Ser Asn Tyr Leu Thr
1               5                   10

<210> SEQ ID NO 483
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ala Ala Ser Ala Leu Gln Ser
1               5

<210> SEQ ID NO 484
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gln Asn Tyr Asn Ser Ala Pro Arg Thr
1               5

<210> SEQ ID NO 485
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Arg Ser Ser Gln Ser Leu Leu His Ser Asn Gly Tyr Asn Tyr Leu Asp
1               5                   10                  15

<210> SEQ ID NO 486
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Leu Gly Ser Asn Arg Ala Ser
1               5

<210> SEQ ID NO 487
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Met Gln Thr Leu Gln Thr Pro Phe Thr
1               5

<210> SEQ ID NO 488
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Arg Ala Ser Gln Gly Ile Asn Ser His Leu Ala
1               5                   10

<210> SEQ ID NO 489
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Tyr Ala Ser Thr Leu Pro Ser
1               5

<210> SEQ ID NO 490
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Gln Gln Leu Asn His Tyr Pro Ile Thr
1               5

<210> SEQ ID NO 491
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Arg Ala Ser Gln Gly Ile Ser Asn Tyr Leu Ala
1               5                   10

<210> SEQ ID NO 492
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Ala Ala Ser Thr Leu His Ser
1               5

<210> SEQ ID NO 493
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Gln Lys Tyr Asn Ser Ala Pro Arg Thr
1               5

<210> SEQ ID NO 494
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

Arg Ala Ser Gln Asp Ile Ser Asn Tyr Leu Ala
1               5                   10

<210> SEQ ID NO 495
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Ala Ala Ser Thr Leu His Ser
1               5

<210> SEQ ID NO 496
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Gln Lys Tyr Asn Ser Ala Pro Arg Thr
```

```
1               5
```

\<210\> SEQ ID NO 497
\<211\> LENGTH: 11
\<212\> TYPE: PRT
\<213\> ORGANISM: Artificial Sequence
\<220\> FEATURE:
\<223\> OTHER INFORMATION: Description of Artificial Sequence: Synthetic
      peptide

\<400\> SEQUENCE: 497

```
Arg Ala Ser Gln Asp Ile Ser Ser Phe Leu Ala
1               5                   10
```

\<210\> SEQ ID NO 498
\<211\> LENGTH: 7
\<212\> TYPE: PRT
\<213\> ORGANISM: Artificial Sequence
\<220\> FEATURE:
\<223\> OTHER INFORMATION: Description of Artificial Sequence: Synthetic
      peptide

\<400\> SEQUENCE: 498

```
Val Ala Ser Thr Leu Gln Ser
1               5
```

\<210\> SEQ ID NO 499
\<211\> LENGTH: 9
\<212\> TYPE: PRT
\<213\> ORGANISM: Artificial Sequence
\<220\> FEATURE:
\<223\> OTHER INFORMATION: Description of Artificial Sequence: Synthetic
      peptide

\<400\> SEQUENCE: 499

```
Gln Gln Leu His Val Tyr Pro Ile Thr
1               5
```

\<210\> SEQ ID NO 500
\<211\> LENGTH: 17
\<212\> TYPE: PRT
\<213\> ORGANISM: Artificial Sequence
\<220\> FEATURE:
\<223\> OTHER INFORMATION: Description of Artificial Sequence: Synthetic
      peptide

\<400\> SEQUENCE: 500

```
Arg Ser Ser Gln Ser Leu Leu Asp Ser Asp Asp Gly Asn Thr Tyr Leu
1               5                   10                  15

Asp
```

\<210\> SEQ ID NO 501
\<211\> LENGTH: 7
\<212\> TYPE: PRT
\<213\> ORGANISM: Artificial Sequence
\<220\> FEATURE:
\<223\> OTHER INFORMATION: Description of Artificial Sequence: Synthetic
      peptide

\<400\> SEQUENCE: 501

```
Thr Leu Ser Tyr Arg Ala Ser
1               5
```

\<210\> SEQ ID NO 502
\<211\> LENGTH: 9
\<212\> TYPE: PRT
\<213\> ORGANISM: Artificial Sequence

```
<220> FEATURE:
<223> OTHER INFORMATION: Description of Artificial Sequence: Synthetic
      peptide

<400> SEQUENCE: 502

Met Gln Arg Ile Glu Phe Pro Phe Thr
1               5

<210> SEQ ID NO 503
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Arg Ala Ser Gln Thr Ile Ser Thr Trp Leu Ala
1               5                   10

<210> SEQ ID NO 504
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Lys Ala Ser Asn Leu Glu Ser
1               5

<210> SEQ ID NO 505
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Gln Gln Tyr Gln Thr Phe Ser His Thr
1               5

<210> SEQ ID NO 506
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Arg Ala Ser Gln Gly Ile Ser Asn Tyr Leu Ala
1               5                   10

<210> SEQ ID NO 507
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ala Ala Ser Thr Leu Gln Ser
1               5
```

<210> SEQ ID NO 508
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Gln Lys Tyr Asn Ser Ala Pro Leu Thr
1               5

<210> SEQ ID NO 509
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Arg Ser Ser Gln Thr Leu Val His Ser Asn Gly Tyr Asn Tyr Leu Asn
1               5                   10                  15

<210> SEQ ID NO 510
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Leu Gly Ser Asn Arg Ala Ser
1               5

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Met Gln Ala Ile Gln Thr Pro Tyr Thr
1               5

<210> SEQ ID NO 512
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Arg Ala Ser Gln Ser Ile Ser Ser Trp Leu Ala
1               5                   10

<210> SEQ ID NO 513
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 513

Lys Ala Ser Asn Leu Glu Ser
1               5

<210> SEQ ID NO 514
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Gln Gln Tyr Asn Ser Tyr Ser Cys Thr
1               5

<210> SEQ ID NO 515
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Gln Ala Ser Gln Asp Ile Asn Asn Tyr Leu His
1               5                   10

<210> SEQ ID NO 516
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Asp Ala Ser Asp Trp Glu Thr
1               5

<210> SEQ ID NO 517
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gln Gln Tyr Asp His Leu Pro Ile Thr
1               5

<210> SEQ ID NO 518
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Gln Ala Ser Gln Asp Ile Ser Asn Tyr Leu His
1               5                   10

<210> SEQ ID NO 519
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 519

Asp Ala Ser Asp Leu Glu Thr
1               5

<210> SEQ ID NO 520
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Gln Gln Tyr Asp His Leu Pro Ile Thr
1               5

<210> SEQ ID NO 521
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Gln Ala Ser Gln Asp Ile Ser Asn Tyr Leu His
1               5                   10

<210> SEQ ID NO 522
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Asp Ala Ser Asp Leu Glu Thr
1               5

<210> SEQ ID NO 523
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Gln Gln Tyr Asp His Leu Pro Ile Thr
1               5

<210> SEQ ID NO 524
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Gln Ala Ser Gln Asp Ile Ser Asn Tyr Leu Asn
1               5                   10
```

<210> SEQ ID NO 525
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Asp Ala Ser Asn Leu Glu Thr
1               5

<210> SEQ ID NO 526
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Gln Gln Tyr Asp Asn Leu Pro Tyr Thr
1               5

<210> SEQ ID NO 527
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Arg Ser Ser Gln Ser Leu Leu Tyr Ser Asn Gly Tyr Asn Tyr Leu Asp
1               5                   10                  15

<210> SEQ ID NO 528
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Leu Asn Ser Asn Arg Ala Ser
1               5

<210> SEQ ID NO 529
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Met Gln Ala Leu Gln Thr Pro Leu Thr
1               5

<210> SEQ ID NO 530
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

```
<400> SEQUENCE: 530

His His His His His His His
1               5

<210> SEQ ID NO 531
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 531

His His His His His His
1               5
```